(12) United States Patent
McMillan et al.

(10) Patent No.: US 11,769,112 B2
(45) Date of Patent: *Sep. 26, 2023

(54) SYSTEMS AND METHODS FOR PROVIDING AN INTEGRATED IDENTIFIER

(71) Applicant: Experian Marketing Solutions, LLC, Schaumburg, IL (US)

(72) Inventors: Helen McMillan, San Clemente, CA (US); John Lawrence Skurtovich, Anaheim, CA (US); Anita Kress, Santa Ana, CA (US); Timothy Sumida, Yorba Linda, CA (US); Michael Charles McVey, Mission Viejo, CA (US)

(73) Assignee: Experian Marketing Solutions, LLC, Schaumburg, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/339,477

(22) Filed: Jun. 4, 2021

(65) Prior Publication Data

US 2022/0027853 A1    Jan. 27, 2022

Related U.S. Application Data

(63) Continuation of application No. 16/053,698, filed on Aug. 2, 2018, now Pat. No. 11,157,872, which is a
(Continued)

(51) Int. Cl.
*G06F 16/28* (2019.01)
*G06Q 10/10* (2023.01)
(Continued)

(52) U.S. Cl.
CPC .......... *G06Q 10/10* (2013.01); *G06F 16/284* (2019.01); *G16H 10/60* (2018.01); *G16Z 99/00* (2019.02);
(Continued)

(58) Field of Classification Search
None
See application file for complete search history.

(56) References Cited

U.S. PATENT DOCUMENTS 3,405,457 A    10/1968    Bitzer
3,752,904 A    8/1973    Waterbury
(Continued)

FOREIGN PATENT DOCUMENTS

AU    2004220812    9/2004
AU    2010200017    1/2010
(Continued)

OTHER PUBLICATIONS

U.S. Appl. No. 12/705,489, filed Feb. 12, 2010, Bargoli et al.
(Continued)

*Primary Examiner* — Belix M Ortiz Ditren
(74) *Attorney, Agent, or Firm* — Knobbe Martens Olson & Bear LLP

(57) ABSTRACT

Embodiments described herein provide systems and methods to streamline the mechanism by which data users access differently regulated data through the use of one or more integrated identifiers. The integrated identifiers lessen or eliminate the need to separately maintain one set of identifiers for regulated data and another set for non-regulated data. The methods and systems may be applicable in various credit and healthcare contexts where regulations over data use are prevalent. In one or more embodiments, a data user receives a unique integrated identifier for each of the data user's current or prospective customers, and the integrated identifiers can be used to persistently identify and track the customers over time and across applications that access regulated and/or non-regulated data. In the healthcare context, a healthcare provider may utilize a patient ID as the
(Continued)

integrated identifier. To protect privacy, the integrated identifier may not include social security numbers or birthdates.

20 Claims, 5 Drawing Sheets

Related U.S. Application Data continuation of application No. 14/617,062, filed on Feb. 9, 2015, now Pat. No. 10,075,446, which is a continuation of application No. 13/673,918, filed on Nov. 9, 2012, now Pat. No. 8,954,459, which is a continuation of application No. 12/493,115, filed on Jun. 26, 2009, now Pat. No. 8,312,033.

(60) Provisional application No. 61/076,139, filed on Jun. 26, 2008.

(51) Int. Cl.
*H04L 9/40* (2022.01)
*H04L 67/10* (2022.01)
*G16H 10/60* (2018.01)
*G16Z 99/00* (2019.01)

(52) U.S. Cl.
CPC ............ *H04L 63/102* (2013.01); *H04L 67/10* (2013.01); *G06F 2221/2149* (2013.01)

(56) References Cited

U.S. PATENT DOCUMENTS

| | | |
|---|---|---|
| 4,163,290 A | 7/1979 | Sutherlin et al. |
| 4,346,442 A | 8/1982 | Musmanno |
| 4,734,858 A | 3/1988 | Schlafly |
| 4,755,940 A | 7/1988 | Brachtl et al. |
| 4,774,664 A | 9/1988 | Campbell et al. |
| 4,795,890 A | 1/1989 | Goldman |
| 4,827,508 A | 5/1989 | Shear |
| 4,868,570 A | 9/1989 | Davis |
| 4,891,503 A | 1/1990 | Jewell |
| 4,935,870 A | 6/1990 | Burk, Jr. et al. |
| 4,977,595 A | 12/1990 | Ohta et al. |
| 4,989,141 A | 1/1991 | Lyons et al. |
| 5,126,936 A | 6/1992 | Champion et al. |
| 5,148,365 A | 9/1992 | Dembo |
| 5,216,612 A | 6/1993 | Cornett et al. |
| 5,220,501 A | 6/1993 | Lawlor et al. |
| 5,247,575 A | 9/1993 | Sprague et al. |
| 5,262,941 A | 11/1993 | Saladin |
| 5,274,547 A | 12/1993 | Zoffel et al. |
| 5,325,509 A | 6/1994 | Lautzenheiser |
| 5,336,870 A | 8/1994 | Hughes et al. |
| 5,341,429 A | 8/1994 | Stringer et al. |
| 5,351,186 A | 9/1994 | Bullock et al. |
| 5,351,293 A | 9/1994 | Michener et al. |
| 5,361,201 A | 11/1994 | Jost et al. |
| 5,383,113 A | 1/1995 | Kight et al. |
| 5,404,518 A | 4/1995 | Gilbertson et al. |
| 5,423,033 A | 6/1995 | Yuen |
| 5,500,513 A | 3/1996 | Langhans et al. |
| 5,528,701 A | 6/1996 | Aref |
| 5,555,409 A | 9/1996 | Leenstra, Sr. et al. |
| 5,563,783 A | 10/1996 | Stolfo et al. |
| 5,590,038 A | 12/1996 | Pitroda |
| 5,592,560 A | 1/1997 | Deaton et al. |
| 5,621,201 A | 4/1997 | Langhans et al. |
| 5,629,982 A | 5/1997 | Micali |
| 5,630,070 A | 5/1997 | Dietrich et al. |
| 5,640,551 A | 6/1997 | Chu et al. |
| 5,640,577 A | 6/1997 | Scharmer |
| 5,649,115 A | 7/1997 | Schrader et al. |
| 5,655,129 A | 8/1997 | Ito |
| 5,659,725 A | 8/1997 | Levy et al. |
| 5,659,731 A | 8/1997 | Gustafson |
| 5,666,528 A | 9/1997 | Thai |
| 5,689,651 A | 11/1997 | Lozman |
| 5,692,107 A | 11/1997 | Simoudis et al. |
| 5,715,314 A | 2/1998 | Payne et al. |
| 5,719,941 A | 2/1998 | Swift et al. |
| 5,729,735 A | 3/1998 | Meyering |
| 5,737,732 A | 4/1998 | Gibson et al. |
| 5,739,512 A | 4/1998 | Tognazzini |
| 5,742,769 A | 4/1998 | Lee et al. |
| 5,748,098 A | 5/1998 | Grace |
| 5,754,632 A | 5/1998 | Smith |
| 5,754,939 A | 5/1998 | Herz et al. |
| 5,765,143 A | 6/1998 | Sheldon et al. |
| 5,768,423 A | 6/1998 | Aref et al. |
| 5,774,692 A | 6/1998 | Boyer et al. |
| 5,774,870 A | 6/1998 | Storey |
| 5,778,405 A | 7/1998 | Ogawa |
| 5,797,136 A | 8/1998 | Boyer et al. |
| 5,809,322 A | 9/1998 | Akerib |
| 5,812,840 A | 9/1998 | Shwartz |
| 5,813,006 A | 9/1998 | Polnerow et al. |
| 5,819,234 A | 10/1998 | Slavin et al. |
| 5,822,750 A | 10/1998 | Jou et al. |
| 5,822,751 A | 10/1998 | Gray et al. |
| 5,825,884 A | 10/1998 | Zdepski et al. |
| 5,828,837 A | 10/1998 | Elkland |
| 5,828,840 A | 10/1998 | Cowan et al. |
| 5,832,068 A | 11/1998 | Smith |
| 5,835,915 A | 11/1998 | Carr et al. |
| 5,842,185 A | 11/1998 | Chancey et al. |
| 5,842,211 A | 11/1998 | Horadan et al. |
| 5,844,218 A | 12/1998 | Kawan et al. |
| 5,857,174 A | 1/1999 | Dugan |
| 5,864,620 A | 1/1999 | Pettitt |
| 5,866,889 A | 2/1999 | Weiss et al. |
| 5,870,721 A | 2/1999 | Norris |
| 5,878,403 A | 3/1999 | DeFrancesco |
| 5,881,131 A | 3/1999 | Farris et al. |
| 5,884,302 A | 3/1999 | Ho |
| 5,893,090 A | 4/1999 | Friedman et al. |
| 5,903,830 A | 5/1999 | Joao et al. |
| 5,903,881 A | 5/1999 | Schrader et al. |
| 5,905,985 A | 5/1999 | Malloy et al. |
| 5,913,196 A | 6/1999 | Talmor et al. |
| 5,918,227 A | 6/1999 | Polnerow et al. |
| 5,930,776 A | 7/1999 | Dykstra et al. |
| 5,933,837 A | 8/1999 | Kung |
| 5,937,392 A | 8/1999 | Alberts |
| 5,953,710 A | 9/1999 | Fleming |
| 5,956,693 A | 9/1999 | Geerlings |
| 5,961,593 A | 10/1999 | Gabber et al. |
| 5,963,932 A | 10/1999 | Jakobsson et al. |
| 5,963,939 A | 10/1999 | McCann et al. |
| 5,966,695 A | 10/1999 | Melchione et al. |
| 5,974,521 A | 10/1999 | Akerib |
| 5,978,780 A | 11/1999 | Watson |
| 5,995,947 A | 11/1999 | Fraser et al. |
| 5,999,596 A | 12/1999 | Walker et al. |
| 6,006,333 A | 12/1999 | Nielsen |
| 6,009,412 A | 12/1999 | Storey |
| 6,009,415 A | 12/1999 | Shurling et al. |
| 6,014,645 A | 1/2000 | Cunningham |
| 6,014,688 A | 1/2000 | Venkatraman et al. |
| 6,021,397 A | 2/2000 | Jones et al. |
| 6,021,943 A | 2/2000 | Chastain |
| 6,026,381 A | 2/2000 | Barton, III et al. |
| 6,026,440 A | 2/2000 | Shrader et al. |
| 6,029,149 A | 2/2000 | Dykstra et al. |
| 6,035,288 A | 3/2000 | Solomon |
| 6,038,551 A | 3/2000 | Barlow et al. |
| 6,043,815 A | 3/2000 | Simonoff et al. |
| 6,055,570 A | 4/2000 | Nielsen |
| 6,064,990 A | 5/2000 | Goldsmith |
| 6,069,941 A | 5/2000 | Byrd et al. |
| 6,070,147 A | 5/2000 | Harms et al. |
| 6,072,894 A | 6/2000 | Payne |
| 6,073,106 A | 6/2000 | Rozen et al. |
| 6,073,140 A | 6/2000 | Morgan et al. |

(56) References Cited

U.S. PATENT DOCUMENTS

| | | |
|---|---|---|
| 6,076,070 A | 6/2000 | Stack |
| 6,085,242 A | 7/2000 | Chandra |
| 6,088,686 A | 7/2000 | Walker et al. |
| 6,108,691 A | 8/2000 | Lee et al. |
| 6,112,190 A | 8/2000 | Fletcher et al. |
| 6,115,694 A | 9/2000 | Cheetham et al. |
| 6,119,103 A | 9/2000 | Basch et al. |
| 6,121,901 A | 9/2000 | Welch et al. |
| 6,128,602 A | 10/2000 | Northington et al. |
| 6,128,624 A | 10/2000 | Papierniak et al. |
| 6,144,957 A | 11/2000 | Cohen et al. |
| 6,145,088 A | 11/2000 | Stevens |
| 6,149,441 A | 11/2000 | Pellegrino et al. |
| 6,151,601 A | 11/2000 | Papierniak et al. |
| 6,157,707 A | 12/2000 | Baulier et al. |
| 6,157,927 A | 12/2000 | Schaefer et al. |
| 6,161,139 A | 12/2000 | Win et al. |
| 6,173,272 B1 | 1/2001 | Thomas et al. |
| 6,173,284 B1 | 1/2001 | Brown |
| 6,178,420 B1 | 1/2001 | Sassano |
| 6,178,442 B1 | 1/2001 | Yamazaki |
| 6,182,068 B1 | 1/2001 | Culliss |
| 6,182,219 B1 | 1/2001 | Feldbau et al. |
| 6,182,229 B1 | 1/2001 | Nielsen |
| 6,195,660 B1 | 2/2001 | Polnerow et al. |
| 6,195,738 B1 | 2/2001 | Akerib |
| 6,196,460 B1 | 3/2001 | Shin |
| 6,199,077 B1 | 3/2001 | Inala et al. |
| 6,202,053 B1 | 3/2001 | Christiansen et al. |
| 6,202,067 B1 | 3/2001 | Blood et al. |
| 6,208,998 B1 | 3/2001 | Marcus |
| 6,223,171 B1 | 4/2001 | Chaudhuri et al. |
| 6,230,188 B1 | 5/2001 | Marcus |
| 6,233,566 B1 | 5/2001 | Levine et al. |
| 6,233,588 B1 | 5/2001 | Marchoili et al. |
| 6,247,000 B1 | 6/2001 | Hawkins et al. |
| 6,253,202 B1 | 6/2001 | Gilmour |
| 6,254,000 B1 | 7/2001 | Degen et al. |
| 6,256,630 B1 | 7/2001 | Glial et al. |
| 6,263,334 B1 | 7/2001 | Fayyad et al. |
| 6,263,337 B1 | 7/2001 | Fayyad et al. |
| 6,263,447 B1 | 7/2001 | French et al. |
| 6,269,369 B1 | 7/2001 | Robertson |
| 6,275,824 B1 | 8/2001 | O'Flaherty et al. |
| 6,278,993 B1 | 8/2001 | Kumar et al. |
| 6,282,658 B2 | 8/2001 | French et al. |
| 6,289,452 B1 | 9/2001 | Arnold et al. |
| 6,292,795 B1 | 9/2001 | Peters et al. |
| 6,295,528 B1 | 9/2001 | Marcus et al. |
| 6,295,541 B1 | 9/2001 | Bodnar et al. |
| 6,304,850 B1 | 10/2001 | Keller et al. |
| 6,304,860 B1 | 10/2001 | Martin et al. |
| 6,304,869 B1 | 10/2001 | Moore et al. |
| 6,311,169 B2 | 10/2001 | Duhon |
| 6,317,783 B1 | 11/2001 | Freishtat et al. |
| 6,321,339 B1 | 11/2001 | French et al. |
| 6,327,578 B1 | 12/2001 | Linehan |
| 6,330,551 B1 | 12/2001 | Burchetta et al. |
| 6,339,769 B1 | 1/2002 | Cochrane et al. |
| 6,343,279 B1 | 1/2002 | Bissonette et al. |
| 6,347,375 B1 | 2/2002 | Reinert et al. |
| 6,353,778 B1 | 3/2002 | Brown |
| 6,353,795 B1 | 3/2002 | Ranjan |
| 6,356,937 B1 | 3/2002 | Montville et al. |
| 6,366,903 B1 | 4/2002 | Agrawal et al. |
| 6,374,262 B1 | 4/2002 | Kodama |
| 6,384,844 B1 | 5/2002 | Stewart et al. |
| 6,386,444 B1 | 5/2002 | Sullivan |
| 6,397,197 B1 | 5/2002 | Gindlesperger |
| 6,397,212 B1 | 5/2002 | Biffar |
| 6,401,118 B1 | 6/2002 | Thomas |
| 6,405,173 B1 | 6/2002 | Honarvar |
| 6,405,181 B2 | 6/2002 | Lent et al. |
| 6,405,245 B1 | 6/2002 | Burson et al. |
| 6,408,282 B1 | 6/2002 | Buist |
| 6,412,073 B1 | 6/2002 | Rangan |
| 6,421,675 B1 | 7/2002 | Ryan et al. |
| 6,421,729 B1 | 7/2002 | Paltenghe et al. |
| 6,422,462 B1 | 7/2002 | Cohen |
| 6,442,590 B1 | 8/2002 | Inala et al. |
| 6,446,200 B1 | 9/2002 | Ball et al. |
| 6,448,980 B1 | 9/2002 | Kumar et al. |
| 6,453,353 B1 | 9/2002 | Win et al. |
| 6,457,012 B1 | 9/2002 | Jatkowski |
| 6,460,127 B1 | 10/2002 | Akerib |
| 6,463,533 B1 | 10/2002 | Calamera et al. |
| 6,473,740 B2 | 10/2002 | Cockril et al. |
| 6,477,565 B1 | 11/2002 | Daswani et al. |
| 6,487,540 B1 | 11/2002 | Smith et al. |
| 6,496,819 B1 | 12/2002 | Bello et al. |
| 6,496,931 B1 | 12/2002 | Rajchel et al. |
| 6,496,936 B1 | 12/2002 | French et al. |
| 5,870,721 C1 | 1/2003 | Norris |
| 6,505,168 B1 | 1/2003 | Rothman et al. |
| 6,510,415 B1 | 1/2003 | Talmor et al. |
| 6,510,451 B2 | 1/2003 | Wu et al. |
| 6,517,587 B2 | 2/2003 | Satyavolu et al. |
| 6,523,021 B1 | 2/2003 | Monberg et al. |
| 6,523,022 B1 | 2/2003 | Hobbs |
| 6,523,041 B1 | 2/2003 | Morgan et al. |
| 6,539,377 B1 | 3/2003 | Culliss |
| 6,539,392 B1 | 3/2003 | Rebane |
| 6,543,683 B2 | 4/2003 | Hoffman |
| 6,549,904 B1 | 4/2003 | Ortega et al. |
| 6,552,670 B2 | 4/2003 | Sundaravel et al. |
| 6,564,210 B1 | 5/2003 | Korda et al. |
| 6,567,791 B2 | 5/2003 | Lent et al. |
| 6,567,850 B1 | 5/2003 | Freishtat et al. |
| 6,571,236 B1 | 5/2003 | Ruppelt |
| 6,571,334 B1 | 5/2003 | Feldbau et al. |
| 6,574,623 B1 | 6/2003 | Laung et al. |
| 6,574,736 B1 | 6/2003 | Andrews |
| 6,578,012 B1 | 6/2003 | Storey |
| 6,581,025 B2 | 6/2003 | Lehman |
| 6,581,059 B1 | 6/2003 | Barrett et al. |
| 6,587,841 B1 | 7/2003 | DeFrancesco |
| 6,594,766 B2 | 7/2003 | Rangan et al. |
| 6,601,173 B1 | 7/2003 | Mohler |
| 6,601,234 B1 | 7/2003 | Bowman-Amuah |
| 6,607,136 B1 | 8/2003 | Atsmon et al. |
| 6,611,816 B2 | 8/2003 | Lebda et al. |
| 6,615,193 B1 | 9/2003 | Kingdon et al. |
| 6,618,727 B1 | 9/2003 | Wheeler et al. |
| 6,622,131 B1 | 9/2003 | Brown et al. |
| 6,629,245 B1 | 9/2003 | Stone et al. |
| 6,633,910 B1 | 10/2003 | Rajan et al. |
| 6,647,383 B1 | 11/2003 | August et al. |
| 6,651,220 B1 | 11/2003 | Penteroudakis et al. |
| 6,654,786 B1 | 11/2003 | Fox et al. |
| 6,658,393 B1 | 12/2003 | Basch et al. |
| 6,665,677 B1 | 12/2003 | Wotring et al. |
| 6,665,715 B1 | 12/2003 | Houri |
| 6,678,694 B1 | 1/2004 | Zimmermann et al. |
| 6,679,425 B1 | 1/2004 | Sheppard et al. |
| 6,691,136 B2 | 2/2004 | Lee et al. |
| 6,694,353 B2 | 2/2004 | Sommerer |
| 6,701,348 B2 | 3/2004 | Sommerer |
| 6,703,930 B2 | 3/2004 | Skinner |
| 6,708,166 B1 | 3/2004 | Dysart et al. |
| 6,711,665 B1 | 3/2004 | Akerib et al. |
| 6,714,944 B1 | 3/2004 | Shapiro et al. |
| 6,718,313 B1 | 4/2004 | Lent et al. |
| 6,725,381 B1 | 4/2004 | Smith et al. |
| 6,725,425 B1 | 4/2004 | Rajan et al. |
| 6,734,886 B1 | 5/2004 | Hagan et al. |
| 6,738,748 B2 | 5/2004 | Wetzer |
| 6,738,759 B1 | 5/2004 | Wheeler et al. |
| 6,738,804 B1 | 5/2004 | Lo |
| 6,742,001 B2 | 5/2004 | Ripley |
| 6,745,196 B1 | 6/2004 | Colyer et al. |
| 6,745,938 B2 | 6/2004 | Sullivan |
| 6,748,426 B1 | 6/2004 | Shaffer et al. |
| 6,750,985 B2 | 6/2004 | Rhoads |
| 6,754,665 B1 | 6/2004 | Futagami et al. |

(56) References Cited

U.S. PATENT DOCUMENTS

| | | |
|---|---|---|
| 6,766,304 B2 | 7/2004 | Kemp et al. |
| 6,766,327 B2 | 7/2004 | Morgan, Jr. et al. |
| 6,766,946 B2 | 7/2004 | Iida et al. |
| 6,772,132 B1 | 8/2004 | Kemp et al. |
| 6,781,608 B1 | 8/2004 | Crawford |
| 6,782,370 B1 | 8/2004 | Stack |
| 6,782,379 B2 | 8/2004 | Lee |
| 6,792,088 B2 | 9/2004 | Takeuchi |
| 6,792,263 B1 | 9/2004 | Kite |
| 6,795,812 B1 | 9/2004 | Lent et al. |
| 6,796,497 B2 | 9/2004 | Benkert et al. |
| 6,802,042 B2 | 10/2004 | Rangan et al. |
| 6,804,346 B1 | 10/2004 | Mewhinney |
| 6,804,701 B2 | 10/2004 | Muret et al. |
| 6,805,287 B2 | 10/2004 | Bishop et al. |
| 6,807,533 B1 | 10/2004 | Land et al. |
| 6,810,323 B1 | 10/2004 | Bullock et al. |
| 6,816,850 B2 | 11/2004 | Culliss |
| 6,816,871 B2 | 11/2004 | Lee |
| 6,823,319 B1 | 11/2004 | Lynch et al. |
| 6,826,707 B1 | 11/2004 | Stevens |
| 6,829,639 B1 | 12/2004 | Lawson et al. |
| 6,829,711 B1 | 12/2004 | Kwok et al. |
| 6,839,714 B2 | 1/2005 | Wheeler et al. |
| 6,842,782 B1 | 1/2005 | Malik et al. |
| 6,845,448 B1 | 1/2005 | Chaganti et al. |
| 6,847,966 B1 | 1/2005 | Sommer et al. |
| 6,847,974 B2 | 1/2005 | Wachtel |
| 6,850,895 B2 | 2/2005 | Brodersen et al. |
| 6,853,997 B2 | 2/2005 | Wotring et al. |
| 6,857,073 B2 | 2/2005 | French et al. |
| 6,859,212 B2 | 2/2005 | Kumar et al. |
| 6,865,680 B1 | 3/2005 | Wu et al. |
| 6,871,220 B1 | 3/2005 | Rajan et al. |
| 6,871,287 B1 | 3/2005 | Ellingson |
| 6,871,789 B2 | 3/2005 | Hilton et al. |
| 6,892,307 B1 | 5/2005 | Wood et al. |
| 6,898,574 B1 | 5/2005 | Regan |
| 6,900,731 B2 | 5/2005 | Kreiner et al. |
| 6,907,408 B2 | 6/2005 | Angel |
| 6,908,030 B2 | 6/2005 | Rajasekaran et al. |
| 6,910,624 B1 | 6/2005 | Natsuno |
| 6,920,435 B2 | 7/2005 | Hoffman et al. |
| 6,928,487 B2 | 8/2005 | Eggebraaten et al. |
| 6,934,714 B2 | 8/2005 | Meinig |
| 6,934,849 B2 | 8/2005 | Kramer et al. |
| 6,934,858 B2 | 8/2005 | Woodhill |
| 6,938,011 B1 | 8/2005 | Kemp et al. |
| 6,941,323 B1 | 9/2005 | Galperin |
| 6,947,984 B2 | 9/2005 | Schweitzer et al. |
| 6,947,989 B2 | 9/2005 | Gullotta et al. |
| 6,950,807 B2 | 9/2005 | Brock |
| 6,950,809 B2 | 9/2005 | Dahan et al. |
| 6,950,858 B2 | 9/2005 | Ogami |
| 6,954,757 B2 | 10/2005 | Zargham et al. |
| 6,957,336 B2 | 10/2005 | Wheeler et al. |
| 6,962,336 B2 | 11/2005 | Glass |
| 6,963,857 B1 | 11/2005 | Johnson |
| 6,965,881 B1 | 11/2005 | Brickell et al. |
| 6,968,319 B1 | 11/2005 | Remington et al. |
| 6,970,864 B2 | 11/2005 | Marcus et al. |
| 6,973,462 B2 | 12/2005 | Dattero et al. |
| 6,976,056 B1 | 12/2005 | Kumar |
| 6,983,320 B1 | 1/2006 | Thomas et al. |
| 6,983,379 B1 | 1/2006 | Spalink et al. |
| 6,983,381 B2 | 1/2006 | Jerdonek |
| 6,983,478 B1 | 1/2006 | Grauch et al. |
| 6,985,183 B2 | 1/2006 | Jan et al. |
| 6,985,887 B1 | 1/2006 | Sunstein et al. |
| 6,985,898 B1 | 1/2006 | Ripley et al. |
| 6,986,461 B1 | 1/2006 | Geoghegan et al. |
| 6,988,082 B1 | 1/2006 | Williams et al. |
| 6,988,085 B2 | 1/2006 | Hedy |
| 6,990,591 B1 | 1/2006 | Pearson |
| 6,993,504 B1 | 1/2006 | Friesen et al. |
| 6,993,510 B2 | 1/2006 | Guy et al. |
| 6,993,572 B2 | 1/2006 | Ross, Jr. et al. |
| 6,993,596 B2 | 1/2006 | Hinton et al. |
| 6,996,542 B1 | 2/2006 | Landry |
| 6,999,941 B1 | 2/2006 | Agarwal |
| 7,003,504 B1 | 2/2006 | Angus et al. |
| 7,013,310 B2 | 3/2006 | Messing et al. |
| 7,013,315 B1 | 3/2006 | Boothby |
| 7,013,323 B1 | 3/2006 | Thomas et al. |
| 7,016,907 B2 | 3/2006 | Boreham et al. |
| 7,024,548 B1 | 4/2006 | O'Toole, Jr. |
| 7,024,689 B2 | 4/2006 | O'Donnell et al. |
| 7,028,001 B1 | 4/2006 | Muthuswamy et al. |
| 7,028,013 B2 | 4/2006 | Saeki |
| 7,028,052 B2 | 4/2006 | Chapman et al. |
| 7,035,855 B1 | 4/2006 | Kilger et al. |
| 7,039,176 B2 | 5/2006 | Borodow et al. |
| 7,039,607 B2 | 5/2006 | Watarai et al. |
| 7,039,656 B1 | 5/2006 | Tsai et al. |
| 7,043,476 B2 | 5/2006 | Robson |
| 7,046,139 B2 | 5/2006 | Kuhn et al. |
| 7,047,251 B2 | 5/2006 | Reed et al. |
| 7,047,258 B2 | 5/2006 | Balogh et al. |
| 7,050,982 B2 | 5/2006 | Sheinson et al. |
| 7,050,989 B1 | 5/2006 | Hurt et al. |
| 7,058,386 B2 | 6/2006 | McGregor et al. |
| 7,058,817 B1 | 6/2006 | Ellmore |
| 7,059,531 B2 | 6/2006 | Beenau et al. |
| 7,062,475 B1 | 6/2006 | Szabo et al. |
| 7,065,526 B2 | 6/2006 | Wissner et al. |
| 7,065,566 B2 | 6/2006 | Menard et al. |
| 7,069,240 B2 | 6/2006 | Spero et al. |
| 7,072,909 B2 | 7/2006 | Polk |
| 7,075,894 B2 | 7/2006 | Hein et al. |
| 7,076,462 B1 | 7/2006 | Nelson et al. |
| 7,076,475 B2 | 7/2006 | Honarvar et al. |
| 7,082,435 B1 | 7/2006 | Guzman et al. |
| 7,085,727 B2 | 8/2006 | VanOrman |
| 7,085,997 B1 | 8/2006 | Wu et al. |
| 7,086,586 B1 | 8/2006 | Sullivan |
| 7,089,584 B1 | 8/2006 | Sharma |
| 7,089,594 B2 | 8/2006 | Lal et al. |
| 7,092,898 B1 | 8/2006 | Mattick et al. |
| 7,103,473 B2 | 9/2006 | Ranjan |
| 7,103,602 B2 | 9/2006 | Black et al. |
| 7,107,241 B1 | 9/2006 | Pinto |
| 7,107,285 B2 | 9/2006 | Von Kaenel et al. |
| 7,110,978 B1 | 9/2006 | Chin |
| 7,117,172 B1 | 10/2006 | Black |
| 7,117,529 B1 | 10/2006 | O'Donnell et al. |
| 7,121,471 B2 | 10/2006 | Beenau et al. |
| 7,124,144 B2 | 10/2006 | Christianson et al. |
| 7,127,068 B2 | 10/2006 | Sundaravel et al. |
| 7,127,424 B2 | 10/2006 | Kemp et al. |
| 7,133,935 B2 | 11/2006 | Hedy |
| 7,139,728 B2 | 11/2006 | Rigole |
| 7,143,063 B2 | 11/2006 | Lent |
| 7,149,782 B2 | 12/2006 | Sommerer |
| 7,154,375 B2 | 12/2006 | Beenau et al. |
| 7,155,508 B2 | 12/2006 | Sankuratripati et al. |
| 7,155,725 B1 | 12/2006 | Kister et al. |
| 7,155,739 B2 | 12/2006 | Bari et al. |
| 7,167,907 B2 | 1/2007 | Shaffer et al. |
| 7,174,454 B2 | 2/2007 | Roskind |
| 7,174,455 B1 | 2/2007 | Arnold et al. |
| 7,177,846 B2 | 2/2007 | Moenickheim et al. |
| 7,178,096 B2 | 2/2007 | Rangan et al. |
| 7,181,418 B1 | 2/2007 | Zucker et al. |
| 7,181,427 B1 | 2/2007 | DeFrancesco |
| 7,184,974 B2 | 2/2007 | Shishido |
| 7,185,016 B1 | 2/2007 | Rasmussen |
| 7,188,107 B2 | 3/2007 | Moon et al. |
| 7,188,252 B1 | 3/2007 | Dunn |
| 7,194,416 B1 | 3/2007 | Provost et al. |
| 7,200,602 B2 | 4/2007 | Jonas |
| 7,200,804 B1 | 4/2007 | Khavari et al. |
| 7,203,653 B1 | 4/2007 | McIntosh |
| 7,206,768 B1 | 4/2007 | deGroeve et al. |
| 7,209,895 B2 | 4/2007 | Kundtz et al. |

(56) References Cited

U.S. PATENT DOCUMENTS

| | | | |
|---|---|---|---|
| 7,209,911 B2 | 4/2007 | Boothby et al. |
| 7,212,995 B2 | 5/2007 | Schulkins |
| 7,212,999 B2 | 5/2007 | Friesen et al. |
| 7,213,064 B2 | 5/2007 | Smith et al. |
| 7,218,912 B2 | 5/2007 | Erskine et al. |
| 7,219,107 B2 | 5/2007 | Beringer |
| 7,221,377 B1 | 5/2007 | Okita et al. |
| 7,222,085 B2 | 5/2007 | Stack |
| 7,222,369 B2 | 5/2007 | Vering et al. |
| 7,225,464 B2 | 5/2007 | Satyavolu et al. |
| 7,228,289 B2 | 6/2007 | Brumfield et al. |
| 7,228,335 B2 | 6/2007 | Caughey |
| 7,229,006 B2 | 6/2007 | Babbi et al. |
| 7,231,657 B2 | 6/2007 | Honarvar et al. |
| 7,234,156 B2 | 6/2007 | French et al. |
| 7,234,160 B2 | 6/2007 | Vogel et al. |
| 7,236,950 B2 | 6/2007 | Savage et al. |
| 7,237,267 B2 | 6/2007 | Rayes et al. |
| 7,240,059 B2 | 7/2007 | Bayliss et al. |
| 7,240,199 B2 | 7/2007 | Tomkow |
| 7,240,363 B1 | 7/2007 | Ellingson |
| 7,243,369 B2 | 7/2007 | Bhat et al. |
| 7,246,067 B2 | 7/2007 | Austin et al. |
| 7,246,361 B1 | 7/2007 | Scalora et al. |
| 7,246,740 B2 | 7/2007 | Swift et al. |
| 7,249,048 B1 | 7/2007 | O'Flaherty |
| 7,249,072 B1 | 7/2007 | Nearhood et al. |
| 7,249,076 B1 | 7/2007 | Pendleton et al. |
| 7,249,080 B1 | 7/2007 | Hoffman et al. |
| 7,249,096 B1 | 7/2007 | Lasater et al. |
| 7,249,113 B1 | 7/2007 | Continelli et al. |
| 7,251,347 B2 | 7/2007 | Smith |
| 7,263,497 B1 | 8/2007 | Wiser et al. |
| 7,263,548 B2 | 8/2007 | Daswani et al. |
| 7,272,591 B1 | 9/2007 | Ghazal et al. |
| 7,277,900 B1 | 10/2007 | Ganesh et al. |
| 7,280,980 B1 | 10/2007 | Hoadley et al. |
| 7,281,652 B2 | 10/2007 | Foss |
| 7,283,998 B2 | 10/2007 | Moon et al. |
| 7,289,971 B1 | 10/2007 | O'Neil et al. |
| 7,296,734 B2 | 11/2007 | Pliha |
| 7,302,272 B2 | 11/2007 | Ackley |
| 7,303,120 B2 | 12/2007 | Beenau et al. |
| 7,305,233 B2 | 12/2007 | Paul et al. |
| 7,310,611 B2 | 12/2007 | Shibuya et al. |
| 7,310,617 B1 | 12/2007 | Cunningham |
| 7,310,618 B2 | 12/2007 | Libman |
| 7,313,813 B2 | 12/2007 | Rangan et al. |
| 7,314,167 B1 | 1/2008 | Kiliccote |
| 7,315,837 B2 | 1/2008 | Sloan et al. |
| 7,328,233 B2 | 2/2008 | Salim et al. |
| 7,328,435 B2 | 2/2008 | Trifon |
| 7,330,717 B2 | 2/2008 | Gidron et al. |
| 7,330,831 B2 | 2/2008 | Biondi et al. |
| 7,330,835 B2 | 2/2008 | Deggendorf |
| 7,330,871 B2 | 2/2008 | Barber |
| 7,333,635 B2 | 2/2008 | Tsantes et al. |
| 7,334,020 B2 | 2/2008 | Caughey |
| 7,337,468 B2 | 2/2008 | Metzger |
| 7,340,042 B2 | 3/2008 | Cluff et al. |
| 7,340,679 B2 | 3/2008 | Botscheck et al. |
| 7,343,149 B2 | 3/2008 | Benco |
| 7,343,295 B2 | 3/2008 | Pomerance |
| 7,346,576 B2 | 3/2008 | Lent et al. |
| 7,346,703 B2 | 3/2008 | Cope |
| 7,356,503 B1 | 4/2008 | Johnson et al. |
| 7,356,506 B2 | 4/2008 | Watson et al. |
| 7,356,516 B2 | 4/2008 | Richey et al. |
| 7,366,495 B1 | 4/2008 | Magnotta et al. |
| 7,366,694 B2 | 4/2008 | Lazerson |
| 7,366,759 B2 | 4/2008 | Trevithick |
| 7,367,011 B2 | 4/2008 | Ramsey et al. |
| 7,370,014 B1 | 5/2008 | Vasavada et al. |
| 7,370,044 B2 | 5/2008 | Mulhern et al. |
| 7,370,351 B1 | 5/2008 | Ramachandran et al. |
| 7,373,324 B1 | 5/2008 | Engin et al. |
| 7,373,335 B2 | 5/2008 | Cleghorn et al. |
| 7,376,603 B1 | 5/2008 | Mayr et al. |
| 7,379,880 B1 | 5/2008 | Pathria et al. |
| 7,379,978 B2 | 5/2008 | Anderson et al. |
| 7,383,215 B1 | 6/2008 | Navarro et al. |
| 7,383,988 B2 | 6/2008 | Slonecker, Jr. |
| 7,386,448 B1 | 6/2008 | Poss et al. |
| 7,386,511 B2 | 6/2008 | Buchanan et al. |
| 7,386,554 B2 | 6/2008 | Ripley et al. |
| 7,386,786 B2 | 6/2008 | Davis et al. |
| 7,389,305 B1 | 6/2008 | Kindig et al. |
| 7,389,913 B2 | 6/2008 | Starrs |
| 7,395,241 B1 | 7/2008 | Cook et al. |
| 7,395,273 B2 | 7/2008 | Khan et al. |
| 7,400,883 B2 | 7/2008 | Rivers et al. |
| 7,401,050 B2 | 7/2008 | O'Neill |
| 7,403,923 B2 | 7/2008 | Elliott et al. |
| 7,403,942 B1 | 7/2008 | Bayliss |
| 7,409,369 B1 | 8/2008 | Homuth et al. |
| 7,412,228 B2 | 8/2008 | Barclay et al. |
| 7,412,487 B2 | 8/2008 | Caughey |
| 7,413,113 B1 | 8/2008 | Zhu |
| 7,421,322 B1 | 9/2008 | Silversmith et al. |
| 7,421,442 B2 | 9/2008 | Gelb et al. |
| 7,421,732 B2 | 9/2008 | Costa-Requena et al. |
| 7,424,439 B1 | 9/2008 | Fayyad et al. |
| 7,424,520 B2 | 9/2008 | Daswani et al. |
| 7,430,520 B1 | 9/2008 | Haugen et al. |
| 7,433,864 B2 | 10/2008 | Malik |
| 7,437,679 B2 | 10/2008 | Uemura et al. |
| 7,438,226 B2 | 10/2008 | Helsper et al. |
| 7,444,414 B2 | 10/2008 | Foster et al. |
| 7,444,518 B1 | 10/2008 | Dharmarajan et al. |
| 7,447,663 B1 | 11/2008 | Barker et al. |
| 7,451,095 B1 | 11/2008 | Bradley et al. |
| 7,451,113 B1 | 11/2008 | Kasower |
| 7,458,508 B1 | 12/2008 | Shao et al. |
| 7,460,857 B2 | 12/2008 | Roach, Jr. |
| 7,467,127 B1 | 12/2008 | Baccash et al. |
| 7,467,401 B2 | 12/2008 | Cicchitto |
| 7,475,032 B1 | 1/2009 | Patnode et al. |
| 7,475,118 B2 | 1/2009 | Leiba et al. |
| 7,478,157 B2 | 1/2009 | Bohrer et al. |
| 7,479,949 B2 | 1/2009 | Jobs et al. |
| 7,480,631 B1 | 1/2009 | Merced et al. |
| 7,483,842 B1 | 1/2009 | Fung et al. |
| 7,483,892 B1 | 1/2009 | Sommer et al. |
| 7,490,356 B2 | 2/2009 | Lieblich et al. |
| RE40,692 E | 3/2009 | Rose, Jr. |
| 7,503,489 B2 | 3/2009 | Heffez |
| 7,505,931 B2 | 3/2009 | Silva |
| 7,505,938 B2 | 3/2009 | Lang et al. |
| 7,509,117 B2 | 3/2009 | Yum |
| 7,509,278 B2 | 3/2009 | Jones |
| 7,512,221 B2 | 3/2009 | Toms |
| 7,519,558 B2 | 4/2009 | Ballard et al. |
| 7,526,796 B2 | 4/2009 | Lulich et al. |
| 7,529,698 B2 | 5/2009 | Joao |
| 7,530,097 B2 | 5/2009 | Casco-Arias et al. |
| 7,533,179 B2 | 5/2009 | Tarquini et al. |
| 7,536,329 B2 | 5/2009 | Goldberg et al. |
| 7,536,346 B2 | 5/2009 | Aliffi et al. |
| 7,536,348 B2 | 5/2009 | Shao et al. |
| 7,536,354 B1 | 5/2009 | deGroeve et al. |
| 7,542,468 B1 | 6/2009 | Begley et al. |
| 7,542,922 B2 | 6/2009 | Bennett et al. |
| 7,542,993 B2 | 6/2009 | Satterfield et al. |
| 7,543,739 B2 | 6/2009 | Brown et al. |
| 7,546,266 B2 | 6/2009 | Beirne et al. |
| 7,546,271 B1 | 6/2009 | Chmielewski et al. |
| 7,548,886 B2 | 6/2009 | Kirkland et al. |
| 7,552,080 B1 | 6/2009 | Willard et al. |
| 7,552,086 B1 | 6/2009 | Rajasekar et al. |
| 7,552,089 B2 | 6/2009 | Bruer et al. |
| 7,552,123 B2 | 6/2009 | Wade et al. |
| 7,552,190 B1 | 6/2009 | Freishtat et al. |
| 7,552,467 B2 | 6/2009 | Lindsay |
| 7,555,459 B2 | 6/2009 | Dhar et al. |

(56) References Cited

U.S. PATENT DOCUMENTS

| | | | |
|---|---|---|---|
| 7,556,192 | B2 | 7/2009 | Wokaty, Jr. |
| 7,558,748 | B2 | 7/2009 | Ehring et al. |
| 7,558,777 | B1 | 7/2009 | Santos |
| 7,558,795 | B2 | 7/2009 | Malik et al. |
| 7,559,217 | B2 | 7/2009 | Bass |
| 7,562,093 | B2 | 7/2009 | Gelb et al. |
| 7,562,184 | B2 | 7/2009 | Henmi et al. |
| 7,562,382 | B2 | 7/2009 | Hinton et al. |
| 7,562,814 | B1 | 7/2009 | Shao et al. |
| 7,566,002 | B2 | 7/2009 | Love et al. |
| 7,571,138 | B2 | 8/2009 | Miri et al. |
| 7,571,322 | B2 | 8/2009 | Karoubi |
| 7,571,473 | B1 | 8/2009 | Boydstun et al. |
| 7,575,157 | B2 | 8/2009 | Barnhardt et al. |
| 7,577,665 | B2 | 8/2009 | Ramer et al. |
| 7,577,934 | B2 | 8/2009 | Anonsen et al. |
| 7,580,884 | B2 | 8/2009 | Cook |
| 7,581,112 | B2 | 8/2009 | Brown et al. |
| 7,583,682 | B2 | 9/2009 | Hopkins |
| 7,584,126 | B1 | 9/2009 | White |
| 7,584,146 | B1 | 9/2009 | Duhon |
| 7,584,197 | B2 | 9/2009 | Dant |
| 7,587,366 | B2 | 9/2009 | Grim, III et al. |
| 7,587,368 | B2 | 9/2009 | Felsher |
| 7,593,889 | B2 | 9/2009 | Raines et al. |
| 7,593,891 | B2 | 9/2009 | Kornegay et al. |
| 7,594,019 | B2 | 9/2009 | Clapper |
| 7,596,512 | B1 | 9/2009 | Raines et al. |
| 7,596,716 | B2 | 9/2009 | Frost et al. |
| 7,603,701 | B2 | 10/2009 | Gaucas |
| 7,606,401 | B2 | 10/2009 | Hoffman et al. |
| 7,606,725 | B2 | 10/2009 | Robertson et al. |
| 7,606,752 | B2 | 10/2009 | Hazlehurst et al. |
| 7,610,216 | B1 | 10/2009 | May et al. |
| 7,610,229 | B1 | 10/2009 | Kornegay |
| 7,613,600 | B2 | 11/2009 | Krane |
| 7,613,671 | B2 | 11/2009 | Serrano-Morales et al. |
| 7,620,596 | B2 | 11/2009 | Knudson et al. |
| 7,620,602 | B2 | 11/2009 | Jakstadt et al. |
| 7,620,653 | B1 | 11/2009 | Swartz |
| 7,623,844 | B2 | 11/2009 | Herrmann et al. |
| 7,624,433 | B1 | 11/2009 | Clark et al. |
| 7,630,903 | B1 | 12/2009 | Vaidyanathan |
| 7,630,932 | B2 | 12/2009 | Danaher et al. |
| 7,630,933 | B2 | 12/2009 | Peterson et al. |
| 7,631,803 | B2 | 12/2009 | Peyret et al. |
| 7,634,651 | B1 | 12/2009 | Gerde et al. |
| 7,634,737 | B2 | 12/2009 | Beringer et al. |
| 7,636,686 | B2 | 12/2009 | Pierdinock et al. |
| 7,636,941 | B2 | 12/2009 | Blinn et al. |
| 7,640,200 | B2 | 12/2009 | Gardner et al. |
| 7,640,209 | B1 | 12/2009 | Brooks et al. |
| 7,641,113 | B1 | 1/2010 | Alvarez et al. |
| 7,644,023 | B2 | 1/2010 | Kumar et al. |
| 7,644,035 | B1 | 1/2010 | Biffle et al. |
| 7,644,285 | B1 | 1/2010 | Murray et al. |
| 7,647,274 | B2 | 1/2010 | Peterson et al. |
| 7,647,344 | B2 | 1/2010 | Skurtovich, Jr. et al. |
| 7,653,592 | B1 | 1/2010 | Flaxman et al. |
| 7,653,600 | B2 | 1/2010 | Gustin |
| 7,653,613 | B1 | 1/2010 | DeGraaff et al. |
| 7,653,688 | B2 | 1/2010 | Bittner |
| 7,657,431 | B2 | 2/2010 | Hayakawa |
| 7,657,540 | B1 | 2/2010 | Bayliss |
| 7,660,989 | B2 | 2/2010 | Tomkow |
| 7,664,725 | B2 | 2/2010 | Murray et al. |
| 7,665,657 | B2 | 2/2010 | Huh |
| 7,668,840 | B2 | 2/2010 | Bayliss et al. |
| 7,672,833 | B2 | 3/2010 | Blume et al. |
| 7,672,865 | B2 | 3/2010 | Kumar et al. |
| 7,672,879 | B1 | 3/2010 | Kumar et al. |
| 7,672,924 | B1 | 3/2010 | Scheurich et al. |
| 7,672,926 | B2 | 3/2010 | Ghazal et al. |
| 7,672,944 | B1 | 3/2010 | Holladay et al. |
| 7,676,410 | B2 | 3/2010 | Petralia |
| 7,676,463 | B2 | 3/2010 | Thompson et al. |
| 7,676,751 | B2 | 3/2010 | Allen et al. |
| 7,676,834 | B2 | 3/2010 | Camaisa et al. |
| 7,680,772 | B2 | 3/2010 | Kronberg |
| 7,685,096 | B2 | 3/2010 | Margolus et al. |
| 7,685,209 | B1 | 3/2010 | Norton et al. |
| 7,685,279 | B2 | 3/2010 | Miltonberger et al. |
| 7,685,525 | B2 | 3/2010 | Kumar et al. |
| 7,686,214 | B1 | 3/2010 | Shao et al. |
| 7,688,813 | B2 | 3/2010 | Shin et al. |
| 7,689,487 | B1 | 3/2010 | Britto et al. |
| 7,689,505 | B2 | 3/2010 | Kasower |
| 7,689,506 | B2 | 3/2010 | Fei et al. |
| 7,689,526 | B2 | 3/2010 | Byrnes et al. |
| 7,689,563 | B1 | 3/2010 | Jacobson |
| 7,690,032 | B1 | 3/2010 | Peirce |
| 7,693,787 | B2 | 4/2010 | Provinse |
| 7,697,520 | B2 | 4/2010 | Hopkins |
| 7,698,163 | B2 | 4/2010 | Reed et al. |
| 7,698,214 | B1 | 4/2010 | Lindgren |
| 7,698,217 | B1 | 4/2010 | Phillips et al. |
| 7,698,445 | B2 | 4/2010 | Fitzpatrick et al. |
| 7,698,558 | B2 | 4/2010 | Tomkow |
| 7,702,576 | B2 | 4/2010 | Fahner et al. |
| 7,707,059 | B2 | 4/2010 | Reed et al. |
| 7,707,117 | B1 | 4/2010 | Jimenez et al. |
| 7,707,122 | B2 | 4/2010 | Hull et al. |
| 7,707,164 | B2 | 4/2010 | Kapochunas et al. |
| 7,707,271 | B2 | 4/2010 | Rudkin et al. |
| 7,707,624 | B2 | 4/2010 | Tomkow |
| 7,708,190 | B2 | 5/2010 | Brandt et al. |
| 7,711,626 | B2 | 5/2010 | Nanjundamoorthy et al. |
| 7,711,635 | B2 | 5/2010 | Steele et al. |
| 7,711,707 | B2 | 5/2010 | Kelley |
| 7,715,832 | B2 | 5/2010 | Zhou |
| 7,720,705 | B2 | 5/2010 | Stein |
| 7,720,750 | B2 | 5/2010 | Brody |
| 7,720,846 | B1 | 5/2010 | Bayliss |
| 7,725,385 | B2 | 5/2010 | Royer et al. |
| 7,729,283 | B2 | 6/2010 | Ferguson et al. |
| 7,729,959 | B1 | 6/2010 | Wells et al. |
| 7,729,969 | B1 | 6/2010 | Smith, III et al. |
| 7,730,078 | B2 | 6/2010 | Schwabe et al. |
| 7,734,522 | B2 | 6/2010 | Johnson et al. |
| 7,734,541 | B2 | 6/2010 | Kumar et al. |
| 7,734,637 | B2 | 6/2010 | Greifeneder et al. |
| 7,739,139 | B2 | 6/2010 | Robertson et al. |
| 7,739,193 | B2 | 6/2010 | Zimmer et al. |
| 7,739,707 | B2 | 6/2010 | Sie et al. |
| 7,742,982 | B2 | 6/2010 | Chaudhuri et al. |
| 7,747,480 | B1 | 6/2010 | Agresta et al. |
| 7,747,494 | B1 | 6/2010 | Kothari et al. |
| 7,747,520 | B2 | 6/2010 | Livermore et al. |
| 7,747,521 | B2 | 6/2010 | Serio |
| 7,747,542 | B2 | 6/2010 | Morley et al. |
| 7,747,559 | B2 | 6/2010 | Leitner et al. |
| 7,752,179 | B2 | 7/2010 | Brown |
| 7,752,236 | B2 | 7/2010 | Williams et al. |
| 7,752,286 | B2 | 7/2010 | Anderson et al. |
| 7,752,535 | B2 | 7/2010 | Satyavolu |
| 7,756,789 | B2 | 7/2010 | Welker et al. |
| 7,757,944 | B2 | 7/2010 | Cline et al. |
| 7,761,373 | B2 | 7/2010 | Metz |
| 7,761,384 | B2 | 7/2010 | Madhogarhia |
| 7,761,568 | B1 | 7/2010 | Levi et al. |
| 7,761,569 | B2 | 7/2010 | Hopkins |
| 7,765,148 | B2 | 7/2010 | German et al. |
| 7,765,166 | B2 | 7/2010 | Beringer et al. |
| 7,765,279 | B1 | 7/2010 | Kalb et al. |
| 7,765,311 | B2 | 7/2010 | Itabashi et al. |
| 7,765,525 | B1 | 7/2010 | Davidson et al. |
| 7,769,696 | B2 | 8/2010 | Yoda |
| 7,769,697 | B2 | 8/2010 | Fieschi et al. |
| 7,769,998 | B2 | 8/2010 | Lynch et al. |
| 7,770,002 | B2 | 8/2010 | Weber |
| 7,774,257 | B2 | 8/2010 | Maggioncalda et al. |
| 7,774,270 | B1 | 8/2010 | MacCloskey |
| 7,778,868 | B2 | 8/2010 | Haugen et al. |
| 7,783,515 | B1 | 8/2010 | Kumar et al. |

(56) References Cited

U.S. PATENT DOCUMENTS

| | | |
|---|---|---|
| 7,783,749 B2 | 8/2010 | Hopkins |
| 7,787,869 B2 | 8/2010 | Rice et al. |
| 7,788,040 B2 | 8/2010 | Haskell et al. |
| 7,792,715 B1 | 9/2010 | Kasower |
| 7,792,725 B2 | 9/2010 | Booraem et al. |
| 7,792,747 B2 | 9/2010 | Chin |
| 7,792,903 B2 | 9/2010 | Fischer et al. |
| 7,793,835 B1 | 9/2010 | Coggeshall et al. |
| 7,797,224 B2 | 9/2010 | Barone et al. |
| 7,797,252 B2 | 9/2010 | Rosskamm et al. |
| 7,797,644 B1 | 9/2010 | Bhojan |
| 7,797,725 B2 | 9/2010 | Lunt et al. |
| 7,797,734 B2 | 9/2010 | Babi et al. |
| 7,801,807 B2 | 9/2010 | DeFrancesco et al. |
| 7,801,811 B1 | 9/2010 | Merrell et al. |
| 7,801,812 B2 | 9/2010 | Conlin et al. |
| 7,801,828 B2 | 9/2010 | Candella et al. |
| 7,801,896 B2 | 9/2010 | Szabo |
| 7,801,956 B1 | 9/2010 | Cumberbatch et al. |
| 7,802,104 B2 | 9/2010 | Dickinson |
| 7,805,348 B2 | 9/2010 | Nanjundamoorthy et al. |
| 7,805,362 B1 | 9/2010 | Merrell et al. |
| 7,805,439 B2 | 9/2010 | Elliott et al. |
| 7,809,398 B2 | 10/2010 | Pearson |
| 7,809,624 B1 | 10/2010 | Smith, III et al. |
| 7,809,797 B2 | 10/2010 | Cooley et al. |
| 7,810,036 B2 | 10/2010 | Bales et al. |
| 7,814,002 B2 | 10/2010 | DeFrancesco et al. |
| 7,814,005 B2 | 10/2010 | Imrey et al. |
| 7,814,431 B1 | 10/2010 | Quinn et al. |
| 7,818,228 B1 | 10/2010 | Coulter |
| 7,818,229 B2 | 10/2010 | Imrey et al. |
| 7,818,231 B2 | 10/2010 | Rajan |
| 7,818,382 B2 | 10/2010 | Sommerer |
| 7,822,624 B2 | 10/2010 | Erdmann et al. |
| 7,822,667 B1 | 10/2010 | Smith, III et al. |
| 7,827,108 B2 | 11/2010 | Perlman et al. |
| 7,827,115 B2 | 11/2010 | Weller et al. |
| 7,830,382 B2 | 11/2010 | Cirit et al. |
| 7,831,609 B1 | 11/2010 | Alexander |
| 7,832,006 B2 | 11/2010 | Chen et al. |
| 7,835,983 B2 | 11/2010 | Lefner et al. |
| 7,835,990 B2 | 11/2010 | Coleman |
| 7,836,111 B1 | 11/2010 | Shan |
| 7,840,484 B2 | 11/2010 | Haggerty et al. |
| 7,840,597 B2 | 11/2010 | Showalter et al. |
| 7,840,674 B1 | 11/2010 | Sterling |
| 7,841,004 B1 | 11/2010 | Balducci et al. |
| 7,841,008 B1 | 11/2010 | Cole et al. |
| 7,844,520 B1 | 11/2010 | Franklin |
| 7,844,604 B2 | 11/2010 | Baio et al. |
| 7,848,972 B1 | 12/2010 | Sharma |
| 7,848,978 B2 | 12/2010 | Imrey et al. |
| 7,849,014 B2 | 12/2010 | Erikson |
| 7,849,397 B1 | 12/2010 | Ahmed |
| 7,849,624 B2 | 12/2010 | Holt et al. |
| 7,853,493 B2 | 12/2010 | DeBie et al. |
| 7,853,518 B2 | 12/2010 | Cagan |
| 7,853,522 B2 | 12/2010 | Chin |
| 7,853,533 B2 | 12/2010 | Eisen |
| 7,853,984 B2 | 12/2010 | Antell et al. |
| 7,856,203 B2 | 12/2010 | Lipovski |
| 7,856,376 B2 | 12/2010 | Storey |
| 7,856,386 B2 | 12/2010 | Hazlehurst et al. |
| 7,856,453 B2 | 12/2010 | Malik et al. |
| 7,860,769 B2 | 12/2010 | Benson |
| 7,860,790 B2 | 12/2010 | Monk |
| 7,865,412 B1 | 1/2011 | Weiss et al. |
| 7,865,557 B2 | 1/2011 | Tomkow |
| 7,865,958 B2 | 1/2011 | Lieblich et al. |
| 7,866,548 B2 | 1/2011 | Reed et al. |
| 7,870,066 B2 | 1/2011 | Lin et al. |
| 7,870,068 B2 | 1/2011 | Chin |
| 7,870,078 B2 | 1/2011 | Clark et al. |
| 7,870,151 B2 | 1/2011 | Mayer et al. |
| 7,870,485 B2 | 1/2011 | Seliutin et al. |
| 7,870,491 B1 | 1/2011 | Henderson et al. |
| 7,873,563 B2 | 1/2011 | Barone et al. |
| 7,873,573 B2 | 1/2011 | Realini |
| 7,873,677 B2 | 1/2011 | Messing et al. |
| 7,877,304 B1 | 1/2011 | Coulter |
| 7,877,402 B1 | 1/2011 | Weiss et al. |
| 7,877,784 B2 | 1/2011 | Chow et al. |
| 7,880,728 B2 | 2/2011 | de los Reyes et al. |
| 7,886,008 B2 | 2/2011 | Tomkow et al. |
| 7,890,403 B1 | 2/2011 | Smith |
| 7,895,139 B2 | 2/2011 | Sullivan et al. |
| 7,895,227 B1 | 2/2011 | Henderson |
| 7,899,750 B1 | 3/2011 | Klieman et al. |
| 7,899,757 B1 | 3/2011 | Talan et al. |
| 7,904,447 B1 | 3/2011 | Russell et al. |
| 7,904,899 B2 | 3/2011 | Robalewski et al. |
| 7,908,242 B1 | 3/2011 | Achanta |
| 7,909,246 B2 | 3/2011 | Hogg et al. |
| 7,911,673 B1 | 3/2011 | Yap |
| 7,912,778 B2 | 3/2011 | Nanjundamoorthy |
| 7,912,842 B1 | 3/2011 | Bayliss et al. |
| 7,912,865 B2 | 3/2011 | Akerman et al. |
| 7,913,173 B2 | 3/2011 | Hebard et al. |
| 7,917,412 B1 | 3/2011 | Wang et al. |
| 7,917,754 B1 | 3/2011 | Harrison et al. |
| 7,925,285 B2 | 4/2011 | Indirabhai |
| 7,925,582 B1 | 4/2011 | Kornegay et al. |
| 7,925,982 B2 | 4/2011 | Parker |
| 7,930,239 B2 | 4/2011 | Pierdinock et al. |
| 7,930,242 B2 | 4/2011 | Morris et al. |
| 7,930,285 B2 | 4/2011 | Abraham et al. |
| 7,930,302 B2 | 4/2011 | Bandaru et al. |
| 7,930,411 B1 | 4/2011 | Hayward |
| 7,933,834 B2 | 4/2011 | Kumar et al. |
| 7,937,325 B2 | 5/2011 | Kumar et al. |
| 7,941,324 B1 | 5/2011 | Sholtis |
| 7,941,560 B1 | 5/2011 | Friesen et al. |
| 7,953,213 B2 | 5/2011 | Babi et al. |
| 7,954,698 B1 | 6/2011 | Pliha |
| 7,958,046 B2 | 6/2011 | Doerner et al. |
| 7,958,126 B2 | 6/2011 | Schachter |
| 7,962,361 B2 | 6/2011 | Ramchandani et al. |
| 7,965,275 B2 | 6/2011 | Lew |
| 7,966,192 B2 | 6/2011 | Pagliari et al. |
| 7,966,325 B2 | 6/2011 | Singh |
| 7,966,372 B1 | 6/2011 | Tomkow |
| 7,970,676 B2 | 6/2011 | Feinstein |
| 7,970,679 B2 | 6/2011 | Kasower |
| 7,970,698 B2 | 6/2011 | Gupta et al. |
| 7,970,701 B2 | 6/2011 | Lewis et al. |
| 7,970,796 B1 | 6/2011 | Narayanan |
| 7,971,141 B1 | 6/2011 | Quinn et al. |
| 7,975,299 B1 | 7/2011 | Balducci et al. |
| 7,979,908 B2 | 7/2011 | Millwee |
| 7,983,932 B2 | 7/2011 | Kane |
| 7,983,979 B2 | 7/2011 | Holland, IV |
| 7,984,436 B1 | 7/2011 | Murray |
| 7,987,173 B2 | 7/2011 | Alexander |
| 7,987,501 B2 | 7/2011 | Miller et al. |
| 7,990,895 B2 | 8/2011 | Ferguson et al. |
| 7,991,673 B2 | 8/2011 | Kumar et al. |
| 7,991,688 B2 | 8/2011 | Phelan et al. |
| 7,991,901 B2 | 8/2011 | Tarquini et al. |
| 7,996,912 B2 | 8/2011 | Spalink et al. |
| 8,001,041 B2 | 8/2011 | Hoadley et al. |
| 8,001,153 B2 | 8/2011 | Skurtovich, Jr. et al. |
| 8,001,235 B2 | 8/2011 | Russ et al. |
| 8,001,582 B2 | 8/2011 | Hulten et al. |
| 8,005,155 B1 | 8/2011 | Lee et al. |
| 8,005,755 B2 | 8/2011 | Freishtat et al. |
| 8,005,759 B2 | 8/2011 | Hirtenstein et al. |
| 8,006,261 B1 | 8/2011 | Haberman et al. |
| 8,010,422 B1 | 8/2011 | Lascelles et al. |
| 8,010,674 B2 | 8/2011 | Fong |
| 8,011,582 B2 | 9/2011 | Ghafarzadeh |
| 8,014,756 B1 | 9/2011 | Henderson |
| 8,015,083 B1 | 9/2011 | Sterling et al. |
| 8,015,107 B2 | 9/2011 | Kornegay et al. |

(56) References Cited

U.S. PATENT DOCUMENTS

| | | |
|---|---|---|
| 8,015,614 B2 | 9/2011 | Matsuzaki et al. |
| 8,019,066 B1 | 9/2011 | Efrati et al. |
| 8,019,843 B2 | 9/2011 | Cash et al. |
| 8,024,264 B2 | 9/2011 | Chaudhuri et al. |
| 8,024,660 B1 | 9/2011 | Quinn et al. |
| 8,024,778 B2 | 9/2011 | Cash et al. |
| 8,027,975 B2 | 9/2011 | Gabriel et al. |
| 8,032,822 B1 | 10/2011 | Artamonov et al. |
| 8,032,930 B2 | 10/2011 | Hicks |
| 8,032,932 B2 | 10/2011 | Speyer et al. |
| 8,036,941 B2 | 10/2011 | Bennett et al. |
| 8,037,097 B2 | 10/2011 | Guo et al. |
| 8,037,115 B1 | 10/2011 | Scalora et al. |
| 8,037,176 B2 | 10/2011 | Hopkins |
| 8,041,127 B2 | 10/2011 | Whitelaw |
| 8,041,956 B1 | 10/2011 | White et al. |
| 8,051,074 B2 | 11/2011 | Eom et al. |
| 8,055,904 B1 | 11/2011 | Cato et al. |
| 8,060,404 B2 | 11/2011 | Storey |
| 8,060,423 B1 | 11/2011 | Rukonic et al. |
| 8,060,424 B2 | 11/2011 | Kasower |
| 8,060,438 B2 | 11/2011 | Dhar et al. |
| 8,060,502 B2 | 11/2011 | Churi et al. |
| 8,060,508 B2 | 11/2011 | Gabriel et al. |
| 8,060,532 B2 | 11/2011 | White et al. |
| 8,060,541 B2 | 11/2011 | Dant |
| 8,060,916 B2 | 11/2011 | Bajaj et al. |
| 8,064,586 B2 | 11/2011 | Shaffer et al. |
| 8,065,175 B1 | 11/2011 | Lewis |
| 8,065,233 B2 | 11/2011 | Lee et al. |
| 8,065,264 B1 | 11/2011 | Achanta |
| 8,065,367 B1 | 11/2011 | Stanley |
| 8,069,213 B2 | 11/2011 | Bloch et al. |
| 8,069,407 B1 | 11/2011 | Armandpour et al. |
| 8,073,785 B1 | 12/2011 | Candella et al. |
| 8,078,453 B2 | 12/2011 | Shaw |
| 8,078,516 B1 | 12/2011 | Weiss et al. |
| 8,078,524 B2 | 12/2011 | Crawford et al. |
| 8,078,527 B2 | 12/2011 | Cerise et al. |
| 8,078,528 B1 | 12/2011 | Vicente et al. |
| 8,078,881 B1 | 12/2011 | Liu |
| 8,078,986 B1 | 12/2011 | Rhyne et al. |
| 8,079,070 B2 | 12/2011 | Camaisa et al. |
| 8,086,508 B2 | 12/2011 | Dheer et al. |
| 8,086,525 B2 | 12/2011 | Atwood et al. |
| 8,090,794 B1 | 1/2012 | Kilat et al. |
| 8,095,443 B2 | 1/2012 | DeBie |
| 8,095,458 B2 | 1/2012 | Peterson et al. |
| 8,095,534 B1 | 1/2012 | Alexander |
| 8,095,614 B2 | 1/2012 | Hopkins |
| 8,098,239 B1 | 1/2012 | Moore |
| 8,099,309 B1 | 1/2012 | Bober |
| 8,099,341 B2 | 1/2012 | Varghese |
| 8,099,356 B2 | 1/2012 | Feinstein et al. |
| 8,099,376 B2 | 1/2012 | Serrano-Morales et al. |
| 8,103,587 B2 | 1/2012 | Kumar et al. |
| 8,104,671 B2 | 1/2012 | Besecker et al. |
| 8,104,679 B2 | 1/2012 | Brown |
| 8,108,301 B2 | 1/2012 | Gupta et al. |
| 8,116,731 B2 | 2/2012 | Buhrmann et al. |
| 8,116,751 B2 | 2/2012 | Aaron |
| 8,117,648 B2 | 2/2012 | Slaton et al. |
| 8,122,133 B2 | 2/2012 | Hopkins |
| 8,126,456 B2 | 2/2012 | Lotter et al. |
| 8,126,820 B1 | 2/2012 | Talan et al. |
| 8,127,982 B1 | 3/2012 | Casey et al. |
| 8,127,986 B1 | 3/2012 | Taylor et al. |
| 8,130,075 B1 | 3/2012 | Hingole |
| 8,131,598 B2 | 3/2012 | Goolkasian et al. |
| 8,131,685 B1 | 3/2012 | Gedalius et al. |
| 8,131,777 B2 | 3/2012 | McCullouch |
| 8,131,846 B1 | 3/2012 | Hernacki et al. |
| 8,140,847 B1 | 3/2012 | Wu |
| 8,144,368 B2 | 3/2012 | Rodriguez et al. |
| 8,145,189 B2 | 3/2012 | Power et al. |
| 8,145,554 B2 | 3/2012 | Kumar et al. |
| 8,150,161 B2 | 4/2012 | Laaser et al. |
| 8,151,327 B2 | 4/2012 | Eisen |
| 8,151,343 B1 | 4/2012 | Wang et al. |
| 8,151,344 B1 | 4/2012 | Channakeshava |
| 8,155,950 B1 | 4/2012 | Bickerstaff |
| 8,156,175 B2 | 4/2012 | Hopkins |
| 8,160,624 B2 | 4/2012 | Kumar et al. |
| 8,160,960 B1 | 4/2012 | Fei et al. |
| 8,161,104 B2 | 4/2012 | Tomkow |
| 8,170,998 B2 | 5/2012 | Churi et al. |
| 8,171,471 B1 | 5/2012 | Daly |
| 8,172,132 B2 | 5/2012 | Love et al. |
| 8,175,889 B1 | 5/2012 | Girulat et al. |
| 8,180,654 B2 | 5/2012 | Berkman et al. |
| 8,185,747 B2 | 5/2012 | Wood et al. |
| 8,190,513 B2 | 5/2012 | Felger |
| 8,190,629 B2 | 5/2012 | Wu et al. |
| 8,190,998 B2 | 5/2012 | Bitterlich |
| 8,194,956 B2 | 6/2012 | Chandler |
| 8,195,549 B2 | 6/2012 | Kasower |
| 8,196,113 B2 | 6/2012 | Miller et al. |
| 8,200,966 B2 | 6/2012 | Grinberg et al. |
| 8,201,257 B1 | 6/2012 | Andres et al. |
| 8,204,812 B2 | 6/2012 | Stewart et al. |
| 8,209,389 B2 | 6/2012 | Tomkow |
| 8,209,659 B2 | 6/2012 | Mathew |
| 8,214,238 B1 | 7/2012 | Fairfield et al. |
| 8,219,473 B2 | 7/2012 | Gardner et al. |
| 8,219,535 B1 | 7/2012 | Kobori et al. |
| 8,219,771 B2 * | 7/2012 | Le Neel ............... G06F 21/6218 711/163 |
| 8,219,822 B2 | 7/2012 | Camaisa et al. |
| 8,224,723 B2 | 7/2012 | Bosch et al. |
| 8,224,747 B2 | 7/2012 | Kumar et al. |
| 8,224,913 B2 | 7/2012 | Tomkow |
| 8,224,974 B1 | 7/2012 | Flora et al. |
| 8,225,270 B2 | 7/2012 | Frasher et al. |
| 8,225,288 B2 | 7/2012 | Miller et al. |
| 8,225,383 B1 | 7/2012 | Channakeshava et al. |
| 8,225,395 B2 | 7/2012 | Atwood et al. |
| 8,229,810 B2 | 7/2012 | Butera et al. |
| 8,229,844 B2 | 7/2012 | Felger |
| 8,229,850 B2 | 7/2012 | Dilip et al. |
| 8,229,911 B2 | 7/2012 | Bennett |
| 8,234,498 B2 | 7/2012 | Britti et al. |
| 8,239,130 B1 | 8/2012 | Upstill et al. |
| 8,239,677 B2 | 8/2012 | Colson |
| 8,239,929 B2 | 8/2012 | Kwan et al. |
| 8,241,369 B2 | 8/2012 | Stevens |
| 8,244,629 B2 | 8/2012 | Lewis et al. |
| 8,244,635 B2 | 8/2012 | Freishtat et al. |
| 8,244,646 B2 | 8/2012 | Johnston et al. |
| 8,244,848 B1 | 8/2012 | Narayanan et al. |
| 8,249,965 B2 | 8/2012 | Tumminaro |
| 8,249,968 B1 | 8/2012 | Oldham et al. |
| 8,255,298 B1 | 8/2012 | Nesladek |
| 8,255,452 B2 | 8/2012 | Piliouras |
| 8,255,868 B1 | 8/2012 | Robalewski |
| 8,255,971 B1 | 8/2012 | Webb et al. |
| 8,255,978 B2 | 8/2012 | Dick |
| 8,256,013 B1 | 8/2012 | Hernacki et al. |
| 8,260,649 B2 | 9/2012 | Ramanujan et al. |
| 8,260,699 B2 | 9/2012 | Smith et al. |
| 8,260,706 B2 | 9/2012 | Freishtat et al. |
| 8,260,805 B1 | 9/2012 | Venu et al. |
| 8,261,204 B2 | 9/2012 | Huynh et al. |
| 8,261,334 B2 | 9/2012 | Hazlehurst et al. |
| 8,261,974 B2 | 9/2012 | Hull |
| 8,266,065 B2 | 9/2012 | Dilip et al. |
| 8,266,168 B2 | 9/2012 | Bayliss |
| 8,266,515 B2 | 9/2012 | Satyavolu |
| 8,271,362 B2 | 9/2012 | Fasching |
| 8,271,378 B2 | 9/2012 | Chaudhuri et al. |
| 8,271,393 B2 | 9/2012 | Twining et al. |
| 8,271,650 B2 | 9/2012 | Alexander |
| 8,271,894 B1 | 9/2012 | Mayers |
| 8,271,899 B1 | 9/2012 | Blackburn et al. |
| 8,271,906 B1 | 9/2012 | Fong |

(56) References Cited

U.S. PATENT DOCUMENTS

| | | |
|---|---|---|
| 8,271,961 B1 | 9/2012 | Chithambaram |
| 8,275,683 B2 | 9/2012 | Wolfson et al. |
| 8,275,845 B2 | 9/2012 | Tomkow |
| 8,280,348 B2 | 10/2012 | Snyder et al. |
| 8,280,723 B1 | 10/2012 | Laaser |
| 8,280,805 B1 | 10/2012 | Abrahams et al. |
| 8,280,879 B2 | 10/2012 | Alexander |
| 8,281,372 B1 | 10/2012 | Vidal |
| 8,285,613 B1 | 10/2012 | Coulter |
| 8,285,640 B2 | 10/2012 | Scipioni |
| 8,285,641 B2 | 10/2012 | Cataline et al. |
| 8,285,656 B1 | 10/2012 | Chang et al. |
| 8,290,835 B2 | 10/2012 | Homer et al. |
| 8,290,840 B2 | 10/2012 | Kasower |
| 8,290,845 B2 | 10/2012 | Leibon et al. |
| 8,290,856 B1 | 10/2012 | Kasower |
| 8,290,941 B2 | 10/2012 | Alexander |
| 8,291,218 B2 | 10/2012 | Garcia et al. |
| 8,291,477 B2 | 10/2012 | Lunt |
| 8,295,898 B2 | 10/2012 | Ashfield et al. |
| 8,296,206 B1 | 10/2012 | Del Favero et al. |
| 8,296,229 B1 | 10/2012 | Yellin et al. |
| 8,296,562 B2 | 10/2012 | Williams et al. |
| 8,302,164 B2 | 10/2012 | Lunt |
| 8,306,255 B1 | 11/2012 | Degnan |
| 8,306,889 B2 | 11/2012 | Leibon et al. |
| 8,306,986 B2 | 11/2012 | Routson et al. |
| 8,311,792 B1 | 11/2012 | Podgorny et al. |
| 8,312,033 B1 | 11/2012 | McMillan |
| 8,315,940 B2 | 11/2012 | Winbom et al. |
| 8,320,944 B1 | 11/2012 | Gibson et al. |
| 8,321,339 B2 | 11/2012 | Imrey et al. |
| 8,321,413 B2 | 11/2012 | Gabriel et al. |
| 8,321,952 B2 | 11/2012 | Spalink et al. |
| 8,324,080 B2 | 12/2012 | Yang et al. |
| 8,326,672 B2 | 12/2012 | Haggerty et al. |
| 8,326,725 B2 | 12/2012 | Elwell et al. |
| 8,327,429 B2 | 12/2012 | Speyer et al. |
| 8,335,741 B2 | 12/2012 | Kornegay et al. |
| 8,340,685 B2 | 12/2012 | Cochran et al. |
| 8,341,545 B2 | 12/2012 | Hebard |
| 8,345,790 B2 | 1/2013 | Sartori et al. |
| 8,346,226 B2 | 1/2013 | Gibson et al. |
| 8,346,615 B2 | 1/2013 | Connors et al. |
| 8,347,364 B2 | 1/2013 | Babi et al. |
| 8,352,564 B1 | 1/2013 | Campise et al. |
| 8,353,027 B2 | 1/2013 | Dennis et al. |
| 8,353,029 B2 | 1/2013 | Morgan et al. |
| 8,355,935 B2 | 1/2013 | Hellman et al. |
| 8,355,967 B2 | 1/2013 | Debie et al. |
| 8,359,210 B1 | 1/2013 | Altinger et al. |
| 8,359,278 B2 | 1/2013 | Domenikos et al. |
| 8,359,393 B2 | 1/2013 | Metzger |
| 8,364,518 B1 | 1/2013 | Blake et al. |
| 8,364,662 B1 | 1/2013 | Moyer et al. |
| 8,364,969 B2 | 1/2013 | King |
| 8,370,340 B1 | 2/2013 | Yu et al. |
| 8,370,371 B1 | 2/2013 | Moncla et al. |
| 8,374,634 B2 | 2/2013 | Dankar et al. |
| 8,374,885 B2 | 2/2013 | Stibel et al. |
| 8,374,973 B2 | 2/2013 | Herbrich et al. |
| 8,375,331 B1 | 2/2013 | Mayers |
| 8,380,590 B1 | 2/2013 | Rukonic et al. |
| 8,380,803 B1 | 2/2013 | Stibel et al. |
| 8,381,120 B2 | 2/2013 | Stibel et al. |
| 8,386,377 B1 | 2/2013 | Xiong et al. |
| 8,386,966 B1 | 2/2013 | Attinasi et al. |
| 8,392,230 B2 | 3/2013 | Stibel et al. |
| 8,392,334 B2 | 3/2013 | Hirtenstein et al. |
| 8,392,969 B1 | 3/2013 | Park et al. |
| 8,396,743 B2 | 3/2013 | Alvin |
| 8,396,747 B2 | 3/2013 | Bachenheimer |
| 8,400,970 B2 | 3/2013 | Bajar et al. |
| 8,401,875 B2 | 3/2013 | Fish et al. |
| 8,402,526 B2 | 3/2013 | Ahn |
| 8,406,736 B2 | 3/2013 | Das et al. |
| 8,407,141 B2 | 3/2013 | Mullen et al. |
| 8,407,194 B1 | 3/2013 | Chaput et al. |
| 8,412,593 B1 | 4/2013 | Song et al. |
| 8,413,239 B2 | 4/2013 | Sutton et al. |
| 8,417,644 B2 | 4/2013 | Ferguson et al. |
| 8,423,285 B2 | 4/2013 | Paterson et al. |
| 8,423,648 B2 | 4/2013 | Ferguson et al. |
| 8,429,073 B2 | 4/2013 | Ferguson et al. |
| 8,432,275 B2 | 4/2013 | Patel et al. |
| 8,433,512 B1 | 4/2013 | Lopatenko et al. |
| 8,433,654 B2 | 4/2013 | Subbarao et al. |
| 8,442,886 B1 | 5/2013 | Haggerty et al. |
| 8,442,910 B2 | 5/2013 | Morris et al. |
| 8,443,202 B2 | 5/2013 | White et al. |
| 8,447,016 B1 | 5/2013 | Kugler et al. |
| 8,453,068 B2 | 5/2013 | Stibel et al. |
| 8,453,218 B2 | 5/2013 | Lan et al. |
| 8,456,293 B1 | 6/2013 | Trundle et al. |
| 8,458,062 B2 | 6/2013 | Dutt et al. |
| 8,458,074 B2 | 6/2013 | Showalter |
| 8,463,595 B1 | 6/2013 | Rehling et al. |
| 8,463,919 B2 | 6/2013 | Tarquini et al. |
| 8,463,939 B1 | 6/2013 | Galvin |
| 8,464,046 B1 | 6/2013 | Kragh |
| 8,464,939 B1 | 6/2013 | Taylor et al. |
| 8,468,028 B2 | 6/2013 | Stibel et al. |
| 8,468,090 B2 | 6/2013 | Lesandro et al. |
| 8,468,198 B2 | 6/2013 | Tomkow |
| 8,468,199 B2 | 6/2013 | Tomkow |
| 8,473,318 B2 | 6/2013 | Nielson et al. |
| 8,473,354 B2 | 6/2013 | Psota et al. |
| 8,478,674 B1 | 7/2013 | Kapczynski et al. |
| 8,478,981 B2 | 7/2013 | Khan et al. |
| 8,484,186 B1 | 7/2013 | Kapczynski et al. |
| 8,484,211 B2 | 7/2013 | Bayliss |
| 8,484,706 B2 | 7/2013 | Tomkow |
| 8,489,480 B2 | 7/2013 | Kassir |
| 8,494,973 B1 | 7/2013 | Dignan et al. |
| 8,495,077 B2 | 7/2013 | Bayliss |
| 8,495,384 B1 | 7/2013 | DeLuccia |
| 8,498,914 B2 | 7/2013 | Hazelhurst |
| 8,498,930 B2 | 7/2013 | Chung et al. |
| 8,498,944 B2 | 7/2013 | Solomon |
| 8,499,348 B1 | 7/2013 | Rubin |
| 8,504,456 B2 | 8/2013 | Griffin et al. |
| 8,504,470 B1 | 8/2013 | Chirehdast |
| 8,504,628 B2 | 8/2013 | Tomkow |
| 8,510,184 B2 | 8/2013 | Imrev et al. |
| 8,510,189 B2 | 8/2013 | Imrey et al. |
| 8,515,828 B1 | 8/2013 | Wolf et al. |
| 8,515,844 B2 | 8/2013 | Kasower |
| 8,515,862 B2 | 8/2013 | Zhang et al. |
| 8,521,628 B1 | 8/2013 | Gowen et al. |
| 8,521,729 B2 | 8/2013 | Churi et al. |
| 8,527,357 B1 | 9/2013 | Ganesan |
| 8,527,417 B2 | 9/2013 | Telle et al. |
| 8,527,596 B2 | 9/2013 | Long et al. |
| 8,527,773 B1 | 9/2013 | Metzger |
| 8,528,078 B2 | 9/2013 | Camaisa et al. |
| 8,533,118 B2 | 9/2013 | Weller et al. |
| 8,533,791 B2 | 9/2013 | Samuelsson et al. |
| 8,538,980 B1 | 9/2013 | MacKenzie |
| 8,539,599 B2 | 9/2013 | Gomez et al. |
| 8,543,498 B2 | 9/2013 | Silbernagel et al. |
| 8,544,091 B2 | 9/2013 | Stibel |
| 8,548,903 B2 | 10/2013 | Becker |
| 8,549,472 B1 | 10/2013 | Tilwani |
| 8,549,590 B1 | 10/2013 | de Villiers Prichard et al. |
| 8,554,584 B2 | 10/2013 | Hargroder |
| 8,555,357 B1 | 10/2013 | Gauvin |
| 8,560,161 B2 | 10/2013 | Kator et al. |
| 8,560,381 B2 | 10/2013 | Green et al. |
| 8,560,434 B2 | 10/2013 | Morris et al. |
| 8,560,436 B2 | 10/2013 | Ingram et al. |
| 8,560,438 B2 | 10/2013 | Hankey et al. |
| 8,560,444 B2 | 10/2013 | Rosenblatt et al. |
| 8,560,447 B1 | 10/2013 | Hinghole et al. |
| 8,566,029 B1 | 10/2013 | Lopatenko et al. |

(56) References Cited

U.S. PATENT DOCUMENTS

| | | |
|---|---|---|
| 8,566,141 B1 | 10/2013 | Nagdev et al. |
| 8,566,187 B2 | 10/2013 | Keld et al. |
| 8,572,083 B1 | 10/2013 | Snell et al. |
| 8,572,391 B2 | 10/2013 | Golan et al. |
| 8,578,036 B1 | 11/2013 | Holfelder et al. |
| 8,578,496 B1 | 11/2013 | Krishnappa |
| 8,583,593 B1 | 11/2013 | Achanta |
| 8,588,748 B2 | 11/2013 | Buhrman et al. |
| 8,589,069 B1 | 11/2013 | Lehman |
| 8,589,208 B2 | 11/2013 | Kruger et al. |
| 8,600,768 B2 | 12/2013 | Stibel et al. |
| 8,600,854 B2 | 12/2013 | Mayr et al. |
| 8,600,886 B2 | 12/2013 | Ramavarjula et al. |
| 8,601,602 B1 | 12/2013 | Zheng |
| 8,606,234 B2 | 12/2013 | Pei et al. |
| 8,606,666 B1 | 12/2013 | Courbage et al. |
| 8,606,694 B2 | 12/2013 | Campbell et al. |
| 8,606,869 B2 | 12/2013 | Stibel et al. |
| 8,620,579 B1 | 12/2013 | Upstill et al. |
| 8,620,942 B1 | 12/2013 | Hoffman et al. |
| 8,626,137 B1 | 1/2014 | Devitt et al. |
| 8,626,618 B2 | 1/2014 | Psota et al. |
| 8,626,637 B1 | 1/2014 | Gooch et al. |
| 8,630,893 B2 | 1/2014 | Stibel et al. |
| 8,630,938 B2 | 1/2014 | Cheng et al. |
| 8,631,242 B2 | 1/2014 | Britti et al. |
| 8,639,616 B1 | 1/2014 | Rolenaitis et al. |
| 8,639,920 B2 | 1/2014 | Stack et al. |
| 8,639,930 B2 | 1/2014 | Stibel et al. |
| 8,645,275 B2 | 2/2014 | Seifert et al. |
| 8,646,051 B2 | 2/2014 | Paden et al. |
| 8,650,189 B2 | 2/2014 | Fertik et al. |
| 8,650,407 B2 | 2/2014 | Britti et al. |
| 8,656,504 B2 | 2/2014 | Lurey et al. |
| 8,660,541 B1 | 2/2014 | Beresniewicz et al. |
| 8,660,919 B2 | 2/2014 | Kasower |
| 8,660,943 B1 | 2/2014 | Chirehdast |
| 8,671,115 B2 | 3/2014 | Skurtovich, Jr. et al. |
| 8,676,684 B2 | 3/2014 | Newman et al. |
| 8,677,129 B2 | 3/2014 | Milana et al. |
| 8,688,543 B2 | 4/2014 | Dominquez |
| 8,689,001 B1 | 4/2014 | Satish |
| 8,689,311 B2 | 4/2014 | Blinn et al. |
| 8,694,390 B2 | 4/2014 | Imrey et al. |
| 8,694,420 B1 | 4/2014 | Oliai |
| 8,694,502 B2 | 4/2014 | Bayliss |
| 8,695,105 B2 | 4/2014 | Mahendrakar et al. |
| 8,701,199 B1 | 4/2014 | Dotan et al. |
| 8,705,718 B2 | 4/2014 | Baniak et al. |
| 8,706,474 B2 | 4/2014 | Blume et al. |
| 8,706,599 B1 | 4/2014 | Koenig et al. |
| 8,706,616 B1 | 4/2014 | Flynn |
| 8,712,789 B2 | 4/2014 | Stibel et al. |
| 8,712,907 B2 | 4/2014 | Stibel et al. |
| 8,713,651 B1 | 4/2014 | Stibel |
| 8,725,605 B1 | 5/2014 | Plunkett |
| 8,725,613 B1 | 5/2014 | Celka et al. |
| 8,732,004 B1 | 5/2014 | Ramos et al. |
| 8,732,803 B2 | 5/2014 | Stibel et al. |
| 8,738,449 B1 | 5/2014 | Cupps et al. |
| 8,738,515 B2 | 5/2014 | Chaudhuri et al. |
| 8,738,516 B1 | 5/2014 | Dean et al. |
| 8,738,934 B2 | 5/2014 | Lurey et al. |
| 8,744,956 B1 | 6/2014 | DiChiara et al. |
| 8,745,698 B1 | 6/2014 | Ashfield et al. |
| 8,751,378 B2 | 6/2014 | Dornhelm et al. |
| 8,751,388 B1 | 6/2014 | Chapa |
| 8,762,053 B1 | 6/2014 | Lehman |
| 8,762,287 B2 | 6/2014 | Morley et al. |
| 8,768,826 B2 | 7/2014 | Imrey et al. |
| 8,768,914 B2 | 7/2014 | Scriffignano et al. |
| 8,769,614 B1 | 7/2014 | Knox et al. |
| 8,775,299 B2 | 7/2014 | Achanta et al. |
| 8,781,877 B2 | 7/2014 | Kruger et al. |
| 8,781,882 B1 | 7/2014 | Arboletti et al. |
| 8,781,951 B2 | 7/2014 | Lewis et al. |
| 8,781,953 B2 | 7/2014 | Kasower |
| 8,781,975 B2 | 7/2014 | Bennett et al. |
| 8,782,154 B2 | 7/2014 | Tomkow |
| 8,782,217 B1 | 7/2014 | Arone et al. |
| 8,782,753 B2 | 7/2014 | Lunt |
| 8,788,701 B1 | 7/2014 | Byrnes et al. |
| 8,793,166 B2 | 7/2014 | Mizhen |
| 8,793,509 B1 | 7/2014 | Nelson et al. |
| 8,793,777 B2 | 7/2014 | Colson |
| 8,800,005 B2 | 8/2014 | Lunt |
| 8,805,805 B1 | 8/2014 | Kobori et al. |
| 8,806,584 B2 | 8/2014 | Lunt |
| 8,818,888 B1 | 8/2014 | Kapczynski et al. |
| 8,819,789 B2 | 8/2014 | Orttung et al. |
| 8,819,793 B2 | 8/2014 | Gottschalk, Jr. |
| 8,825,544 B2 | 9/2014 | Imrey et al. |
| 8,826,371 B2 | 9/2014 | Webb et al. |
| 8,826,393 B2 | 9/2014 | Eisen |
| 8,831,564 B2 | 9/2014 | Ferguson et al. |
| 8,839,394 B2 | 9/2014 | Dennis et al. |
| 8,856,894 B1 | 10/2014 | Dean et al. |
| 8,856,945 B2 | 10/2014 | Carter et al. |
| 8,860,763 B2 | 10/2014 | Privault et al. |
| 8,862,514 B2 | 10/2014 | Eisen |
| 8,862,566 B2 | 10/2014 | Leitner et al. |
| 8,868,914 B2 | 10/2014 | Teppler |
| 8,868,932 B2 | 10/2014 | Lurey et al. |
| D717,332 S | 11/2014 | Nies et al. |
| 8,882,509 B1 | 11/2014 | Nunamaker |
| 8,903,741 B2 | 12/2014 | Imrey et al. |
| 8,930,251 B2 | 1/2015 | DeBie |
| 8,930,263 B1 | 1/2015 | Mahacek et al. |
| 8,931,058 B2 | 1/2015 | DiChiara et al. |
| 8,938,399 B1 | 1/2015 | Herman |
| 8,938,432 B2 | 1/2015 | Rossmark et al. |
| 8,949,981 B1 | 2/2015 | Trollope et al. |
| 8,954,459 B1 | 2/2015 | McMillan et al. |
| 8,965,934 B2 | 2/2015 | Prieditis |
| 8,966,649 B2 | 2/2015 | Stack et al. |
| 8,972,400 B1 | 3/2015 | Kapczynski et al. |
| 9,002,753 B2 | 4/2015 | Anschutz et al. |
| 9,010,627 B1 | 4/2015 | Prasad et al. |
| 9,043,886 B2 | 5/2015 | Srinivasan et al. |
| 9,047,473 B2 | 6/2015 | Samuelsson et al. |
| 9,057,616 B1 | 6/2015 | Lopatenko et al. |
| 9,057,617 B1 | 6/2015 | Lopatenko et al. |
| 9,058,627 B1 | 6/2015 | Wasser et al. |
| 9,075,848 B2 | 7/2015 | Churi et al. |
| 9,100,400 B2 | 8/2015 | Lunt |
| 9,106,691 B1 | 8/2015 | Burger et al. |
| 9,116,918 B1 | 8/2015 | Kim |
| 9,118,614 B1 | 8/2015 | Rogers et al. |
| 9,124,606 B2 | 9/2015 | Metzger |
| 9,143,541 B1 | 9/2015 | Szamonek et al. |
| 9,147,042 B1 | 9/2015 | Haller et al. |
| 9,147,117 B1 | 9/2015 | Madhu et al. |
| 9,152,727 B1 | 10/2015 | Balducci et al. |
| 9,154,482 B2 | 10/2015 | Dudziak et al. |
| 9,158,903 B2 | 10/2015 | Metzger |
| 9,165,044 B2 | 10/2015 | Psenka et al. |
| 9,218,481 B2 | 10/2015 | Belisario |
| 9,183,377 B1 | 11/2015 | Sobel et al. |
| 9,185,123 B2 | 11/2015 | Dennis et al. |
| 9,195,984 B1 | 11/2015 | Spector et al. |
| 9,195,985 B2 | 11/2015 | Domenica et al. |
| 9,196,004 B2 | 11/2015 | Eisen |
| 9,202,200 B2 | 12/2015 | Stibel et al. |
| 9,203,819 B2 | 12/2015 | Fenton et al. |
| 9,215,223 B2 | 12/2015 | Kirsch |
| 9,225,704 B1 | 12/2015 | Johansson et al. |
| 9,230,283 B1 | 1/2016 | Taylor et al. |
| 9,235,728 B2 | 1/2016 | Gottschalk, Jr. et al. |
| 9,246,899 B1 | 1/2016 | Durney et al. |
| 9,256,624 B2 | 2/2016 | Skurtovich, Jr. et al. |
| 9,256,904 B1 | 2/2016 | Haller et al. |
| 9,268,803 B2 | 2/2016 | Kapochunas et al. |
| 9,269,085 B2 | 2/2016 | Webb et al. |
| 9,294,476 B1 | 3/2016 | Lurey et al. |

(56) References Cited

U.S. PATENT DOCUMENTS

| | | |
|---|---|---|
| 9,305,300 B2 | 4/2016 | Mulhern et al. |
| 9,324,080 B2 | 4/2016 | Shafron et al. |
| 9,324,087 B2 | 4/2016 | Routson et al. |
| 9,342,783 B1 | 5/2016 | Chang et al. |
| 9,344,413 B2 | 5/2016 | Kirsch |
| 9,349,145 B2 | 5/2016 | Rozman et al. |
| 9,361,597 B2 | 6/2016 | Britton et al. |
| 9,380,057 B2 | 6/2016 | Knauss |
| 9,390,384 B2 | 7/2016 | Eisen |
| 9,391,971 B2 | 7/2016 | Lunt |
| 9,400,589 B1 | 7/2016 | Wasser et al. |
| 9,406,085 B1 | 8/2016 | Hunt, III et al. |
| 9,412,141 B2 | 8/2016 | Prichard et al. |
| 9,418,213 B1 | 8/2016 | Roth et al. |
| 9,420,448 B2 | 8/2016 | Dankar et al. |
| 9,438,570 B2 | 9/2016 | Milana et al. |
| 9,443,268 B1 | 9/2016 | Kapczynski et al. |
| 9,449,346 B1 | 9/2016 | Hockey et al. |
| 9,462,044 B1 | 10/2016 | Preibisch et al. |
| 9,465,786 B2 | 10/2016 | Lurey et al. |
| 9,467,445 B2 | 10/2016 | Egan et al. |
| 9,477,737 B1 | 10/2016 | Charyk et al. |
| 9,479,471 B2 | 10/2016 | Schoenrock |
| 9,483,606 B1 | 11/2016 | Dean et al. |
| 9,491,160 B2 | 11/2016 | Livesay et al. |
| 9,501,583 B2 | 11/2016 | Nordstrom et al. |
| 9,529,851 B1 | 12/2016 | Smith |
| 9,535,959 B2 | 1/2017 | Sun et al. |
| 9,536,238 B2 | 1/2017 | Garrett et al. |
| 9,536,263 B1 | 1/2017 | Dean et al. |
| 9,542,553 B1 | 1/2017 | Burger et al. |
| 9,542,682 B1 | 1/2017 | Taylor et al. |
| 9,553,936 B2 | 1/2017 | Dijk et al. |
| 9,569,797 B1 | 2/2017 | Rohn et al. |
| 9,578,014 B2 | 2/2017 | Sondhi et al. |
| 9,589,266 B2 | 3/2017 | Pourgallah et al. |
| 9,595,023 B1 | 3/2017 | Hockey et al. |
| 9,595,051 B2 | 3/2017 | Stack et al. |
| 9,600,651 B1 | 3/2017 | Ryan et al. |
| 9,607,336 B1 | 3/2017 | Dean et al. |
| 9,613,382 B1 | 4/2017 | Newstadt et al. |
| 9,619,751 B2 | 4/2017 | Woon et al. |
| 9,626,680 B1 | 4/2017 | Ryan et al. |
| 9,633,322 B1 | 4/2017 | Burger |
| 9,636,053 B2 | 5/2017 | Peterson et al. |
| 9,641,521 B2 | 5/2017 | Egan et al. |
| 9,646,058 B2 | 5/2017 | Churi et al. |
| 9,654,541 B1 | 5/2017 | Kapczynski et al. |
| 9,665,854 B1 | 5/2017 | Burger et al. |
| 9,684,905 B1 | 6/2017 | Haller et al. |
| 9,697,521 B2 | 7/2017 | Webb et al. |
| 9,697,568 B1 | 7/2017 | Hunt, III |
| 9,704,107 B1 | 7/2017 | Baker, IV et al. |
| 9,705,863 B2 | 7/2017 | Britti et al. |
| 9,706,402 B2 | 7/2017 | Kueh |
| 9,710,523 B2 | 7/2017 | Skurtovich, Jr. et al. |
| 9,710,852 B1 | 7/2017 | Olson et al. |
| 9,721,147 B1 | 8/2017 | Kapczynski |
| 9,734,501 B2 | 8/2017 | Durney et al. |
| 9,754,256 B2 | 9/2017 | Britton et al. |
| 9,754,311 B2 | 9/2017 | Eisen |
| 9,760,885 B1 | 9/2017 | Ramalingam et al. |
| 9,767,513 B1 | 9/2017 | Taylor et al. |
| 9,774,681 B2 | 9/2017 | Zoldi et al. |
| 9,779,392 B1 | 10/2017 | Prasad et al. |
| 9,818,121 B2 | 11/2017 | Snyder et al. |
| 9,830,646 B1 | 11/2017 | Wasser et al. |
| 9,843,582 B2 | 12/2017 | Mahendrakar et al. |
| 9,853,959 B1 | 12/2017 | Kapczynski et al. |
| 9,866,561 B2 | 1/2018 | Psenka et al. |
| 9,870,589 B1 | 1/2018 | Arnold et al. |
| 9,876,796 B2 | 1/2018 | Egan et al. |
| 9,892,389 B2 | 2/2018 | Domenica et al. |
| 9,892,457 B1 | 2/2018 | Kapczynski |
| 9,916,621 B1 | 3/2018 | Wasser et al. |
| 9,955,003 B2 | 4/2018 | Cody et al. |
| 9,972,048 B1 | 5/2018 | Dean et al. |
| 9,989,501 B2 | 6/2018 | Tat et al. |
| 9,990,674 B1 | 6/2018 | Taylor et al. |
| 10,002,075 B1 | 6/2018 | O'Leary et al. |
| 10,003,591 B2 | 6/2018 | Hockey et al. |
| 10,025,842 B1 | 7/2018 | Charyk et al. |
| 10,043,214 B1 | 8/2018 | Hunt, III |
| 10,061,936 B1 | 8/2018 | Burger et al. |
| 10,075,446 B2 | 9/2018 | McMillan et al. |
| 10,089,679 B2 | 10/2018 | Eisen |
| 10,097,551 B2 | 10/2018 | Chan et al. |
| 10,102,536 B1 | 10/2018 | Hickman et al. |
| 10,102,570 B1 | 10/2018 | Kapczynski et al. |
| 10,104,059 B2 | 10/2018 | Hockey et al. |
| 10,108,818 B2 | 10/2018 | Curcio et al. |
| 10,115,079 B1 | 10/2018 | Burger et al. |
| 10,115,102 B2 | 10/2018 | Burrell et al. |
| 10,117,609 B2 | 11/2018 | Peterson et al. |
| 10,169,761 B1 | 1/2019 | Burger |
| 10,176,233 B1 | 1/2019 | Dean et al. |
| 10,180,861 B2 | 1/2019 | Raghavan et al. |
| 10,187,341 B2 | 1/2019 | Schoenrock |
| 10,255,598 B1 | 4/2019 | Dean et al. |
| 10,262,362 B1 | 4/2019 | Hu et al. |
| 10,262,364 B2 | 4/2019 | Taylor et al. |
| 10,269,065 B1 | 4/2019 | Kapczynski et al. |
| 10,277,659 B1 | 4/2019 | Kapczynski et al. |
| D847,840 S | 5/2019 | Poschel et al. |
| 10,282,790 B1 | 5/2019 | Kolbrener et al. |
| 10,284,548 B2 | 5/2019 | Williams et al. |
| D851,126 S | 6/2019 | Tauban |
| D851,127 S | 6/2019 | Tauban |
| D851,128 S | 6/2019 | Tauban |
| 10,319,029 B1 | 6/2019 | Hockey et al. |
| 10,325,314 B1 | 6/2019 | Kapczynski et al. |
| 10,339,330 B2 | 7/2019 | Riley et al. |
| 10,356,079 B2 | 7/2019 | Lurey et al. |
| 10,366,450 B1 | 7/2019 | Mahacek et al. |
| 10,367,888 B2 | 7/2019 | Zoldi et al. |
| 10,373,240 B1 | 8/2019 | Ross et al. |
| 10,380,565 B1 | 8/2019 | Prasad |
| 10,380,654 B2 | 8/2019 | Hirtenstein et al. |
| 10,395,053 B2 | 8/2019 | Samid |
| 10,437,895 B2 | 10/2019 | Chang et al. |
| 10,438,308 B2 | 10/2019 | Prichard et al. |
| 10,453,159 B2 | 10/2019 | Kapczynski |
| 10,482,532 B1 | 11/2019 | Kapczynski |
| 10,503,798 B2 | 12/2019 | Chen et al. |
| 10,515,084 B2 | 12/2019 | Sun et al. |
| 10,523,653 B2 | 12/2019 | Hockey et al. |
| 10,530,761 B2 | 1/2020 | Hockey et al. |
| 10,547,739 B2 | 1/2020 | Cody et al. |
| 10,580,025 B2 | 3/2020 | Hickman et al. |
| 10,580,724 B2 | 3/2020 | Britti et al. |
| 10,614,463 B1 | 4/2020 | Hockey et al. |
| 10,614,519 B2 | 4/2020 | Taylor et al. |
| 10,616,196 B1 | 4/2020 | Khitrenovich et al. |
| 10,621,657 B2 | 4/2020 | Kasower |
| 10,628,448 B1 | 4/2020 | Charyk et al. |
| 10,637,646 B2 | 4/2020 | Krishnamacharya et al. |
| 10,642,999 B2 | 5/2020 | Burger et al. |
| 10,652,227 B2 | 5/2020 | Spektor et al. |
| 10,664,936 B2 | 5/2020 | Chapa et al. |
| 10,671,749 B2 | 6/2020 | Felice-Steele et al. |
| 10,685,336 B1 | 6/2020 | Burger et al. |
| 10,685,398 B1 | 6/2020 | Olson et al. |
| 10,686,773 B2 | 6/2020 | Britti et al. |
| 10,691,825 B2 | 6/2020 | Jones et al. |
| 10,693,840 B2 | 6/2020 | Peterson et al. |
| 10,706,453 B1 | 7/2020 | Morin et al. |
| 10,719,873 B1 | 7/2020 | Dean et al. |
| 10,726,491 B1 | 7/2020 | Hockey et al. |
| 10,740,762 B2 | 8/2020 | Burger |
| 10,771,463 B2 | 9/2020 | Berezin et al. |
| 10,783,542 B2 | 9/2020 | Walz et al. |
| 10,798,093 B2 | 10/2020 | Kaliski, Jr. et al. |
| 10,798,096 B2 | 10/2020 | Touati et al. |
| 10,798,197 B2 | 10/2020 | Dean et al. |

(56) References Cited

U.S. PATENT DOCUMENTS

| | | |
|---|---|---|
| 10,810,218 B2 | 10/2020 | Ng et al. |
| 10,839,446 B1 | 11/2020 | Mupkala et al. |
| 10,863,359 B2 | 12/2020 | Talwar |
| 10,878,499 B2 | 12/2020 | Taylor et al. |
| 10,880,313 B2 | 12/2020 | Manna et al. |
| 10,885,139 B2 | 1/2021 | Chen et al. |
| 10,887,457 B1 | 1/2021 | Degeorgis et al. |
| 10,891,618 B2 | 1/2021 | Kinch et al. |
| 10,891,691 B2 | 1/2021 | Courbage et al. |
| 10,911,234 B2 | 2/2021 | Jain et al. |
| 10,929,925 B1 | 2/2021 | Hunt, III |
| 10,949,428 B2 | 3/2021 | Poirel et al. |
| 10,963,434 B1 | 3/2021 | Rodriguez et al. |
| 10,963,959 B2 | 3/2021 | Wasser et al. |
| 10,979,560 B2 | 4/2021 | Cody et al. |
| 10,999,298 B2 | 5/2021 | Eisen |
| 11,012,240 B1 | 5/2021 | Kirsch |
| 11,012,491 B1 | 5/2021 | Kapczynski et al. |
| 11,025,629 B2 | 6/2021 | Chasman et al. |
| 11,025,638 B2 | 6/2021 | Ford et al. |
| 11,042,662 B2 | 6/2021 | Riley et al. |
| 11,050,767 B2 | 6/2021 | Black et al. |
| 11,074,641 B1 | 7/2021 | Ross et al. |
| 11,087,022 B2 | 8/2021 | Burger et al. |
| 11,095,643 B2 | 8/2021 | Huffman et al. |
| 11,107,158 B1 | 8/2021 | Hu et al. |
| 11,113,759 B1 | 9/2021 | Kapczynski et al. |
| 11,120,519 B2 | 9/2021 | Kapczynski |
| 11,132,742 B1 | 9/2021 | Wasser et al. |
| 11,146,676 B2 | 10/2021 | Sena, Jr. et al. |
| 11,157,872 B2 | 10/2021 | McMillan et al. |
| 11,163,943 B2 | 11/2021 | Billman et al. |
| 11,164,178 B2 | 11/2021 | Anderson et al. |
| 11,164,271 B2 | 11/2021 | Chapa et al. |
| 11,178,128 B2 | 11/2021 | Poschel et al. |
| 11,200,620 B2 | 12/2021 | Dean et al. |
| 11,206,246 B2 | 12/2021 | Krishnamacharya |
| 11,227,001 B2 | 1/2022 | Rege et al. |
| 11,232,413 B1 | 1/2022 | Burger et al. |
| 11,238,656 B1 | 2/2022 | Lin et al. |
| 11,263,218 B2 | 3/2022 | Pieniazek et al. |
| 11,265,324 B2 | 3/2022 | Felice-Steele et al. |
| 11,270,275 B2 | 3/2022 | Anderson et al. |
| 11,277,439 B2 | 3/2022 | Knopf |
| 11,288,677 B1 | 3/2022 | Burger |
| 11,290,255 B2 | 3/2022 | Krishnamacharya et al. |
| 11,308,170 B2 | 4/2022 | Chang et al. |
| 11,308,551 B1 | 4/2022 | Mahacek et al. |
| 11,315,179 B1 | 4/2022 | Rehder et al. |
| 11,328,083 B2 | 5/2022 | Jones et al. |
| 11,356,430 B1 | 6/2022 | Kapczynski et al. |
| 11,356,460 B2 | 6/2022 | Bondugula et al. |
| 11,361,317 B2 | 6/2022 | Billman et al. |
| 11,373,109 B2 | 6/2022 | Zoldi et al. |
| 11,379,916 B1 | 7/2022 | Taylor et al. |
| 11,399,029 B2 | 7/2022 | Manna et al. |
| 11,425,144 B2 | 8/2022 | Bondugula et al. |
| 11,431,729 B2 | 8/2022 | Bloomquist et al. |
| 11,436,626 B2 | 9/2022 | Lawrence et al. |
| 11,443,316 B2 | 9/2022 | Burrell et al. |
| 11,449,630 B2 | 9/2022 | Talwar |
| 11,461,383 B2 | 10/2022 | Xie et al. |
| 11,468,186 B2 | 10/2022 | Dong et al. |
| 2001/0000536 A1 | 4/2001 | Tarin |
| 2001/0011245 A1 | 8/2001 | Duhon |
| 2001/0014878 A1 | 8/2001 | Mitra et al. |
| 2001/0029470 A1 | 10/2001 | Schultz et al. |
| 2001/0029482 A1 | 10/2001 | Tealdi et al. |
| 2001/0032181 A1 | 10/2001 | Jakstadt et al. |
| 2001/0034631 A1 | 10/2001 | Kiselik |
| 2001/0037204 A1 | 11/2001 | Horn et al. |
| 2001/0037289 A1 | 11/2001 | Mayr et al. |
| 2001/0037332 A1 | 11/2001 | Miller et al. |
| 2001/0039532 A1 | 11/2001 | Coleman, Jr. et al. |
| 2001/0039563 A1 | 11/2001 | Tian |
| 2001/0042785 A1 | 11/2001 | Walker et al. |
| 2001/0044729 A1 | 11/2001 | Pomerance |
| 2001/0044756 A1 | 11/2001 | Watkins et al. |
| 2001/0044764 A1 | 11/2001 | Arnold |
| 2001/0047332 A1 | 11/2001 | Gonen-Friedman et al. |
| 2001/0049274 A1 | 12/2001 | Degraeve |
| 2001/0049620 A1 | 12/2001 | Blasko |
| 2001/0053989 A1 | 12/2001 | Keller et al. |
| 2002/0004736 A1 | 1/2002 | Roundtree et al. |
| 2002/0010616 A1 | 1/2002 | Itzaki |
| 2002/0010635 A1 | 1/2002 | Tokiwa |
| 2002/0010664 A1 | 1/2002 | Rabideau et al. |
| 2002/0010701 A1 | 1/2002 | Kosciuszko |
| 2002/0013827 A1 | 1/2002 | Edstrom et al. |
| 2002/0013899 A1 | 1/2002 | Faul |
| 2002/0023108 A1 | 2/2002 | Daswani et al. |
| 2002/0026507 A1 | 2/2002 | Sears et al. |
| 2002/0026519 A1 | 2/2002 | Itabashi et al. |
| 2002/0029192 A1 | 3/2002 | Nakagawa et al. |
| 2002/0032635 A1 | 3/2002 | Harris et al. |
| 2002/0033846 A1 | 3/2002 | Balasubramanian et al. |
| 2002/0035480 A1 | 3/2002 | Gordon et al. |
| 2002/0035520 A1 | 3/2002 | Weiss |
| 2002/0045154 A1 | 4/2002 | Wood et al. |
| 2002/0049624 A1 | 4/2002 | Ravels, Jr. |
| 2002/0049701 A1 | 4/2002 | Nabe et al. |
| 2002/0049738 A1 | 4/2002 | Epstein |
| 2002/0052754 A1 | 5/2002 | Joyce et al. |
| 2002/0052841 A1 | 5/2002 | Guthrie et al. |
| 2002/0052884 A1 | 5/2002 | Farber et al. |
| 2002/0055906 A1 | 5/2002 | Katz et al. |
| 2002/0059139 A1 | 5/2002 | Evans |
| 2002/0059201 A1 | 5/2002 | Work |
| 2002/0059521 A1 | 5/2002 | Tasler |
| 2002/0062249 A1 | 5/2002 | Iannacci |
| 2002/0069122 A1 | 6/2002 | Yun et al. |
| 2002/0069182 A1 | 6/2002 | Dwyer |
| 2002/0073017 A1 | 6/2002 | Robertson |
| 2002/0077964 A1 | 6/2002 | Brody et al. |
| 2002/0087460 A1 | 7/2002 | Hornung |
| 2002/0091544 A1 | 7/2002 | Middeljans et al. |
| 2002/0091635 A1 | 7/2002 | Dilip et al. |
| 2002/0091650 A1 | 7/2002 | Ellis |
| 2002/0091706 A1 | 7/2002 | Anderson et al. |
| 2002/0099628 A1 | 7/2002 | Takaoka et al. |
| 2002/0099635 A1 | 7/2002 | Guiragosian |
| 2002/0099824 A1 | 7/2002 | Bender et al. |
| 2002/0099936 A1 | 7/2002 | Kou et al. |
| 2002/0103809 A1 | 8/2002 | Starzl et al. |
| 2002/0103933 A1 | 8/2002 | Garon et al. |
| 2002/0107957 A1 | 8/2002 | Zargham et al. |
| 2002/0111816 A1 | 8/2002 | Lortscher et al. |
| 2002/0111890 A1 | 8/2002 | Sloan et al. |
| 2002/0111910 A1 | 8/2002 | Walsh |
| 2002/0116247 A1 | 8/2002 | Tucker et al. |
| 2002/0116331 A1 | 8/2002 | Cataline et al. |
| 2002/0120537 A1 | 8/2002 | Morea et al. |
| 2002/0120757 A1 | 8/2002 | Sutherland et al. |
| 2002/0120846 A1 | 8/2002 | Stewart et al. |
| 2002/0126449 A1 | 9/2002 | Casebolt |
| 2002/0128917 A1 | 9/2002 | Grounds |
| 2002/0128962 A1 | 9/2002 | Kasower |
| 2002/0130894 A1 | 9/2002 | Young et al. |
| 2002/0131565 A1 | 9/2002 | Scheuring et al. |
| 2002/0133365 A1 | 9/2002 | Grey et al. |
| 2002/0133462 A1 | 9/2002 | Shteyn |
| 2002/0133504 A1 | 9/2002 | Vlahos et al. |
| 2002/0138297 A1 | 9/2002 | Lee |
| 2002/0138409 A1 | 9/2002 | Bass |
| 2002/0138470 A1 | 9/2002 | Zhou |
| 2002/0143943 A1 | 10/2002 | Lee et al. |
| 2002/0147801 A1 | 10/2002 | Gullotta et al. |
| 2002/0149794 A1 | 10/2002 | Yoshioka et al. |
| 2002/0152166 A1 | 10/2002 | Dutta et al. |
| 2002/0156676 A1 | 10/2002 | Ahrens et al. |
| 2002/0157029 A1 | 10/2002 | French et al. |
| 2002/0161496 A1 | 10/2002 | Yamaki |
| 2002/0161664 A1 | 10/2002 | Shaya et al. |
| 2002/0165757 A1 | 11/2002 | Lisser |

(56) References Cited

U.S. PATENT DOCUMENTS

| | | |
|---|---|---|
| 2002/0169747 A1 | 11/2002 | Chapman et al. |
| 2002/0173984 A1 | 11/2002 | Robertson et al. |
| 2002/0173994 A1 | 11/2002 | Ferguson, III |
| 2002/0174010 A1 | 11/2002 | Rice |
| 2002/0174016 A1 | 11/2002 | Cuervo |
| 2002/0174048 A1 | 11/2002 | Dheer et al. |
| 2002/0174061 A1 | 11/2002 | Srinivasan et al. |
| 2002/0184255 A1 | 12/2002 | Edd et al. |
| 2002/0184509 A1 | 12/2002 | Scheldt et al. |
| 2002/0188511 A1 | 12/2002 | Johnson et al. |
| 2002/0188544 A1 | 12/2002 | Wizon et al. |
| 2002/0194120 A1 | 12/2002 | Russell et al. |
| 2002/0194140 A1 | 12/2002 | Makuck |
| 2002/0198800 A1 | 12/2002 | Shamrakov |
| 2002/0198806 A1 | 12/2002 | Blagg et al. |
| 2002/0198822 A1 | 12/2002 | Munoz et al. |
| 2002/0198824 A1 | 12/2002 | Cook |
| 2002/0198830 A1 | 12/2002 | Randell et al. |
| 2003/0002671 A1 | 1/2003 | Inchalik et al. |
| 2003/0004853 A1 | 1/2003 | Ram et al. |
| 2003/0004855 A1 | 1/2003 | Dutta et al. |
| 2003/0004922 A1 | 1/2003 | Schmidt et al. |
| 2003/0007283 A1 | 1/2003 | Ostwald et al. |
| 2003/0009411 A1 | 1/2003 | Ram et al. |
| 2003/0009415 A1 | 1/2003 | Lutnick et al. |
| 2003/0009418 A1 | 1/2003 | Green et al. |
| 2003/0009426 A1 | 1/2003 | Ruiz-Sanchez |
| 2003/0018549 A1 | 1/2003 | Fei et al. |
| 2003/0018578 A1 | 1/2003 | Schultz |
| 2003/0023531 A1 | 1/2003 | Fergusson |
| 2003/0028466 A1 | 2/2003 | Jenson et al. |
| 2003/0028477 A1 | 2/2003 | Stevenson et al. |
| 2003/0028529 A1 | 2/2003 | Cheung |
| 2003/0036952 A1 | 2/2003 | Panttaja et al. |
| 2003/0036995 A1 | 2/2003 | Lazerson |
| 2003/0041019 A1 | 2/2003 | Vagim, III et al. |
| 2003/0041031 A1 | 2/2003 | Hedy |
| 2003/0041050 A1 | 2/2003 | Smith et al. |
| 2003/0046311 A1 | 3/2003 | Baidya et al. |
| 2003/0046554 A1 | 3/2003 | Leydier et al. |
| 2003/0048294 A1 | 3/2003 | Arnold |
| 2003/0048904 A1 | 3/2003 | Wang et al. |
| 2003/0050882 A1 | 3/2003 | Degen et al. |
| 2003/0050929 A1 | 3/2003 | Bookman et al. |
| 2003/0055931 A1 | 3/2003 | Cravo De Almeida et al. |
| 2003/0061104 A1 | 3/2003 | Thomson et al. |
| 2003/0061155 A1 | 3/2003 | Chin |
| 2003/0061163 A1 | 3/2003 | Durfield |
| 2003/0069839 A1 | 4/2003 | Whittington et al. |
| 2003/0069943 A1 | 4/2003 | Bahrs et al. |
| 2003/0078897 A1 | 4/2003 | Florance et al. |
| 2003/0078926 A1 | 4/2003 | Uthe et al. |
| 2003/0088472 A1 | 5/2003 | Offutt et al. |
| 2003/0090586 A1 | 5/2003 | Jan et al. |
| 2003/0093289 A1 | 5/2003 | Thornley et al. |
| 2003/0093311 A1 | 5/2003 | Knowlson |
| 2003/0097342 A1 | 5/2003 | Whittingtom |
| 2003/0097380 A1 | 5/2003 | Mulhern et al. |
| 2003/0101111 A1 | 5/2003 | Dang et al. |
| 2003/0101344 A1 | 5/2003 | Wheeler et al. |
| 2003/0105646 A1 | 6/2003 | Siepser |
| 2003/0105710 A1 | 6/2003 | Barbara et al. |
| 2003/0105728 A1 | 6/2003 | Yano et al. |
| 2003/0105733 A1 | 6/2003 | Boreham |
| 2003/0105742 A1 | 6/2003 | Boreham et al. |
| 2003/0110255 A1 | 6/2003 | Tarquini et al. |
| 2003/0115133 A1 | 6/2003 | Bian |
| 2003/0131102 A1 | 7/2003 | Umbreit |
| 2003/0135451 A1 | 7/2003 | O'Brien et al. |
| 2003/0153299 A1 | 8/2003 | Perfit et al. |
| 2003/0154162 A1 | 8/2003 | Danaher et al. |
| 2003/0158749 A1 | 8/2003 | Olchanski et al. |
| 2003/0158776 A1 | 8/2003 | Landesmann |
| 2003/0158960 A1 | 8/2003 | Engberg |
| 2003/0163435 A1 | 8/2003 | Payone |
| 2003/0163513 A1 | 8/2003 | Schaeck et al. |
| 2003/0163733 A1 | 8/2003 | Barriga-Caceres et al. |
| 2003/0171942 A1 | 9/2003 | Gaito |
| 2003/0177028 A1 | 9/2003 | Cooper et al. |
| 2003/0182214 A1 | 9/2003 | Taylor |
| 2003/0186200 A1 | 10/2003 | Selix |
| 2003/0187768 A1 | 10/2003 | Ryan et al. |
| 2003/0187837 A1 | 10/2003 | Culliss |
| 2003/0188193 A1 | 10/2003 | Venkataramappa |
| 2003/0191711 A1 | 10/2003 | Jamison et al. |
| 2003/0191731 A1 | 10/2003 | Stewart et al. |
| 2003/0195805 A1 | 10/2003 | Storey |
| 2003/0195859 A1 | 10/2003 | Lawrence |
| 2003/0200142 A1 | 10/2003 | Hicks et al. |
| 2003/0200151 A1 | 10/2003 | Ellenson et al. |
| 2003/0200447 A1 | 10/2003 | Sjoblom |
| 2003/0204429 A1 | 10/2003 | Botscheck et al. |
| 2003/0204752 A1 | 10/2003 | Garrison |
| 2003/0208412 A1 | 11/2003 | Hillestad et al. |
| 2003/0212654 A1 | 11/2003 | Harper et al. |
| 2003/0212745 A1 | 11/2003 | Caughey |
| 2003/0212909 A1 | 11/2003 | Rashekhar |
| 2003/0214775 A1 | 11/2003 | Fukuta et al. |
| 2003/0219709 A1 | 11/2003 | Olenick et al. |
| 2003/0220858 A1 | 11/2003 | Lam et al. |
| 2003/0225742 A1 | 12/2003 | Tenner et al. |
| 2003/0229504 A1 | 12/2003 | Hollister |
| 2003/0229580 A1 | 12/2003 | Gass et al. |
| 2003/0229892 A1 | 12/2003 | Sardera |
| 2003/0233292 A1 | 12/2003 | Richey et al. |
| 2003/0236701 A1 | 12/2003 | Rowney et al. |
| 2004/0001565 A1 | 1/2004 | Jones et al. |
| 2004/0002878 A1 | 1/2004 | Hinton |
| 2004/0006488 A1 | 1/2004 | Fitall et al. |
| 2004/0006536 A1 | 1/2004 | Kawashima et al. |
| 2004/0010458 A1 | 1/2004 | Friedman |
| 2004/0010698 A1 | 1/2004 | Rolfe |
| 2004/0015714 A1 | 1/2004 | Abraham et al. |
| 2004/0015715 A1 | 1/2004 | Brown |
| 2004/0019518 A1 | 1/2004 | Abraham et al. |
| 2004/0019549 A1 | 1/2004 | Gulbrandsen |
| 2004/0019799 A1 | 1/2004 | Vering et al. |
| 2004/0024671 A1 | 2/2004 | Freund |
| 2004/0024709 A1 | 2/2004 | Yu et al. |
| 2004/0030574 A1 | 2/2004 | DiCostanzo et al. |
| 2004/0030649 A1 | 2/2004 | Nelson et al. |
| 2004/0039586 A1 | 2/2004 | Garvey et al. |
| 2004/0044563 A1 | 3/2004 | Stein |
| 2004/0044601 A1 | 3/2004 | Kim et al. |
| 2004/0044628 A1 | 3/2004 | Mathew et al. |
| 2004/0044673 A1 | 3/2004 | Brady et al. |
| 2004/0044739 A1 | 3/2004 | Ziegler |
| 2004/0045028 A1 | 3/2004 | Harris |
| 2004/0046033 A1 | 3/2004 | Kolodziej et al. |
| 2004/0052357 A1 | 3/2004 | Logan et al. |
| 2004/0059786 A1 | 3/2004 | Caughey |
| 2004/0062213 A1 | 4/2004 | Koss |
| 2004/0078324 A1 | 4/2004 | Lonnberg et al. |
| 2004/0083159 A1 | 4/2004 | Crosby et al. |
| 2004/0083215 A1 | 4/2004 | de Jong |
| 2004/0083230 A1 | 4/2004 | Caughey |
| 2004/0083482 A1 | 4/2004 | Makagon et al. |
| 2004/0088237 A1 | 5/2004 | Moenickheim et al. |
| 2004/0088255 A1 | 5/2004 | Zielke et al. |
| 2004/0093278 A1 | 5/2004 | Burchetta et al. |
| 2004/0098418 A1 | 5/2004 | Hein |
| 2004/0098546 A1 | 5/2004 | Bashant et al. |
| 2004/0098625 A1 | 5/2004 | Lagadec et al. |
| 2004/0102197 A1 | 5/2004 | Dietz |
| 2004/0103147 A1 | 5/2004 | Flesher et al. |
| 2004/0107250 A1 | 6/2004 | Marciano |
| 2004/0110119 A1 | 6/2004 | Riconda et al. |
| 2004/0111359 A1 | 6/2004 | Hudock |
| 2004/0111375 A1 | 6/2004 | Johnson |
| 2004/0117302 A1 | 6/2004 | Weichert et al. |
| 2004/0117358 A1 | 6/2004 | Von Kaenel et al. |
| 2004/0122681 A1 | 6/2004 | Ruvolo et al. |
| 2004/0122696 A1 | 6/2004 | Beringer |
| 2004/0122697 A1 | 6/2004 | Becerra et al. |

(56) References Cited

U.S. PATENT DOCUMENTS

| | | |
|---|---|---|
| 2004/0128150 A1 | 7/2004 | Lundegren |
| 2004/0128156 A1 | 7/2004 | Beringer et al. |
| 2004/0128215 A1 | 7/2004 | Florance et al. |
| 2004/0128227 A1 | 7/2004 | Whipple et al. |
| 2004/0128230 A1 | 7/2004 | Oppenheimer et al. |
| 2004/0133440 A1 | 7/2004 | Carolan et al. |
| 2004/0133493 A1 | 7/2004 | Ford et al. |
| 2004/0133509 A1 | 7/2004 | McCoy et al. |
| 2004/0133513 A1 | 7/2004 | McCoy et al. |
| 2004/0133514 A1 | 7/2004 | Zielke et al. |
| 2004/0133515 A1 | 7/2004 | McCoy et al. |
| 2004/0138992 A1 | 7/2004 | DeFrancesco et al. |
| 2004/0138994 A1 | 7/2004 | DeFrancesco et al. |
| 2004/0138997 A1 | 7/2004 | DeFrancesco et al. |
| 2004/0139025 A1 | 7/2004 | Coleman |
| 2004/0141005 A1 | 7/2004 | Banatwala et al. |
| 2004/0143546 A1 | 7/2004 | Wood et al. |
| 2004/0143596 A1 | 7/2004 | Sirkin |
| 2004/0148200 A1 | 7/2004 | Hodges |
| 2004/0153330 A1 | 8/2004 | Miller et al. |
| 2004/0153448 A1 | 8/2004 | Cheng et al. |
| 2004/0153521 A1 | 8/2004 | Kogo |
| 2004/0158523 A1 | 8/2004 | Dort |
| 2004/0158723 A1 | 8/2004 | Root |
| 2004/0159700 A1 | 8/2004 | Khan et al. |
| 2004/0167793 A1 | 8/2004 | Masuoka et al. |
| 2004/0172360 A1 | 9/2004 | Mabrey et al. |
| 2004/0176995 A1 | 9/2004 | Fusz |
| 2004/0177035 A1 | 9/2004 | Silva |
| 2004/0186807 A1 | 9/2004 | Nathans et al. |
| 2004/0193538 A1 | 9/2004 | Raines |
| 2004/0193891 A1 | 9/2004 | Ollila |
| 2004/0198386 A1 | 10/2004 | Dupray |
| 2004/0199456 A1 | 10/2004 | Flint et al. |
| 2004/0199789 A1 | 10/2004 | Shaw et al. |
| 2004/0204948 A1 | 10/2004 | Singletary et al. |
| 2004/0210661 A1 | 10/2004 | Thompson |
| 2004/0215584 A1 | 10/2004 | Yao |
| 2004/0215673 A1 | 10/2004 | Furukawa et al. |
| 2004/0220865 A1 | 11/2004 | Lozowski et al. |
| 2004/0220896 A1 | 11/2004 | Finlay et al. |
| 2004/0220918 A1 | 11/2004 | Scriffignano et al. |
| 2004/0221043 A1 | 11/2004 | Su et al. |
| 2004/0225099 A1 | 11/2004 | Hohberg et al. |
| 2004/0225545 A1 | 11/2004 | Turner et al. |
| 2004/0225594 A1 | 11/2004 | Nolan, III et al. |
| 2004/0225596 A1 | 11/2004 | Kemper et al. |
| 2004/0225609 A1 | 11/2004 | Greene |
| 2004/0225643 A1 | 11/2004 | Alpha et al. |
| 2004/0230499 A1 | 11/2004 | Stack |
| 2004/0230527 A1 | 11/2004 | Hansen et al. |
| 2004/0230534 A1 | 11/2004 | McGough |
| 2004/0236688 A1 | 11/2004 | Bozeman |
| 2004/0243450 A1 | 12/2004 | Bernard, Jr. et al. |
| 2004/0243508 A1 | 12/2004 | Samson et al. |
| 2004/0243514 A1 | 12/2004 | Wankmueller |
| 2004/0243518 A1 | 12/2004 | Clifton et al. |
| 2004/0243588 A1 | 12/2004 | Tanner et al. |
| 2004/0243832 A1 | 12/2004 | Wilf et al. |
| 2004/0249811 A1 | 12/2004 | Shostack |
| 2004/0250085 A1 | 12/2004 | Tattan et al. |
| 2004/0250107 A1 | 12/2004 | Guo |
| 2004/0254935 A1 | 12/2004 | Chagoly et al. |
| 2004/0255127 A1 | 12/2004 | Arnouse |
| 2004/0267714 A1 | 12/2004 | Frid et al. |
| 2005/0004864 A1 | 1/2005 | Lent et al. |
| 2005/0005168 A1 | 1/2005 | Dick |
| 2005/0010494 A1 | 1/2005 | Mourad et al. |
| 2005/0010513 A1 | 1/2005 | Duckworth et al. |
| 2005/0010555 A1 | 1/2005 | Gallivan |
| 2005/0015273 A1 | 1/2005 | Iyer |
| 2005/0021457 A1 | 1/2005 | Johnson et al. |
| 2005/0021476 A1 | 1/2005 | Candella et al. |
| 2005/0021551 A1 | 1/2005 | Silva et al. |
| 2005/0027632 A1 | 2/2005 | Zeitoun et al. |
| 2005/0027666 A1 | 2/2005 | Beck |
| 2005/0027817 A1 | 2/2005 | Novik et al. |
| 2005/0027983 A1 | 2/2005 | Klawon |
| 2005/0027995 A1 | 2/2005 | Menschik et al. |
| 2005/0033660 A1 | 2/2005 | Solomon |
| 2005/0038737 A1 | 2/2005 | Norris |
| 2005/0049991 A1 | 3/2005 | Aggarwal |
| 2005/0050027 A1 | 3/2005 | Yeh et al. |
| 2005/0055231 A1 | 3/2005 | Lee |
| 2005/0055296 A1 | 3/2005 | Hattersley et al. |
| 2005/0058262 A1 | 3/2005 | Timmins et al. |
| 2005/0060244 A1 | 3/2005 | Goolkasian et al. |
| 2005/0060332 A1 | 3/2005 | Bernstein et al. |
| 2005/0071328 A1 | 3/2005 | Lawrence |
| 2005/0075985 A1 | 4/2005 | Cartmell |
| 2005/0080716 A1 | 4/2005 | Belyi et al. |
| 2005/0080723 A1 | 4/2005 | Burchetta et al. |
| 2005/0080796 A1 | 4/2005 | Midgley |
| 2005/0086126 A1 | 4/2005 | Patterson |
| 2005/0086261 A1 | 4/2005 | Mammone |
| 2005/0091164 A1 | 4/2005 | Varble |
| 2005/0097017 A1 | 5/2005 | Hanratty |
| 2005/0097039 A1 | 5/2005 | Kulcsar et al. |
| 2005/0097320 A1 | 5/2005 | Golan et al. |
| 2005/0102180 A1 | 5/2005 | Gailey et al. |
| 2005/0102209 A1 | 5/2005 | Sagrillo et al. |
| 2005/0105719 A1 | 5/2005 | Huda |
| 2005/0108396 A1 | 5/2005 | Bittner |
| 2005/0108631 A1 | 5/2005 | Amorin et al. |
| 2005/0113991 A1 | 5/2005 | Rogers et al. |
| 2005/0114335 A1 | 5/2005 | Wesinger, Jr. et al. |
| 2005/0114344 A1 | 5/2005 | Wesinger, Jr. et al. |
| 2005/0114345 A1 | 5/2005 | Wesinger, Jr. et al. |
| 2005/0119978 A1 | 6/2005 | Ates |
| 2005/0125291 A1 | 6/2005 | Demkiw Grayson et al. |
| 2005/0125397 A1 | 6/2005 | Gross et al. |
| 2005/0125686 A1 | 6/2005 | Brandt |
| 2005/0137899 A1 | 6/2005 | Davies et al. |
| 2005/0138391 A1 | 6/2005 | Mandalia et al. |
| 2005/0144133 A1 | 6/2005 | Hoffman et al. |
| 2005/0144143 A1 | 6/2005 | Freiberg |
| 2005/0144452 A1 | 6/2005 | Lynch et al. |
| 2005/0154664 A1 | 7/2005 | Guy et al. |
| 2005/0154665 A1 | 7/2005 | Kerr |
| 2005/0154769 A1 | 7/2005 | Eckart et al. |
| 2005/0160051 A1 | 7/2005 | Johnson |
| 2005/0160280 A1 | 7/2005 | Caslin et al. |
| 2005/0166262 A1 | 7/2005 | Beattie et al. |
| 2005/0171884 A1 | 8/2005 | Arnott |
| 2005/0177397 A1 | 8/2005 | Kane |
| 2005/0181765 A1 | 8/2005 | Mark |
| 2005/0187948 A1 | 8/2005 | Monitzer et al. |
| 2005/0192008 A1 | 9/2005 | Desai et al. |
| 2005/0193093 A1 | 9/2005 | Mathew et al. |
| 2005/0197953 A1 | 9/2005 | Broadbent et al. |
| 2005/0198377 A1 | 9/2005 | Ferguson et al. |
| 2005/0203768 A1 | 9/2005 | Florance |
| 2005/0203844 A1 | 9/2005 | Ferguson et al. |
| 2005/0203864 A1 | 9/2005 | Schmidt et al. |
| 2005/0208461 A1 | 9/2005 | Krebs et al. |
| 2005/0216434 A1 | 9/2005 | Haveliwala et al. |
| 2005/0216524 A1 | 9/2005 | Gomes et al. |
| 2005/0216582 A1 | 9/2005 | Toomey et al. |
| 2005/0216953 A1 | 9/2005 | Ellingson |
| 2005/0216955 A1 | 9/2005 | Wilkins et al. |
| 2005/0226224 A1 | 10/2005 | Lee et al. |
| 2005/0240578 A1 | 10/2005 | Biederman et al. |
| 2005/0246338 A1 | 11/2005 | Bird |
| 2005/0251474 A1 | 11/2005 | Shinn et al. |
| 2005/0256766 A1 | 11/2005 | Garcia et al. |
| 2005/0256809 A1 | 11/2005 | Sadri |
| 2005/0257250 A1 | 11/2005 | Mitchell et al. |
| 2005/0262158 A1 | 11/2005 | Sauermann |
| 2005/0267840 A1 | 12/2005 | Holm-Blagg et al. |
| 2005/0273431 A1 | 12/2005 | Abel et al. |
| 2005/0273442 A1 | 12/2005 | Bennett et al. |
| 2005/0273849 A1 | 12/2005 | Araujo et al. |
| 2005/0283415 A1 | 12/2005 | Studnitzer et al. |
| 2005/0288998 A1 | 12/2005 | Verma et al. |

(56) References Cited

U.S. PATENT DOCUMENTS

| | | |
|---|---|---|
| 2005/0289003 A1 | 12/2005 | Thompson et al. |
| 2006/0004623 A1 | 1/2006 | Jasti |
| 2006/0004626 A1 | 1/2006 | Holmen et al. |
| 2006/0010072 A1 | 1/2006 | Eisen |
| 2006/0010391 A1 | 1/2006 | Uemura et al. |
| 2006/0010487 A1 | 1/2006 | Fierer et al. |
| 2006/0015425 A1 | 1/2006 | Brooks |
| 2006/0016107 A1 | 1/2006 | Davis |
| 2006/0020611 A1 | 1/2006 | Gilbert et al. |
| 2006/0026453 A1 | 2/2006 | Frost et al. |
| 2006/0031158 A1 | 2/2006 | Orman |
| 2006/0031177 A1 | 2/2006 | Rule |
| 2006/0032909 A1 | 2/2006 | Seegar |
| 2006/0036543 A1 | 2/2006 | Blagg et al. |
| 2006/0036748 A1 | 2/2006 | Nusbaum et al. |
| 2006/0036870 A1 | 2/2006 | Dasari et al. |
| 2006/0041464 A1 | 2/2006 | Powers et al. |
| 2006/0041670 A1 | 2/2006 | Musseleck et al. |
| 2006/0047605 A1 | 3/2006 | Ahmad |
| 2006/0059062 A1 | 3/2006 | Wood et al. |
| 2006/0059083 A1 | 3/2006 | Friesen et al. |
| 2006/0059110 A1 | 3/2006 | Madhok et al. |
| 2006/0059362 A1 | 3/2006 | Paden et al. |
| 2006/0069635 A1 | 3/2006 | Ram et al. |
| 2006/0074986 A1 | 4/2006 | Mallalieu et al. |
| 2006/0074991 A1 | 4/2006 | Lussier et al. |
| 2006/0079211 A1 | 4/2006 | Degraeve |
| 2006/0080210 A1 | 4/2006 | Mourad et al. |
| 2006/0080216 A1 | 4/2006 | Hausman et al. |
| 2006/0080230 A1 | 4/2006 | Freiberg |
| 2006/0080233 A1 | 4/2006 | Mendelovich et al. |
| 2006/0080235 A1 | 4/2006 | Fukuda et al. |
| 2006/0080236 A1 | 4/2006 | Welker et al. |
| 2006/0080251 A1 | 4/2006 | Fried et al. |
| 2006/0080263 A1 | 4/2006 | Willis et al. |
| 2006/0080274 A1 | 4/2006 | Mourad |
| 2006/0085334 A1 | 4/2006 | Murphy |
| 2006/0085361 A1 | 4/2006 | Hoerle et al. |
| 2006/0085454 A1 | 4/2006 | Blegen et al. |
| 2006/0095289 A1 | 5/2006 | Bunning |
| 2006/0101508 A1 | 5/2006 | Taylor |
| 2006/0106670 A1 | 5/2006 | Cai et al. |
| 2006/0116931 A1 | 6/2006 | Storey |
| 2006/0116932 A1 | 6/2006 | Storey |
| 2006/0129419 A1 | 6/2006 | Flaxer et al. |
| 2006/0129472 A1 | 6/2006 | Harrington |
| 2006/0129481 A1 | 6/2006 | Bhatt et al. |
| 2006/0129533 A1 | 6/2006 | Purvis |
| 2006/0131390 A1 | 6/2006 | Kim |
| 2006/0136330 A1 | 6/2006 | DeRoy et al. |
| 2006/0136524 A1 | 6/2006 | Wohlers et al. |
| 2006/0136595 A1 | 6/2006 | Satyavolu |
| 2006/0140460 A1 | 6/2006 | Coutts |
| 2006/0149674 A1 | 7/2006 | Cook et al. |
| 2006/0155573 A1 | 7/2006 | Hartunian |
| 2006/0155780 A1 | 7/2006 | Sakairi et al. |
| 2006/0161435 A1 | 7/2006 | Atef et al. |
| 2006/0161478 A1 | 7/2006 | Turner et al. |
| 2006/0161554 A1 | 7/2006 | Lucovsky et al. |
| 2006/0173776 A1 | 8/2006 | Shalley et al. |
| 2006/0173792 A1 | 8/2006 | Glass |
| 2006/0178971 A1 | 8/2006 | Owen et al. |
| 2006/0179050 A1 | 8/2006 | Giang et al. |
| 2006/0184440 A1 | 8/2006 | Britti et al. |
| 2006/0184585 A1 | 8/2006 | Grear et al. |
| 2006/0190394 A1 | 8/2006 | Fraser et al. |
| 2006/0195351 A1 | 8/2006 | Bayburtian |
| 2006/0195688 A1 | 8/2006 | Drissi et al. |
| 2006/0200583 A1 | 9/2006 | Le Lann et al. |
| 2006/0202012 A1 | 9/2006 | Grano et al. |
| 2006/0204051 A1 | 9/2006 | Holland, IV |
| 2006/0212407 A1 | 9/2006 | Lyon |
| 2006/0212486 A1 | 9/2006 | Kennis et al. |
| 2006/0213985 A1 | 9/2006 | Walker et al. |
| 2006/0218407 A1 | 9/2006 | Toms |
| 2006/0223043 A1 | 10/2006 | Dancy-Edwards et al. |
| 2006/0224498 A1 | 10/2006 | Chin |
| 2006/0229943 A1 | 10/2006 | Mathias et al. |
| 2006/0229961 A1 | 10/2006 | Lyftogt et al. |
| 2006/0230343 A1 | 10/2006 | Armandpour et al. |
| 2006/0235935 A1 | 10/2006 | Ng |
| 2006/0239512 A1 | 10/2006 | Petrillo |
| 2006/0241923 A1 | 10/2006 | Xu et al. |
| 2006/0242047 A1 | 10/2006 | Haggerty et al. |
| 2006/0245731 A1 | 11/2006 | Lai |
| 2006/0248021 A1 | 11/2006 | Jain et al. |
| 2006/0248048 A1 | 11/2006 | Jain et al. |
| 2006/0248525 A1 | 11/2006 | Hopkins |
| 2006/0253358 A1 | 11/2006 | Delgrosso et al. |
| 2006/0253463 A1 | 11/2006 | Wu et al. |
| 2006/0262929 A1 | 11/2006 | Vatanen et al. |
| 2006/0265243 A1 | 11/2006 | Racho et al. |
| 2006/0267999 A1 | 11/2006 | Cash et al. |
| 2006/0271456 A1 | 11/2006 | Romain et al. |
| 2006/0271457 A1 | 11/2006 | Romain et al. |
| 2006/0271472 A1 | 11/2006 | Cagan |
| 2006/0271633 A1 | 11/2006 | Adler |
| 2006/0276171 A1 | 12/2006 | Pousti |
| 2006/0277089 A1 | 12/2006 | Hubbard et al. |
| 2006/0277092 A1 | 12/2006 | Williams |
| 2006/0277102 A1 | 12/2006 | Agliozzo |
| 2006/0277141 A1 | 12/2006 | Palmer |
| 2006/0282359 A1 | 12/2006 | Nobili et al. |
| 2006/0282373 A1 | 12/2006 | Stone |
| 2006/0282374 A1 | 12/2006 | Stone |
| 2006/0282429 A1 | 12/2006 | Hernandez-Sherrington et al. |
| 2006/0282660 A1 | 12/2006 | Varghese et al. |
| 2006/0282819 A1 | 12/2006 | Graham et al. |
| 2006/0282886 A1 | 12/2006 | Gaug |
| 2006/0287764 A1 | 12/2006 | Kraft |
| 2006/0287765 A1 | 12/2006 | Kraft |
| 2006/0287766 A1 | 12/2006 | Kraft |
| 2006/0287767 A1 | 12/2006 | Kraft |
| 2006/0288090 A1 | 12/2006 | Kraft |
| 2006/0293932 A1 | 12/2006 | Cash et al. |
| 2006/0293979 A1 | 12/2006 | Cash et al. |
| 2006/0293987 A1 | 12/2006 | Shapiro |
| 2006/0294199 A1 | 12/2006 | Bertholf |
| 2007/0005508 A1 | 1/2007 | Chiang |
| 2007/0005984 A1 | 1/2007 | Florencio et al. |
| 2007/0011020 A1 | 1/2007 | Martin |
| 2007/0011030 A1 | 1/2007 | Bregante et al. |
| 2007/0011032 A1 | 1/2007 | Bregante et al. |
| 2007/0011083 A1 | 1/2007 | Bird et al. |
| 2007/0016500 A1 | 1/2007 | Chatterji et al. |
| 2007/0016517 A1 | 1/2007 | Solomon |
| 2007/0022141 A1 | 1/2007 | Singleton et al. |
| 2007/0022297 A1 | 1/2007 | Britti et al. |
| 2007/0027778 A1 | 2/2007 | Schellhammer et al. |
| 2007/0027816 A1 | 2/2007 | Writer |
| 2007/0030282 A1 | 2/2007 | Cash et al. |
| 2007/0032240 A1 | 2/2007 | Finnegan et al. |
| 2007/0038483 A1 | 2/2007 | Wood |
| 2007/0038497 A1 | 2/2007 | Britti et al. |
| 2007/0038568 A1 | 2/2007 | Greene et al. |
| 2007/0039049 A1 | 2/2007 | Kupferman et al. |
| 2007/0040015 A1 | 2/2007 | Carlson et al. |
| 2007/0043577 A1 | 2/2007 | Kasower |
| 2007/0047714 A1 | 3/2007 | Baniak et al. |
| 2007/0050777 A1 | 3/2007 | Hutchinson et al. |
| 2007/0055621 A1 | 3/2007 | Tischler et al. |
| 2007/0057947 A1 | 3/2007 | Yokoyama |
| 2007/0061260 A1 | 3/2007 | deGroeve et al. |
| 2007/0067235 A1 | 3/2007 | Nathans et al. |
| 2007/0067285 A1 | 3/2007 | Blume et al. |
| 2007/0067297 A1 | 3/2007 | Kublickis |
| 2007/0067437 A1 | 3/2007 | Sindambiwe |
| 2007/0072190 A1 | 3/2007 | Aggarwal |
| 2007/0073577 A1 | 3/2007 | Krause |
| 2007/0073889 A1 | 3/2007 | Morris |
| 2007/0078908 A1 | 4/2007 | Rohatgi et al. |
| 2007/0078985 A1 | 4/2007 | Shao et al. |
| 2007/0078990 A1 | 4/2007 | Hopkins |
| 2007/0080826 A1 | 4/2007 | Chang |

(56) References Cited

U.S. PATENT DOCUMENTS

| | | |
|---|---|---|
| 2007/0083460 A1 | 4/2007 | Bachenheimer |
| 2007/0083463 A1 | 4/2007 | Kraft |
| 2007/0088821 A1 | 4/2007 | Sankuratripati et al. |
| 2007/0093234 A1 | 4/2007 | Willis et al. |
| 2007/0094230 A1 | 4/2007 | Subramaniam et al. |
| 2007/0094241 A1 | 4/2007 | M. Blackwell et al. |
| 2007/0094264 A1 | 4/2007 | Nair |
| 2007/0112667 A1 | 5/2007 | Rucker |
| 2007/0112668 A1 | 5/2007 | Celano et al. |
| 2007/0112670 A1 | 5/2007 | DeFrancesco et al. |
| 2007/0118393 A1 | 5/2007 | Rosen et al. |
| 2007/0121843 A1 | 5/2007 | Atazky et al. |
| 2007/0124235 A1 | 5/2007 | Chakraborty et al. |
| 2007/0124256 A1 | 5/2007 | Crooks et al. |
| 2007/0130070 A1 | 6/2007 | Williams |
| 2007/0130347 A1 | 6/2007 | Rangan et al. |
| 2007/0131755 A1 | 6/2007 | Chang |
| 2007/0136109 A1 | 6/2007 | Yager et al. |
| 2007/0143123 A1 | 6/2007 | Goldberg et al. |
| 2007/0143825 A1 | 6/2007 | Goffin |
| 2007/0149184 A1 | 6/2007 | Viegers et al. |
| 2007/0152068 A1 | 7/2007 | Kurita |
| 2007/0153085 A1 | 7/2007 | Chang |
| 2007/0153710 A1 | 7/2007 | Hopkins |
| 2007/0156554 A1 | 7/2007 | Nikoley et al. |
| 2007/0156576 A1 | 7/2007 | Imrey et al. |
| 2007/0156581 A1 | 7/2007 | Imrey et al. |
| 2007/0156589 A1 | 7/2007 | Zimler et al. |
| 2007/0156692 A1 | 7/2007 | Rosewarne |
| 2007/0157107 A1 | 7/2007 | Bishop |
| 2007/0160458 A1 | 7/2007 | Yen |
| 2007/0162307 A1 | 7/2007 | Austin et al. |
| 2007/0162369 A1 | 7/2007 | Hardison |
| 2007/0162458 A1 | 7/2007 | Fasciano |
| 2007/0174166 A1 | 7/2007 | Jones |
| 2007/0174186 A1 | 7/2007 | Hokland |
| 2007/0174448 A1 | 7/2007 | Ahuja et al. |
| 2007/0174903 A1 | 7/2007 | Greff |
| 2007/0180380 A1 | 8/2007 | Khavari et al. |
| 2007/0185797 A1 | 8/2007 | Robinson |
| 2007/0192121 A1 | 8/2007 | Routson et al. |
| 2007/0192167 A1 | 8/2007 | Lei et al. |
| 2007/0192853 A1 | 8/2007 | Shraim et al. |
| 2007/0198432 A1 | 8/2007 | Pitroda et al. |
| 2007/0203954 A1 | 8/2007 | Vargas et al. |
| 2007/0204033 A1 | 8/2007 | Bookbinder et al. |
| 2007/0204212 A1 | 8/2007 | Chamberlain et al. |
| 2007/0204338 A1 | 8/2007 | Aiello et al. |
| 2007/0205266 A1 | 9/2007 | Carr et al. |
| 2007/0206917 A1 | 9/2007 | Ono et al. |
| 2007/0208640 A1 | 9/2007 | Banasiak et al. |
| 2007/0214000 A1 | 9/2007 | Shahrabi et al. |
| 2007/0219966 A1 | 9/2007 | Baylis et al. |
| 2007/0220003 A1 | 9/2007 | Chern et al. |
| 2007/0220092 A1 | 9/2007 | Heitzeberg et al. |
| 2007/0220275 A1 | 9/2007 | Heitzeberg et al. |
| 2007/0220581 A1 | 9/2007 | Chang |
| 2007/0220611 A1 | 9/2007 | Socolow et al. |
| 2007/0226010 A1 | 9/2007 | Larsen |
| 2007/0226047 A1 | 9/2007 | Ward |
| 2007/0226093 A1 | 9/2007 | Chan et al. |
| 2007/0226122 A1 | 9/2007 | Burrell et al. |
| 2007/0226129 A1 | 9/2007 | Liao et al. |
| 2007/0233591 A1 | 10/2007 | Newton |
| 2007/0236562 A1 | 10/2007 | Chang |
| 2007/0239493 A1 | 10/2007 | Sweetland et al. |
| 2007/0240206 A1 | 10/2007 | Wu et al. |
| 2007/0244782 A1 | 10/2007 | Chimento |
| 2007/0244807 A1 | 10/2007 | Andringa et al. |
| 2007/0245245 A1 | 10/2007 | Blue et al. |
| 2007/0250441 A1 | 10/2007 | Paulsen et al. |
| 2007/0250459 A1 | 10/2007 | Schwarz et al. |
| 2007/0261108 A1 | 11/2007 | Lee et al. |
| 2007/0261114 A1 | 11/2007 | Pomerantsev |
| 2007/0262140 A1 | 11/2007 | Long, Sr. |
| 2007/0266439 A1 | 11/2007 | Kraft |
| 2007/0273558 A1 | 11/2007 | Smith |
| 2007/0276780 A1 | 11/2007 | Iriyama et al. |
| 2007/0282730 A1 | 12/2007 | Carpenter et al. |
| 2007/0282736 A1 | 12/2007 | Conlin et al. |
| 2007/0282743 A1 | 12/2007 | Lovelett |
| 2007/0282959 A1 | 12/2007 | Stern |
| 2007/0287415 A1 | 12/2007 | Yamada |
| 2007/0288355 A1 | 12/2007 | Roland et al. |
| 2007/0288360 A1 | 12/2007 | Seeklus |
| 2007/0294195 A1 | 12/2007 | Curry et al. |
| 2007/0299759 A1 | 12/2007 | Kelly |
| 2007/0299770 A1 | 12/2007 | Delinsky |
| 2007/0299772 A1 | 12/2007 | Mastie et al. |
| 2008/0004957 A1 | 1/2008 | Hildreth et al. |
| 2008/0010203 A1 | 1/2008 | Grant |
| 2008/0010206 A1 | 1/2008 | Coleman |
| 2008/0010687 A1 | 1/2008 | Gonen et al. |
| 2008/0015919 A1 | 1/2008 | Busse et al. |
| 2008/0015979 A1 | 1/2008 | Bentley |
| 2008/0021802 A1 | 1/2008 | Pendleton |
| 2008/0021804 A1 | 1/2008 | Deckoff |
| 2008/0021816 A1 | 1/2008 | Lent et al. |
| 2008/0027858 A1 | 1/2008 | Benson |
| 2008/0027859 A1 | 1/2008 | Nathans et al. |
| 2008/0028435 A1 | 1/2008 | Strickland et al. |
| 2008/0028446 A1 | 1/2008 | Burgoyne |
| 2008/0033742 A1 | 2/2008 | Bernasconi |
| 2008/0033750 A1 | 2/2008 | Burriss et al. |
| 2008/0033956 A1 | 2/2008 | Saha et al. |
| 2008/0040176 A1 | 2/2008 | Ehling |
| 2008/0040475 A1 | 2/2008 | Bosworth et al. |
| 2008/0040610 A1 | 2/2008 | Fergusson |
| 2008/0046383 A1 | 2/2008 | Hirtenstein et al. |
| 2008/0047017 A1 | 2/2008 | Renaud |
| 2008/0052170 A1 | 2/2008 | Storey |
| 2008/0052182 A1 | 2/2008 | Marshall |
| 2008/0052244 A1 | 2/2008 | Tsuei et al. |
| 2008/0059224 A1 | 3/2008 | Schechter |
| 2008/0059317 A1 | 3/2008 | Chandran et al. |
| 2008/0059352 A1 | 3/2008 | Chandran |
| 2008/0059364 A1 | 3/2008 | Tidwell et al. |
| 2008/0059447 A1 | 3/2008 | Winner et al. |
| 2008/0059449 A1 | 3/2008 | Webster et al. |
| 2008/0060054 A1 | 3/2008 | Srivastava |
| 2008/0065774 A1 | 3/2008 | Keeler |
| 2008/0066188 A1 | 3/2008 | Kwak |
| 2008/0071682 A1 | 3/2008 | Dominguez |
| 2008/0072316 A1 | 3/2008 | Chang et al. |
| 2008/0077526 A1 | 3/2008 | Arumugam |
| 2008/0077551 A1 | 3/2008 | Akerman et al. |
| 2008/0079809 A1 | 4/2008 | Chang |
| 2008/0082536 A1 | 4/2008 | Schwabe et al. |
| 2008/0083021 A1 | 4/2008 | Doane et al. |
| 2008/0086400 A1 | 4/2008 | Ardelean et al. |
| 2008/0086431 A1 | 4/2008 | Robinson et al. |
| 2008/0091519 A1 | 4/2008 | Foss |
| 2008/0091530 A1 | 4/2008 | Egnatios et al. |
| 2008/0097822 A1 | 4/2008 | Schigel et al. |
| 2008/0103798 A1 | 5/2008 | Domenikos et al. |
| 2008/0103800 A1 | 5/2008 | Domenikos et al. |
| 2008/0103972 A1 | 5/2008 | Lanc |
| 2008/0104672 A1 | 5/2008 | Lunde et al. |
| 2008/0109308 A1 | 5/2008 | Storey |
| 2008/0109422 A1 | 5/2008 | Dedhia |
| 2008/0109740 A1 | 5/2008 | Prinsen et al. |
| 2008/0109875 A1 | 5/2008 | Kraft |
| 2008/0110973 A1 | 5/2008 | Nathans et al. |
| 2008/0114670 A1 | 5/2008 | Friesen |
| 2008/0114855 A1 | 5/2008 | Welingkar et al. |
| 2008/0115191 A1 | 5/2008 | Kim et al. |
| 2008/0115226 A1 | 5/2008 | Welingkar et al. |
| 2008/0120155 A1 | 5/2008 | Pliha |
| 2008/0120204 A1 | 5/2008 | Conner et al. |
| 2008/0120416 A1 | 5/2008 | Hopkins et al. |
| 2008/0120569 A1 | 5/2008 | Mann et al. |
| 2008/0120716 A1 | 5/2008 | Hall et al. |
| 2008/0122920 A1 | 5/2008 | Chang |
| 2008/0126233 A1 | 5/2008 | Hogan |

(56) References Cited

U.S. PATENT DOCUMENTS

| | | |
|---|---|---|
| 2008/0133273 A1 | 6/2008 | Marshall |
| 2008/0133278 A1 | 6/2008 | Stanfield |
| 2008/0133657 A1 | 6/2008 | Pennington |
| 2008/0140476 A1 | 6/2008 | Anand et al. |
| 2008/0140576 A1 | 6/2008 | Lewis et al. |
| 2008/0140734 A1 | 6/2008 | Wagner |
| 2008/0140780 A1 | 6/2008 | Hopkins et al. |
| 2008/0141346 A1 | 6/2008 | Kay et al. |
| 2008/0147523 A1 | 6/2008 | Mulry et al. |
| 2008/0148368 A1 | 6/2008 | Zurko et al. |
| 2008/0148392 A1 | 6/2008 | Akens |
| 2008/0154758 A1 | 6/2008 | Schattmaier et al. |
| 2008/0155686 A1 | 6/2008 | McNair |
| 2008/0162236 A1 | 7/2008 | Sommerer |
| 2008/0162317 A1 | 7/2008 | Banaugh et al. |
| 2008/0162350 A1 | 7/2008 | Allen-Rouman et al. |
| 2008/0162383 A1 | 7/2008 | Kraft |
| 2008/0172304 A1 | 7/2008 | Berkowitz |
| 2008/0175360 A1 | 7/2008 | Schwarz et al. |
| 2008/0177655 A1 | 7/2008 | Zalik |
| 2008/0183480 A1 | 7/2008 | Carlson et al. |
| 2008/0183504 A1 | 7/2008 | Highley |
| 2008/0183564 A1 | 7/2008 | Tien et al. |
| 2008/0183585 A1 | 7/2008 | Vianello |
| 2008/0184270 A1 | 7/2008 | Cole et al. |
| 2008/0184351 A1 | 7/2008 | Gephart |
| 2008/0195548 A1 | 8/2008 | Chu et al. |
| 2008/0195600 A1 | 8/2008 | Deakter |
| 2008/0201257 A1 | 8/2008 | Lewis et al. |
| 2008/0201401 A1 | 8/2008 | Pugh et al. |
| 2008/0205655 A1 | 8/2008 | Wilkins et al. |
| 2008/0205774 A1 | 8/2008 | Brinker et al. |
| 2008/0208548 A1 | 8/2008 | Metzger et al. |
| 2008/0208610 A1 | 8/2008 | Thomas et al. |
| 2008/0208631 A1 | 8/2008 | Morita et al. |
| 2008/0208726 A1 | 8/2008 | Tsantes et al. |
| 2008/0208735 A1 | 8/2008 | Balet et al. |
| 2008/0208752 A1 | 8/2008 | Gottlieb et al. |
| 2008/0208873 A1 | 8/2008 | Boehmer |
| 2008/0212845 A1 | 9/2008 | Lund |
| 2008/0215640 A1 | 9/2008 | Hartz et al. |
| 2008/0216156 A1 | 9/2008 | Kosaka |
| 2008/0221972 A1 | 9/2008 | Megdal et al. |
| 2008/0222027 A1 | 9/2008 | Megdal et al. |
| 2008/0222706 A1 | 9/2008 | Renaud et al. |
| 2008/0222722 A1 | 9/2008 | Navratil et al. |
| 2008/0228556 A1 | 9/2008 | Megdal et al. |
| 2008/0228775 A1 | 9/2008 | Abhyanker et al. |
| 2008/0229415 A1 | 9/2008 | Kapoor et al. |
| 2008/0244008 A1 | 10/2008 | Wilkinson et al. |
| 2008/0249869 A1 | 10/2008 | Angell et al. |
| 2008/0249925 A1 | 10/2008 | Nazari et al. |
| 2008/0255975 A1 | 10/2008 | Chaudhuri et al. |
| 2008/0255992 A1 | 10/2008 | Lin |
| 2008/0256613 A1 | 10/2008 | Grover |
| 2008/0263013 A1 | 10/2008 | Hopkins |
| 2008/0263058 A1 | 10/2008 | Peden |
| 2008/0263638 A1 | 10/2008 | McMurtry et al. |
| 2008/0270038 A1 | 10/2008 | Partovi et al. |
| 2008/0270209 A1 | 10/2008 | Mauseth et al. |
| 2008/0270292 A1 | 10/2008 | Ghosh et al. |
| 2008/0270294 A1 | 10/2008 | Lent et al. |
| 2008/0270295 A1 | 10/2008 | Lent et al. |
| 2008/0270299 A1 | 10/2008 | Peng |
| 2008/0275816 A1 | 11/2008 | Hazlehurst |
| 2008/0277465 A1 | 11/2008 | Pletz et al. |
| 2008/0281737 A1 | 11/2008 | Fajardo |
| 2008/0282324 A1 | 11/2008 | Hoal |
| 2008/0284586 A1 | 11/2008 | Chang |
| 2008/0288283 A1 | 11/2008 | Baldwin, Jr. et al. |
| 2008/0288299 A1 | 11/2008 | Schultz |
| 2008/0294501 A1 | 11/2008 | Rennich et al. |
| 2008/0294540 A1 | 11/2008 | Celka et al. |
| 2008/0297602 A1 | 12/2008 | Chang |
| 2008/0301016 A1 | 12/2008 | Durvasula et al. |
| 2008/0301188 A1 | 12/2008 | O'Hara |
| 2008/0306750 A1 | 12/2008 | Wunder et al. |
| 2008/0306846 A1 | 12/2008 | Ferguson |
| 2008/0307063 A1 | 12/2008 | Caughey |
| 2008/0312969 A1 | 12/2008 | Raines et al. |
| 2008/0314977 A1 | 12/2008 | Domenica et al. |
| 2008/0316010 A1 | 12/2008 | Chang |
| 2008/0319861 A1 | 12/2008 | Hopkins |
| 2008/0319889 A1 | 12/2008 | Hammad |
| 2008/0319896 A1 | 12/2008 | Carlson et al. |
| 2008/0320575 A1 | 12/2008 | Gelb et al. |
| 2009/0006230 A1 | 1/2009 | Lyda et al. |
| 2009/0006475 A1 | 1/2009 | Udezue et al. |
| 2009/0006582 A1 | 1/2009 | Daswani et al. |
| 2009/0018986 A1 | 1/2009 | Alcorn et al. |
| 2009/0018996 A1 | 1/2009 | Hunt et al. |
| 2009/0024428 A1 | 1/2009 | Hudock, Jr. |
| 2009/0024462 A1 | 1/2009 | Lin |
| 2009/0024484 A1 | 1/2009 | Walker et al. |
| 2009/0024485 A1 | 1/2009 | Haugen et al. |
| 2009/0024505 A1 | 1/2009 | Patel et al. |
| 2009/0030776 A1 | 1/2009 | Walker et al. |
| 2009/0031426 A1 | 1/2009 | Dal Lago et al. |
| 2009/0037279 A1 | 2/2009 | Chockalingam et al. |
| 2009/0037323 A1 | 2/2009 | Feinstein et al. |
| 2009/0037332 A1 | 2/2009 | Cheung et al. |
| 2009/0043691 A1 | 2/2009 | Kasower |
| 2009/0048877 A1 | 2/2009 | Binns et al. |
| 2009/0048957 A1 | 2/2009 | Celano |
| 2009/0048999 A1 | 2/2009 | Gupta et al. |
| 2009/0055287 A1 | 2/2009 | Chin |
| 2009/0055312 A1 | 2/2009 | Chin |
| 2009/0055322 A1 | 2/2009 | Bykov et al. |
| 2009/0055404 A1 | 2/2009 | Heiden et al. |
| 2009/0055894 A1 | 2/2009 | Lorsch |
| 2009/0060343 A1 | 3/2009 | Rosea |
| 2009/0064297 A1 | 3/2009 | Selgas et al. |
| 2009/0070148 A1 | 3/2009 | Skocic |
| 2009/0076950 A1 | 3/2009 | Chang et al. |
| 2009/0076966 A1 | 3/2009 | Bishop et al. |
| 2009/0089190 A1 | 4/2009 | Girulat |
| 2009/0089193 A1 | 4/2009 | Palantin |
| 2009/0089869 A1 | 4/2009 | Varghese |
| 2009/0094064 A1 | 4/2009 | Tyler et al. |
| 2009/0094237 A1 | 4/2009 | Churi et al. |
| 2009/0094674 A1 | 4/2009 | Schwartz et al. |
| 2009/0094675 A1 | 4/2009 | Powers |
| 2009/0099941 A1 | 4/2009 | Berkowitz |
| 2009/0100047 A1 | 4/2009 | Jones et al. |
| 2009/0106141 A1 | 4/2009 | Becker |
| 2009/0106150 A1 | 4/2009 | Pelegero et al. |
| 2009/0106846 A1 | 4/2009 | Dupray et al. |
| 2009/0112650 A1 | 4/2009 | Iwane |
| 2009/0113532 A1 | 4/2009 | Lapidous |
| 2009/0119116 A1 | 5/2009 | Steen |
| 2009/0119169 A1 | 5/2009 | Chandratillake et al. |
| 2009/0119299 A1 | 5/2009 | Rhodes |
| 2009/0125369 A1 | 5/2009 | Kloostra et al. |
| 2009/0125972 A1 | 5/2009 | Hinton et al. |
| 2009/0126013 A1 | 5/2009 | Atwood et al. |
| 2009/0132347 A1 | 5/2009 | Anderson et al. |
| 2009/0132813 A1 | 5/2009 | Schibuk |
| 2009/0138335 A1 | 5/2009 | Lieberman |
| 2009/0144102 A1 | 6/2009 | Lopez |
| 2009/0144166 A1 | 6/2009 | Dickelman |
| 2009/0146879 A1 | 6/2009 | Chang |
| 2009/0147774 A1 | 6/2009 | Caughey |
| 2009/0150166 A1 | 6/2009 | Leite et al. |
| 2009/0150238 A1 | 6/2009 | Marsh et al. |
| 2009/0157564 A1 | 6/2009 | Cross |
| 2009/0157693 A1 | 6/2009 | Palahnuk |
| 2009/0158030 A1 | 6/2009 | Rasti |
| 2009/0164232 A1 | 6/2009 | Chmielewski et al. |
| 2009/0164380 A1 | 6/2009 | Brown |
| 2009/0164582 A1 | 6/2009 | Dasgupta et al. |
| 2009/0164929 A1 | 6/2009 | Chen et al. |
| 2009/0171723 A1 | 7/2009 | Jenkins |
| 2009/0172788 A1 | 7/2009 | Veldula et al. |
| 2009/0172795 A1 | 7/2009 | Ritari et al. |

(56) References Cited

U.S. PATENT DOCUMENTS

| | | |
|---|---|---|
| 2009/0177529 A1 | 7/2009 | Hadi |
| 2009/0177562 A1 | 7/2009 | Peace et al. |
| 2009/0177670 A1 | 7/2009 | Grenier et al. |
| 2009/0182661 A1 | 7/2009 | Irwin |
| 2009/0182873 A1 | 7/2009 | Spalink et al. |
| 2009/0183259 A1 | 7/2009 | Rinek et al. |
| 2009/0187607 A1 | 7/2009 | Yoo et al. |
| 2009/0195377 A1 | 8/2009 | Chang |
| 2009/0198557 A1 | 8/2009 | Wang et al. |
| 2009/0198602 A1 | 8/2009 | Wang et al. |
| 2009/0199264 A1 | 8/2009 | Lang |
| 2009/0199294 A1 | 8/2009 | Schneider |
| 2009/0204514 A1 | 8/2009 | Bhogal et al. |
| 2009/0204599 A1 | 8/2009 | Morris et al. |
| 2009/0210241 A1 | 8/2009 | Calloway |
| 2009/0210807 A1 | 8/2009 | Xiao et al. |
| 2009/0215431 A1 | 8/2009 | Koraichi |
| 2009/0216591 A1 | 8/2009 | Buerger et al. |
| 2009/0216640 A1 | 8/2009 | Masi |
| 2009/0217342 A1 | 8/2009 | Nadler |
| 2009/0222364 A1 | 9/2009 | McGlynn et al. |
| 2009/0222449 A1 * | 9/2009 | Hom ............... G06F 21/6218 707/999.009 |
| 2009/0222527 A1 | 9/2009 | Arconati et al. |
| 2009/0228295 A1 | 9/2009 | Lowy |
| 2009/0228392 A1 | 9/2009 | Pinson, III |
| 2009/0228918 A1 | 9/2009 | Rolff et al. |
| 2009/0228990 A1 | 9/2009 | Chen et al. |
| 2009/0233579 A1 | 9/2009 | Castell et al. |
| 2009/0234665 A1 | 9/2009 | Conkel |
| 2009/0234775 A1 | 9/2009 | Whitney et al. |
| 2009/0234814 A1 | 9/2009 | Boerries et al. |
| 2009/0234876 A1 | 9/2009 | Schigel et al. |
| 2009/0240609 A1 | 9/2009 | Cho et al. |
| 2009/0240624 A1 | 9/2009 | James et al. |
| 2009/0247122 A1 | 10/2009 | Fitzgerald et al. |
| 2009/0248573 A1 | 10/2009 | Haggerty et al. |
| 2009/0249440 A1 | 10/2009 | Platt et al. |
| 2009/0249451 A1 | 10/2009 | Su et al. |
| 2009/0254375 A1 | 10/2009 | Martinez et al. |
| 2009/0254476 A1 | 10/2009 | Sharma et al. |
| 2009/0254572 A1 | 10/2009 | Redlich et al. |
| 2009/0254656 A1 | 10/2009 | Vignisson et al. |
| 2009/0254971 A1 | 10/2009 | Herz et al. |
| 2009/0258334 A1 | 10/2009 | Pyne |
| 2009/0260064 A1 | 10/2009 | Mcdowell et al. |
| 2009/0265461 A1 | 10/2009 | Tarquini et al. |
| 2009/0271265 A1 | 10/2009 | Lay et al. |
| 2009/0271847 A1 | 10/2009 | Karjala et al. |
| 2009/0276368 A1 | 11/2009 | Martin et al. |
| 2009/0280467 A1 | 11/2009 | Ahart |
| 2009/0281816 A1 | 11/2009 | Houga et al. |
| 2009/0281941 A1 | 11/2009 | Worth |
| 2009/0281951 A1 | 11/2009 | Shakkarwar |
| 2009/0282479 A1 | 11/2009 | Smith et al. |
| 2009/0289110 A1 | 11/2009 | Regen et al. |
| 2009/0300066 A1 | 12/2009 | Guo et al. |
| 2009/0300604 A1 | 12/2009 | Barringer |
| 2009/0300641 A1 | 12/2009 | Friedman et al. |
| 2009/0307778 A1 | 12/2009 | Mardikar |
| 2009/0313049 A1 | 12/2009 | Joao et al. |
| 2009/0313134 A1 | 12/2009 | Faith et al. |
| 2009/0313562 A1 | 12/2009 | Appleyard et al. |
| 2009/0319638 A1 | 12/2009 | Faith et al. |
| 2009/0319648 A1 | 12/2009 | Dutta et al. |
| 2009/0327054 A1 | 12/2009 | Yao et al. |
| 2009/0327120 A1 | 12/2009 | Eze et al. |
| 2009/0327270 A1 | 12/2009 | Teevan et al. |
| 2009/0327487 A1 | 12/2009 | Olson et al. |
| 2009/0328173 A1 | 12/2009 | Jakobson et al. |
| 2010/0009320 A1 | 1/2010 | Wilkelis |
| 2010/0009332 A1 | 1/2010 | Yaskin et al. |
| 2010/0010935 A1 | 1/2010 | Shelton |
| 2010/0010993 A1 | 1/2010 | Hussey, Jr. et al. |
| 2010/0011428 A1 | 1/2010 | Atwood et al. |
| 2010/0023434 A1 | 1/2010 | Bond |
| 2010/0023440 A1 | 1/2010 | Fraser et al. |
| 2010/0023448 A1 | 1/2010 | Eze |
| 2010/0023506 A1 | 1/2010 | Sahni et al. |
| 2010/0025820 A1 | 2/2010 | Suekawa |
| 2010/0030578 A1 | 2/2010 | Siddique et al. |
| 2010/0030649 A1 | 2/2010 | Ubelhor |
| 2010/0030677 A1 | 2/2010 | Melik-Aslanian et al. |
| 2010/0036697 A1 | 2/2010 | Kelnar |
| 2010/0036769 A1 | 2/2010 | Winters et al. |
| 2010/0037299 A1 | 2/2010 | Karasick et al. |
| 2010/0042537 A1 | 2/2010 | Smith et al. |
| 2010/0042542 A1 | 2/2010 | Rose et al. |
| 2010/0042583 A1 | 2/2010 | Gervais |
| 2010/0042732 A1 | 2/2010 | Hopkins |
| 2010/0043055 A1 | 2/2010 | Baumgart |
| 2010/0049803 A1 | 2/2010 | Ogilvie et al. |
| 2010/0058404 A1 | 3/2010 | Rouse |
| 2010/0063906 A1 | 3/2010 | Nelsen et al. |
| 2010/0063942 A1 | 3/2010 | Arnott et al. |
| 2010/0063993 A1 | 3/2010 | Higgins et al. |
| 2010/0076833 A1 | 3/2010 | Nelsen |
| 2010/0076836 A1 | 3/2010 | Giordano et al. |
| 2010/0076966 A1 | 3/2010 | Strutton et al. |
| 2010/0077351 A1 | 3/2010 | Kaulgud et al. |
| 2010/0077483 A1 | 3/2010 | Stolfo et al. |
| 2010/0082445 A1 | 4/2010 | Hodge et al. |
| 2010/0082476 A1 | 4/2010 | Bowman |
| 2010/0083371 A1 | 4/2010 | Bennetts et al. |
| 2010/0088188 A1 | 4/2010 | Kumar et al. |
| 2010/0088233 A1 | 4/2010 | Tattan et al. |
| 2010/0094704 A1 | 4/2010 | Subramanian et al. |
| 2010/0094758 A1 | 4/2010 | Chamberlain et al. |
| 2010/0094768 A1 | 4/2010 | Miltonberger |
| 2010/0094774 A1 | 4/2010 | Jackowitz et al. |
| 2010/0094910 A1 | 4/2010 | Bayliss |
| 2010/0100945 A1 | 4/2010 | Ozzie et al. |
| 2010/0114724 A1 | 5/2010 | Ghosh et al. |
| 2010/0114744 A1 | 5/2010 | Gonen |
| 2010/0114776 A1 | 5/2010 | Weller et al. |
| 2010/0121767 A1 | 5/2010 | Coulter et al. |
| 2010/0122305 A1 | 5/2010 | Moloney |
| 2010/0122324 A1 | 5/2010 | Welingkar et al. |
| 2010/0122333 A1 | 5/2010 | Noe et al. |
| 2010/0130172 A1 | 5/2010 | Vendrow et al. |
| 2010/0136956 A1 | 6/2010 | Drachev et al. |
| 2010/0138298 A1 | 6/2010 | Fitzherald et al. |
| 2010/0145836 A1 | 6/2010 | Baker et al. |
| 2010/0145840 A1 | 6/2010 | Kasower |
| 2010/0153278 A1 | 6/2010 | Farsedakis |
| 2010/0153290 A1 | 6/2010 | Duggan |
| 2010/0153707 A1 | 6/2010 | Lentz, II |
| 2010/0161486 A1 | 6/2010 | Liu et al. |
| 2010/0161816 A1 | 6/2010 | Kraft et al. |
| 2010/0169159 A1 | 7/2010 | Rose et al. |
| 2010/0169264 A1 | 7/2010 | O'Sullivan |
| 2010/0174638 A1 | 7/2010 | Debie et al. |
| 2010/0174813 A1 | 7/2010 | Hildreth et al. |
| 2010/0175119 A1 | 7/2010 | Vitaletti |
| 2010/0179906 A1 | 7/2010 | Hawkes |
| 2010/0185546 A1 | 7/2010 | Pollard |
| 2010/0188684 A1 | 7/2010 | Kumara |
| 2010/0198636 A1 | 8/2010 | Choudhary et al. |
| 2010/0205076 A1 | 8/2010 | Parson et al. |
| 2010/0205662 A1 | 8/2010 | Ibrahim et al. |
| 2010/0211445 A1 | 8/2010 | Bodington |
| 2010/0211636 A1 | 8/2010 | Starkenburg et al. |
| 2010/0212004 A1 | 8/2010 | Fu |
| 2010/0214090 A1 | 8/2010 | Sartin et al. |
| 2010/0215270 A1 | 8/2010 | Manohar et al. |
| 2010/0217837 A1 | 8/2010 | Ansari et al. |
| 2010/0217969 A1 | 8/2010 | Tomkow |
| 2010/0223160 A1 | 9/2010 | Brown |
| 2010/0223184 A1 | 9/2010 | Perlman |
| 2010/0223192 A1 | 9/2010 | Levine et al. |
| 2010/0228658 A1 | 9/2010 | Ketelsen et al. |
| 2010/0229245 A1 | 9/2010 | Singhal |
| 2010/0241493 A1 | 9/2010 | Onischuk |
| 2010/0241535 A1 | 9/2010 | Nightengale et al. |

(56) References Cited

U.S. PATENT DOCUMENTS

| | | |
|---|---|---|
| 2010/0248681 A1 | 9/2010 | Phills |
| 2010/0250338 A1 | 9/2010 | Banerjee et al. |
| 2010/0250410 A1 | 9/2010 | Song et al. |
| 2010/0250411 A1 | 9/2010 | Rodski |
| 2010/0250416 A1 | 9/2010 | Hazlehurst |
| 2010/0250497 A1 | 9/2010 | Redlich et al. |
| 2010/0250509 A1 | 9/2010 | Andersen |
| 2010/0250955 A1 | 9/2010 | Trevithick et al. |
| 2010/0253686 A1 | 10/2010 | Alsbury et al. |
| 2010/0257102 A1 | 10/2010 | Perlman |
| 2010/0257234 A1 | 10/2010 | Caughey |
| 2010/0257577 A1 | 10/2010 | Grandison et al. |
| 2010/0258623 A1 | 10/2010 | Beemer et al. |
| 2010/0258625 A1 | 10/2010 | Stanfield et al. |
| 2010/0259373 A1 | 10/2010 | Chang |
| 2010/0262339 A1 | 10/2010 | Chang |
| 2010/0262535 A1 | 10/2010 | Lent et al. |
| 2010/0262606 A1 | 10/2010 | Bedolla et al. |
| 2010/0262932 A1 | 10/2010 | Pan |
| 2010/0268557 A1 | 10/2010 | Faith et al. |
| 2010/0268660 A1 | 10/2010 | Ekdahl |
| 2010/0268768 A1 | 10/2010 | Kurtenbach et al. |
| 2010/0274815 A1 | 10/2010 | Vanasco |
| 2010/0280914 A1 | 11/2010 | Carlson |
| 2010/0281020 A1 | 11/2010 | Drubner |
| 2010/0293049 A1 | 11/2010 | Maher et al. |
| 2010/0293050 A1 | 11/2010 | Maher et al. |
| 2010/0293058 A1 | 11/2010 | Maher et al. |
| 2010/0293090 A1 | 11/2010 | Domenikos et al. |
| 2010/0299246 A1 | 11/2010 | Chaudhuri et al. |
| 2010/0299262 A1 | 11/2010 | Handler |
| 2010/0306834 A1 | 12/2010 | Grandison et al. |
| 2010/0312691 A1 | 12/2010 | Johnson, Jr. |
| 2010/0323446 A1 | 12/2010 | Barnett et al. |
| 2010/0324999 A1 | 12/2010 | Conway et al. |
| 2010/0325048 A1 | 12/2010 | Carlson et al. |
| 2010/0325442 A1 | 12/2010 | Petrone et al. |
| 2010/0325694 A1 | 12/2010 | Bhagavatula et al. |
| 2010/0332393 A1 | 12/2010 | Weller et al. |
| 2011/0004498 A1 | 1/2011 | Readshaw |
| 2011/0009707 A1 | 1/2011 | Kaundinya et al. |
| 2011/0016042 A1 | 1/2011 | Cho et al. |
| 2011/0016533 A1 | 1/2011 | Zeigler et al. |
| 2011/0023115 A1 | 1/2011 | Wright |
| 2011/0029388 A1 | 2/2011 | Kendall et al. |
| 2011/0029566 A1 | 2/2011 | Grandison et al. |
| 2011/0029660 A1 | 2/2011 | Hopkins |
| 2011/0035305 A1 | 2/2011 | Imrey et al. |
| 2011/0035315 A1 | 2/2011 | Langley |
| 2011/0035452 A1 | 2/2011 | Gittleman |
| 2011/0035788 A1 | 2/2011 | White et al. |
| 2011/0040629 A1 | 2/2011 | Chiu et al. |
| 2011/0040736 A1 | 2/2011 | Kalaboukis |
| 2011/0047606 A1 | 2/2011 | Blomquist |
| 2011/0054981 A1 | 3/2011 | Faith et al. |
| 2011/0060672 A1 | 3/2011 | Kasower |
| 2011/0060905 A1 | 3/2011 | Stack et al. |
| 2011/0066495 A1 | 3/2011 | Ayloo et al. |
| 2011/0066618 A1 | 3/2011 | Sigurbjornsson et al. |
| 2011/0066695 A1 | 3/2011 | Hopkins |
| 2011/0071950 A1 | 3/2011 | Ivanovic |
| 2011/0078073 A1 | 3/2011 | Annappindi et al. |
| 2011/0082768 A1 | 4/2011 | Eisen |
| 2011/0083181 A1 | 4/2011 | Nazarov |
| 2011/0107265 A1 | 5/2011 | Buchanan et al. |
| 2011/0107400 A1 | 5/2011 | Shankaranarayanan et al. |
| 2011/0112899 A1 | 5/2011 | Strutton et al. |
| 2011/0113084 A1 | 5/2011 | Ramnani |
| 2011/0113086 A1 | 5/2011 | Long et al. |
| 2011/0113096 A1 | 5/2011 | Long et al. |
| 2011/0119155 A1 | 5/2011 | Hammad et al. |
| 2011/0119169 A1 | 5/2011 | Passero et al. |
| 2011/0119765 A1 | 5/2011 | Hering et al. |
| 2011/0125595 A1 | 5/2011 | Neal et al. |
| 2011/0125924 A1 | 5/2011 | McAleer |
| 2011/0126024 A1 | 5/2011 | Beatson et al. |
| 2011/0126275 A1 | 5/2011 | Anderson et al. |
| 2011/0131096 A1 | 6/2011 | Frew et al. |
| 2011/0131123 A1 | 6/2011 | Griffin et al. |
| 2011/0131131 A1 | 6/2011 | Griffin et al. |
| 2011/0137760 A1 | 6/2011 | Rudie et al. |
| 2011/0137765 A1 | 6/2011 | Nonaka |
| 2011/0137789 A1 | 6/2011 | Kortina et al. |
| 2011/0142213 A1 | 6/2011 | Baniak et al. |
| 2011/0143711 A1 | 6/2011 | Hirson et al. |
| 2011/0145064 A1 | 6/2011 | Anderson et al. |
| 2011/0145899 A1 | 6/2011 | Cao et al. |
| 2011/0148625 A1 | 6/2011 | Velusamy |
| 2011/0161155 A1 | 6/2011 | Wilhem et al. |
| 2011/0161218 A1 | 6/2011 | Swift |
| 2011/0164746 A1 | 7/2011 | Nice et al. |
| 2011/0166988 A1 | 7/2011 | Coulter |
| 2011/0167011 A1 | 7/2011 | Paltenghe et al. |
| 2011/0173681 A1 | 7/2011 | Qureshi et al. |
| 2011/0178841 A1 | 7/2011 | Rane et al. |
| 2011/0178899 A1 | 7/2011 | Huszar |
| 2011/0178922 A1 | 7/2011 | Imrey et al. |
| 2011/0179139 A1 | 7/2011 | Starkenburg et al. |
| 2011/0184780 A1 | 7/2011 | Alderson et al. |
| 2011/0184838 A1 | 7/2011 | Winters et al. |
| 2011/0193704 A1 | 8/2011 | Harper et al. |
| 2011/0196791 A1 | 8/2011 | Dominguez |
| 2011/0202474 A1 | 8/2011 | Mele et al. |
| 2011/0208601 A1 | 8/2011 | Ferguson et al. |
| 2011/0211445 A1 | 9/2011 | Chen |
| 2011/0213670 A1 | 9/2011 | Strutton et al. |
| 2011/0214187 A1 | 9/2011 | Wittenstein et al. |
| 2011/0219421 A1 | 9/2011 | Ullman et al. |
| 2011/0238566 A1 | 9/2011 | Santos |
| 2011/0243406 A1 | 10/2011 | Chandler |
| 2011/0252071 A1 | 10/2011 | Cidon |
| 2011/0255688 A1 | 10/2011 | Spalink et al. |
| 2011/0258050 A1 | 10/2011 | Chan et al. |
| 2011/0260832 A1 | 10/2011 | Ross et al. |
| 2011/0264531 A1 | 10/2011 | Bhatia et al. |
| 2011/0264566 A1 | 10/2011 | Brown |
| 2011/0264581 A1 | 10/2011 | Clyne |
| 2011/0270618 A1 | 11/2011 | Banerjee et al. |
| 2011/0270727 A1 | 11/2011 | Kasower |
| 2011/0270754 A1 | 11/2011 | Kelly et al. |
| 2011/0271329 A1 | 11/2011 | Hulten et al. |
| 2011/0276382 A1 | 11/2011 | Ramchandani et al. |
| 2011/0276396 A1 | 11/2011 | Rathod |
| 2011/0276604 A1 | 11/2011 | Hom et al. |
| 2011/0276687 A1 | 11/2011 | Tarquini et al. |
| 2011/0282711 A1 | 11/2011 | Freishtat et al. |
| 2011/0282783 A1 | 11/2011 | Ferguson et al. |
| 2011/0282943 A1 | 11/2011 | Anderson et al. |
| 2011/0289151 A1 | 11/2011 | Hopkins |
| 2011/0289209 A1 | 11/2011 | Hopkins |
| 2011/0296003 A1 | 12/2011 | McCann et al. |
| 2011/0302083 A1 | 12/2011 | Bhinder |
| 2011/0302653 A1 | 12/2011 | Frantz et al. |
| 2011/0307397 A1 | 12/2011 | Benmbarek |
| 2011/0307434 A1 | 12/2011 | Rostampour et al. |
| 2011/0307474 A1 | 12/2011 | Hom et al. |
| 2011/0307494 A1 | 12/2011 | Snow |
| 2011/0307938 A1 | 12/2011 | Reeves, Jr. et al. |
| 2011/0307957 A1 | 12/2011 | Barcelo et al. |
| 2011/0313915 A1 | 12/2011 | Tang |
| 2011/0314100 A1 | 12/2011 | Hopkins |
| 2011/0314383 A1 | 12/2011 | Abdo et al. |
| 2011/0320582 A1 | 12/2011 | Lewis |
| 2011/0321137 A1 | 12/2011 | Iida et al. |
| 2012/0005070 A1 | 1/2012 | McFall et al. |
| 2012/0005221 A1 | 1/2012 | Ickman et al. |
| 2012/0005542 A1 | 1/2012 | Petersen et al. |
| 2012/0010927 A1 | 1/2012 | Attenberg et al. |
| 2012/0011056 A1 | 1/2012 | Ward et al. |
| 2012/0011063 A1 | 1/2012 | Killian et al. |
| 2012/0011158 A1 | 1/2012 | Avner et al. |
| 2012/0011432 A1 | 1/2012 | Strutton |
| 2012/0015717 A1 | 1/2012 | Mosites et al. |
| 2012/0016948 A1 | 1/2012 | Sinha |

(56) References Cited

U.S. PATENT DOCUMENTS

| | | |
|---|---|---|
| 2012/0018506 A1 | 1/2012 | Hammad et al. |
| 2012/0022990 A1 | 1/2012 | Kasower |
| 2012/0029956 A1 | 2/2012 | Ghosh et al. |
| 2012/0030216 A1 | 2/2012 | Churl et al. |
| 2012/0030771 A1 | 2/2012 | Pierson et al. |
| 2012/0036065 A1 | 2/2012 | Orttung et al. |
| 2012/0036127 A1 | 2/2012 | Work et al. |
| 2012/0036565 A1 | 2/2012 | Gamez et al. |
| 2012/0042237 A1 | 2/2012 | Armandpour et al. |
| 2012/0047174 A1 | 2/2012 | Avner et al. |
| 2012/0047219 A1 | 2/2012 | Feng et al. |
| 2012/0047423 A1 | 2/2012 | Tomkow |
| 2012/0054088 A1 | 3/2012 | Edrington et al. |
| 2012/0054592 A1 | 3/2012 | Jaffe et al. |
| 2012/0060105 A1 | 3/2012 | Brown et al. |
| 2012/0066044 A1 | 3/2012 | Honnef et al. |
| 2012/0066065 A1 | 3/2012 | Switzer |
| 2012/0066106 A1 | 3/2012 | Papadimitriou |
| 2012/0072382 A1 | 3/2012 | Pearson et al. |
| 2012/0072464 A1 | 3/2012 | Cohen |
| 2012/0078766 A1 | 3/2012 | Rose et al. |
| 2012/0078932 A1* | 3/2012 | Skurtovich, Jr. ...... G06Q 40/02 707/E17.014 |
| 2012/0079585 A1 | 3/2012 | Chan et al. |
| 2012/0079598 A1 | 3/2012 | Brock et al. |
| 2012/0084866 A1 | 4/2012 | Stolfo |
| 2012/0089438 A1 | 4/2012 | Tavares et al. |
| 2012/0095927 A1 | 4/2012 | Hirtenstein et al. |
| 2012/0101938 A1 | 4/2012 | Kasower |
| 2012/0101939 A1 | 4/2012 | Kasower |
| 2012/0106801 A1 | 5/2012 | Jackson |
| 2012/0108274 A1 | 5/2012 | Acebo Ruiz et al. |
| 2012/0109752 A1 | 5/2012 | Strutton et al. |
| 2012/0109990 A1 | 5/2012 | Yamasaki |
| 2012/0110467 A1 | 5/2012 | Blake et al. |
| 2012/0110677 A1 | 5/2012 | Abendroth et al. |
| 2012/0116913 A1 | 5/2012 | Goolkasian |
| 2012/0116969 A1 | 5/2012 | Kumar et al. |
| 2012/0117509 A1 | 5/2012 | Powell et al. |
| 2012/0117629 A1 | 5/2012 | Miyazawa et al. |
| 2012/0124033 A1 | 5/2012 | Gabriel et al. |
| 2012/0124498 A1 | 5/2012 | Santoro et al. |
| 2012/0130898 A1 | 5/2012 | Snyder et al. |
| 2012/0131009 A1 | 5/2012 | Nath et al. |
| 2012/0131656 A1 | 5/2012 | Slaton et al. |
| 2012/0135705 A1 | 5/2012 | Thaker |
| 2012/0136763 A1 | 5/2012 | Megdal et al. |
| 2012/0136774 A1 | 5/2012 | Imrey et al. |
| 2012/0144461 A1 | 6/2012 | Rathbun |
| 2012/0151045 A1 | 6/2012 | Anakata et al. |
| 2012/0151046 A1 | 6/2012 | Weiss et al. |
| 2012/0158460 A1 | 6/2012 | Kruger et al. |
| 2012/0158562 A1 | 6/2012 | Kassir |
| 2012/0158575 A1 | 6/2012 | Chaudhuri et al. |
| 2012/0158654 A1 | 6/2012 | Behren et al. |
| 2012/0173339 A1 | 7/2012 | Flynt et al. |
| 2012/0173417 A1 | 7/2012 | Lohman et al. |
| 2012/0173563 A1 | 7/2012 | Griffin et al. |
| 2012/0179536 A1 | 7/2012 | Kalb et al. |
| 2012/0185515 A1 | 7/2012 | Ferrel et al. |
| 2012/0191596 A1 | 7/2012 | Kremen et al. |
| 2012/0191610 A1 | 7/2012 | Prasad |
| 2012/0191693 A1 | 7/2012 | Alexander |
| 2012/0195412 A1 | 8/2012 | Smith |
| 2012/0198556 A1 | 8/2012 | Patel et al. |
| 2012/0203733 A1 | 8/2012 | Zhang |
| 2012/0215682 A1 | 8/2012 | Lent et al. |
| 2012/0215719 A1 | 8/2012 | Verlander |
| 2012/0216125 A1 | 8/2012 | Pierce |
| 2012/0221467 A1 | 8/2012 | Hamzeh |
| 2012/0226916 A1 | 9/2012 | Hahn et al. |
| 2012/0232958 A1 | 9/2012 | Silbert |
| 2012/0235897 A1 | 9/2012 | Hirota |
| 2012/0239417 A1 | 9/2012 | Pourfallah et al. |
| 2012/0239497 A1 | 9/2012 | Nuzzi |
| 2012/0240223 A1 | 9/2012 | Tu |
| 2012/0242473 A1 | 9/2012 | Choi |
| 2012/0246060 A1 | 9/2012 | Conyack, Jr. et al. |
| 2012/0246092 A1 | 9/2012 | Stibel et al. |
| 2012/0246093 A1 | 9/2012 | Stibel et al. |
| 2012/0246730 A1 | 9/2012 | Raad |
| 2012/0253852 A1 | 10/2012 | Pourfallah et al. |
| 2012/0262386 A1 | 10/2012 | Kwon et al. |
| 2012/0262472 A1 | 10/2012 | Garr et al. |
| 2012/0265607 A1 | 10/2012 | Belwadi |
| 2012/0271660 A1 | 10/2012 | Harris et al. |
| 2012/0271712 A1 | 10/2012 | Katzin et al. |
| 2012/0278217 A1 | 11/2012 | Sui et al. |
| 2012/0278226 A1 | 11/2012 | Kolo |
| 2012/0278227 A1 | 11/2012 | Kolo et al. |
| 2012/0278767 A1 | 11/2012 | Stibel et al. |
| 2012/0284118 A1 | 11/2012 | Mamich, Jr. et al. |
| 2012/0284280 A1 | 11/2012 | Kumar |
| 2012/0290660 A1 | 11/2012 | Rao et al. |
| 2012/0290740 A1 | 11/2012 | Tewari et al. |
| 2012/0296804 A1 | 11/2012 | Stibel et al. |
| 2012/0297484 A1 | 11/2012 | Srivastava |
| 2012/0303514 A1 | 11/2012 | Kasower |
| 2012/0317013 A1 | 12/2012 | Luk et al. |
| 2012/0317014 A1 | 12/2012 | Cerise et al. |
| 2012/0321202 A1 | 12/2012 | Fertik et al. |
| 2012/0323695 A1 | 12/2012 | Stibel |
| 2012/0323717 A1 | 12/2012 | Kirsch |
| 2012/0324388 A1 | 12/2012 | Rao et al. |
| 2012/0330689 A1 | 12/2012 | McLaughlin et al. |
| 2012/0331557 A1 | 12/2012 | Washington |
| 2013/0004033 A1 | 1/2013 | Trugenberger et al. |
| 2013/0006843 A1 | 1/2013 | Tralvex |
| 2013/0006844 A1 | 1/2013 | Kremen |
| 2013/0007012 A1 | 1/2013 | Selkowe Fertik et al. |
| 2013/0007014 A1 | 1/2013 | Fertik et al. |
| 2013/0007891 A1 | 1/2013 | Mogaki |
| 2013/0013513 A1 | 1/2013 | Ledbetter et al. |
| 2013/0013553 A1 | 1/2013 | Stibel et al. |
| 2013/0018798 A1 | 1/2013 | Scipioni |
| 2013/0018811 A1 | 1/2013 | Britti et al. |
| 2013/0018838 A1 | 1/2013 | Parnaby et al. |
| 2013/0018877 A1 | 1/2013 | Gabriel et al. |
| 2013/0018892 A1 | 1/2013 | Castellanos et al. |
| 2013/0018957 A1 | 1/2013 | Parnaby et al. |
| 2013/0024367 A1 | 1/2013 | Bellefeuille et al. |
| 2013/0024520 A1 | 1/2013 | Siminoff |
| 2013/0024813 A1 | 1/2013 | Schnorr et al. |
| 2013/0030826 A1 | 1/2013 | Blom |
| 2013/0031105 A1 | 1/2013 | Stibel et al. |
| 2013/0031109 A1 | 1/2013 | Roulson et al. |
| 2013/0031113 A1 | 1/2013 | Feng et al. |
| 2013/0031624 A1 | 1/2013 | Britti et al. |
| 2013/0036466 A1 | 2/2013 | Penta et al. |
| 2013/0040619 A1 | 2/2013 | Grube et al. |
| 2013/0041701 A1 | 2/2013 | Roth |
| 2013/0041798 A1 | 2/2013 | Unger |
| 2013/0041810 A1 | 2/2013 | Murrell et al. |
| 2013/0041949 A1 | 2/2013 | Biesecker et al. |
| 2013/0054357 A1 | 2/2013 | Mager et al. |
| 2013/0061335 A1 | 3/2013 | Schwabe |
| 2013/0066716 A1 | 3/2013 | Chen et al. |
| 2013/0066775 A1 | 3/2013 | Milam |
| 2013/0066884 A1 | 3/2013 | Kast et al. |
| 2013/0066922 A1 | 3/2013 | Jang et al. |
| 2013/0067582 A1 | 3/2013 | Donovan et al. |
| 2013/0073366 A1 | 3/2013 | Heath |
| 2013/0080322 A1 | 3/2013 | Adolphe |
| 2013/0080467 A1 | 3/2013 | Carson et al. |
| 2013/0085804 A1 | 4/2013 | Leff et al. |
| 2013/0085894 A1 | 4/2013 | Chan et al. |
| 2013/0085939 A1 | 4/2013 | Colak et al. |
| 2013/0085953 A1 | 4/2013 | Bhola et al. |
| 2013/0086075 A1 | 4/2013 | Scott et al. |
| 2013/0086186 A1 | 4/2013 | Tomkow |
| 2013/0086654 A1 | 4/2013 | Tomkow |
| 2013/0090982 A1 | 4/2013 | Ross |
| 2013/0103464 A1 | 4/2013 | Kuznetsov |
| 2013/0103571 A1 | 4/2013 | Chung et al. |

(56) References Cited

U.S. PATENT DOCUMENTS

| | | |
|---|---|---|
| 2013/0104216 A1 | 4/2013 | Dennis et al. |
| 2013/0110557 A1 | 5/2013 | Kasower |
| 2013/0110565 A1 | 5/2013 | Means et al. |
| 2013/0110585 A1 | 5/2013 | Nesbitt et al. |
| 2013/0110678 A1 | 5/2013 | Vigier et al. |
| 2013/0111436 A1 | 5/2013 | Phan et al. |
| 2013/0117072 A1 | 5/2013 | Nish |
| 2013/0117087 A1 | 5/2013 | Coppinger |
| 2013/0117387 A1 | 5/2013 | Tomkow |
| 2013/0124263 A1 | 5/2013 | Amaro et al. |
| 2013/0124392 A1 | 5/2013 | Achanta et al. |
| 2013/0124855 A1 | 5/2013 | Varadarajan et al. |
| 2013/0125010 A1 | 5/2013 | Strandell |
| 2013/0132151 A1 | 5/2013 | Stibel et al. |
| 2013/0139229 A1 | 5/2013 | Fried et al. |
| 2013/0159168 A1 | 6/2013 | Evans |
| 2013/0159411 A1 | 6/2013 | Bowen |
| 2013/0173447 A1 | 7/2013 | Rothschild |
| 2013/0173449 A1 | 7/2013 | Ng et al. |
| 2013/0173451 A1 | 7/2013 | Kornegay et al. |
| 2013/0173481 A1 | 7/2013 | Hirtenstein et al. |
| 2013/0179338 A1 | 7/2013 | Evans |
| 2013/0179955 A1 | 7/2013 | Bekker et al. |
| 2013/0185210 A1 | 7/2013 | Dodson et al. |
| 2013/0185293 A1 | 7/2013 | Boback |
| 2013/0187923 A1 | 7/2013 | Yoshimoto et al. |
| 2013/0198525 A1 | 8/2013 | Spies et al. |
| 2013/0204762 A1 | 8/2013 | Harris et al. |
| 2013/0205135 A1 | 8/2013 | Lutz |
| 2013/0211986 A1 | 8/2013 | Debie et al. |
| 2013/0212187 A1 | 8/2013 | Mortazavi et al. |
| 2013/0212661 A1 | 8/2013 | Neafsey et al. |
| 2013/0218751 A1 | 8/2013 | Chaudhuri et al. |
| 2013/0226783 A1 | 8/2013 | Haggerty et al. |
| 2013/0238387 A1 | 9/2013 | Stibel et al. |
| 2013/0246150 A1 | 9/2013 | Ovick et al. |
| 2013/0246273 A1 | 9/2013 | Ovick et al. |
| 2013/0246528 A1 | 9/2013 | Ogura |
| 2013/0254008 A1 | 9/2013 | Ovick et al. |
| 2013/0254096 A1 | 9/2013 | Serio et al. |
| 2013/0262226 A1 | 10/2013 | LaChapelle et al. |
| 2013/0267171 A1 | 10/2013 | Sarkar et al. |
| 2013/0268333 A1 | 10/2013 | Ovick et al. |
| 2013/0268357 A1 | 10/2013 | Heath |
| 2013/0271272 A1 | 10/2013 | Dhesi et al. |
| 2013/0275762 A1 | 10/2013 | Tomkow |
| 2013/0278515 A1 | 10/2013 | Kikuchi |
| 2013/0279676 A1 | 10/2013 | Baniak et al. |
| 2013/0282461 A1 | 10/2013 | Ovick et al. |
| 2013/0282819 A1 | 10/2013 | Mehta et al. |
| 2013/0290097 A1 | 10/2013 | Balestrieri et al. |
| 2013/0290164 A1 | 10/2013 | Salm |
| 2013/0293363 A1 | 11/2013 | Plymouth |
| 2013/0297499 A1 | 11/2013 | Mukherjee |
| 2013/0298238 A1 | 11/2013 | Shah et al. |
| 2013/0318569 A1 | 11/2013 | Canning et al. |
| 2013/0332338 A1 | 12/2013 | Yan et al. |
| 2013/0332341 A1 | 12/2013 | Papadimitriou |
| 2013/0332342 A1 | 12/2013 | Kasower |
| 2013/0332352 A1 | 12/2013 | Imrey et al. |
| 2013/0332467 A1 | 12/2013 | Bornea et al. |
| 2013/0339141 A1 | 12/2013 | Stibel et al. |
| 2013/0339217 A1 | 12/2013 | Breslow et al. |
| 2013/0339249 A1 | 12/2013 | Weller et al. |
| 2013/0346331 A1 | 12/2013 | Giovannetti et al. |
| 2013/0347059 A1 | 12/2013 | Fong et al. |
| 2014/0012733 A1 | 1/2014 | Vidal |
| 2014/0012737 A1 | 1/2014 | Evans |
| 2014/0013396 A1 | 1/2014 | Field-Eliot et al. |
| 2014/0019348 A1 | 1/2014 | Daley |
| 2014/0025475 A1 | 1/2014 | Burke |
| 2014/0025562 A1 | 1/2014 | Rothrock et al. |
| 2014/0032265 A1 | 1/2014 | Paprocki et al. |
| 2014/0032300 A1 | 1/2014 | Zhang et al. |
| 2014/0032723 A1 | 1/2014 | Nema |
| 2014/0033280 A1 | 1/2014 | Nimashakavi et al. |
| 2014/0040051 A1 | 2/2014 | Ovick et al. |
| 2014/0040135 A1 | 2/2014 | Ovick et al. |
| 2014/0040182 A1 | 2/2014 | Gilder et al. |
| 2014/0046872 A1 | 2/2014 | Arnott et al. |
| 2014/0051464 A1 | 2/2014 | Ryan et al. |
| 2014/0052732 A1 | 2/2014 | Softky |
| 2014/0061302 A1 | 3/2014 | Hammad |
| 2014/0074689 A1 | 3/2014 | Lund et al. |
| 2014/0089166 A1 | 3/2014 | Padawer et al. |
| 2014/0089167 A1 | 3/2014 | Kasower |
| 2014/0089191 A1 | 3/2014 | Brown |
| 2014/0095640 A1 | 4/2014 | Stibel et al. |
| 2014/0096249 A1 | 4/2014 | Dupont et al. |
| 2014/0098142 A1 | 4/2014 | Lee et al. |
| 2014/0098229 A1 | 4/2014 | Lu et al. |
| 2014/0110477 A1 | 4/2014 | Hammad |
| 2014/0122354 A1 | 5/2014 | Stibel et al. |
| 2014/0129942 A1 | 5/2014 | Rathod |
| 2014/0136422 A1 | 5/2014 | Jung et al. |
| 2014/0156500 A1 | 6/2014 | Lassen et al. |
| 2014/0156501 A1 | 6/2014 | Howe |
| 2014/0156503 A1 | 6/2014 | Lassen et al. |
| 2014/0162611 A1 | 6/2014 | Mezhibovsky et al. |
| 2014/0164112 A1 | 6/2014 | Kala et al. |
| 2014/0164398 A1 | 6/2014 | Smith et al. |
| 2014/0164519 A1 | 6/2014 | Shah |
| 2014/0172681 A1 | 6/2014 | Lamp et al. |
| 2014/0172687 A1 | 6/2014 | Chirehdast |
| 2014/0173732 A1 | 6/2014 | Stibel |
| 2014/0180919 A1 | 6/2014 | Brown |
| 2014/0181285 A1 | 6/2014 | Stevens et al. |
| 2014/0201007 A1 | 7/2014 | Stack et al. |
| 2014/0201100 A1 | 7/2014 | Rellas et al. |
| 2014/0237377 A1 | 8/2014 | Meissner |
| 2014/0244353 A1 | 8/2014 | Winters |
| 2014/0258083 A1 | 9/2014 | Achanta et al. |
| 2014/0258084 A1 | 9/2014 | Padawer et al. |
| 2014/0279329 A1 | 9/2014 | Dancel |
| 2014/0279382 A1 | 9/2014 | Drakeley et al. |
| 2014/0279391 A1 | 9/2014 | Gallo et al. |
| 2014/0279467 A1 | 9/2014 | Chapa et al. |
| 2014/0280945 A1 | 9/2014 | Lunt |
| 2014/0282977 A1 | 9/2014 | Madhu et al. |
| 2014/0283123 A1 | 9/2014 | Lonstein et al. |
| 2014/0289812 A1 | 9/2014 | Wang et al. |
| 2014/0298485 A1 | 10/2014 | Gardner |
| 2014/0304263 A1 | 10/2014 | Vaitheeswaran et al. |
| 2014/0310151 A1 | 10/2014 | Shishkov et al. |
| 2014/0316969 A1 | 10/2014 | Imrey |
| 2014/0317023 A1 | 10/2014 | Kim |
| 2014/0317716 A1 | 10/2014 | Chao et al. |
| 2014/0324655 A1 | 10/2014 | Kolathur |
| 2014/0331282 A1 | 11/2014 | Tkachev |
| 2014/0372367 A1 | 12/2014 | McLean et al. |
| 2014/0379554 A1 | 12/2014 | Grossman et al. |
| 2015/0026060 A1 | 1/2015 | Krietzman et al. |
| 2015/0066772 A1 | 3/2015 | Griffin et al. |
| 2015/0067341 A1 | 3/2015 | Deen et al. |
| 2015/0089569 A1 | 3/2015 | Sondhi et al. |
| 2015/0127490 A1 | 5/2015 | Puertas |
| 2015/0134506 A1 | 5/2015 | King et al. |
| 2015/0135305 A1 | 5/2015 | Cabrera et al. |
| 2015/0142595 A1 | 5/2015 | Acuña-Rohter |
| 2015/0161738 A1 | 6/2015 | Stempora |
| 2015/0178829 A1 | 6/2015 | Weiss |
| 2015/0180870 A1 | 6/2015 | Zhang et al. |
| 2015/0199667 A1 | 7/2015 | Fernando et al. |
| 2015/0199668 A1 | 7/2015 | Fernando et al. |
| 2015/0199757 A1 | 7/2015 | Lindholme et al. |
| 2015/0200948 A1 | 7/2015 | Cairns et al. |
| 2015/0249655 A1 | 9/2015 | Lunt |
| 2015/0254329 A1 | 9/2015 | Agarwal et al. |
| 2015/0254658 A1 | 9/2015 | Bondesen et al. |
| 2015/0262246 A1 | 9/2015 | Stack et al. |
| 2015/0262249 A1 | 9/2015 | Wical |
| 2015/0278277 A1* | 10/2015 | Agrawal ............ G06K 9/00496 |
| | | 707/746 |
| 2015/0287091 A1 | 10/2015 | Koran |

(56) References Cited

U.S. PATENT DOCUMENTS

| | | |
|---|---|---|
| 2015/0302521 A1 | 10/2015 | Bartmann |
| 2015/0310543 A1 | 10/2015 | DeBie |
| 2015/0324920 A1 | 11/2015 | Wilson et al. |
| 2015/0350186 A1 | 12/2015 | Chan et al. |
| 2016/0004728 A1 | 1/2016 | Balet et al. |
| 2016/0005020 A1 | 1/2016 | Fernando et al. |
| 2016/0027008 A1 | 1/2016 | John |
| 2016/0048700 A1 | 2/2016 | Stransky-Heilkron |
| 2016/0050198 A1 | 2/2016 | Thibadeau Sr. et al. |
| 2016/0065563 A1 | 3/2016 | Broadbent et al. |
| 2016/0088465 A1 | 3/2016 | Golla |
| 2016/0142532 A1 | 5/2016 | Bostick |
| 2016/0226879 A1 | 8/2016 | Chan et al. |
| 2016/0227037 A1 | 8/2016 | Roybal et al. |
| 2016/0232546 A1 | 8/2016 | Ranft et al. |
| 2016/0232605 A1 | 8/2016 | Zhang |
| 2016/0275476 A1 | 9/2016 | Artman et al. |
| 2016/0283740 A1 | 9/2016 | Roundtree |
| 2016/0328476 A1 | 11/2016 | Chang et al. |
| 2016/0337369 A1 | 11/2016 | Sanso |
| 2016/0342999 A1 | 11/2016 | Rouston et al. |
| 2017/0061436 A1 | 3/2017 | Liu et al. |
| 2017/0098096 A1 | 4/2017 | Redberg |
| 2017/0132700 A1 | 5/2017 | Kazerani et al. |
| 2017/0161486 A1 | 6/2017 | Jeon et al. |
| 2017/0177809 A1 | 6/2017 | Bull et al. |
| 2017/0186012 A1 | 6/2017 | McNeal |
| 2017/0200223 A1 | 7/2017 | Kasower |
| 2017/0221121 A1 | 8/2017 | Davis et al. |
| 2017/0249481 A1 | 8/2017 | Edison |
| 2017/0262821 A1 | 9/2017 | Imrey et al. |
| 2017/0324749 A1 | 11/2017 | Bhargava et al. |
| 2017/0331832 A1 | 11/2017 | Lander et al. |
| 2017/0337549 A1 | 11/2017 | Wong |
| 2017/0337557 A1 | 11/2017 | Durney et al. |
| 2017/0352014 A1 | 12/2017 | Smith et al. |
| 2017/0352186 A1 | 12/2017 | Dauphiny et al. |
| 2017/0357971 A1 | 12/2017 | Pitz et al. |
| 2018/0040063 A1 | 2/2018 | Buechler et al. |
| 2018/0041336 A1 | 2/2018 | Keshava et al. |
| 2018/0075527 A1 | 3/2018 | Nagla et al. |
| 2018/0077142 A1 | 3/2018 | Thakkar |
| 2018/0082372 A1 | 3/2018 | Diana |
| 2018/0083915 A1 | 3/2018 | Medam et al. |
| 2018/0089379 A1 | 3/2018 | Collins et al. |
| 2018/0150599 A1 | 5/2018 | Valdes et al. |
| 2018/0164877 A1 | 6/2018 | Miller et al. |
| 2018/0176267 A1 | 6/2018 | Malatesha et al. |
| 2018/0204279 A1 | 7/2018 | Painter et al. |
| 2018/0218069 A1 | 8/2018 | Rege et al. |
| 2018/0218448 A1 | 8/2018 | Thomas et al. |
| 2018/0227292 A1 | 8/2018 | Golshan et al. |
| 2018/0232433 A1 | 8/2018 | Kanvinde |
| 2018/0253702 A1 | 9/2018 | Dowding |
| 2018/0276222 A1 | 9/2018 | Belknap et al. |
| 2018/0285549 A1 | 10/2018 | Sonkar et al. |
| 2018/0330516 A1 | 11/2018 | Baca et al. |
| 2018/0337914 A1 | 11/2018 | Mohamad Abdul et al. |
| 2018/0349992 A1 | 12/2018 | Dean et al. |
| 2018/0365690 A1 | 12/2018 | Ovick et al. |
| 2018/0375791 A1 | 12/2018 | Kaladgi et al. |
| 2019/0019185 A1 | 1/2019 | Chitalia et al. |
| 2019/0034625 A1 | 1/2019 | Ford et al. |
| 2019/0051305 A1 | 2/2019 | Liddell et al. |
| 2019/0065516 A1 | 2/2019 | Barker |
| 2019/0066203 A1 | 2/2019 | Smith et al. |
| 2019/0073676 A1 | 3/2019 | Wang |
| 2019/0095516 A1 | 3/2019 | Srinivasan et al. |
| 2019/0102438 A1 | 4/2019 | Murray et al. |
| 2019/0147366 A1 | 5/2019 | Sankaran et al. |
| 2019/0164173 A1 | 5/2019 | Liu et al. |
| 2019/0188717 A1 | 6/2019 | Putnam et al. |
| 2019/0188781 A1 | 6/2019 | O'Brien et al. |
| 2019/0197528 A1 | 6/2019 | Dean et al. |
| 2019/0228173 A1 | 7/2019 | Gupta et al. |
| 2019/0228178 A1 | 7/2019 | Sharma et al. |
| 2019/0258818 A1 | 8/2019 | Yu et al. |
| 2019/0295165 A1 | 9/2019 | Kapczynski et al. |
| 2019/0296804 A1 | 9/2019 | Eitan et al. |
| 2019/0318122 A1 | 10/2019 | Hockey et al. |
| 2019/0332400 A1 | 10/2019 | Spoor et al. |
| 2019/0349360 A1 | 11/2019 | Yeddula et al. |
| 2019/0355362 A1 | 11/2019 | Brown et al. |
| 2019/0356672 A1 | 11/2019 | Bondugula et al. |
| 2020/0034927 A1 | 1/2020 | Smith et al. |
| 2020/0051115 A1 | 2/2020 | Lawrence et al. |
| 2020/0051527 A1 | 2/2020 | Ngo |
| 2020/0074100 A1 | 3/2020 | Raneri et al. |
| 2020/0074109 A1 | 3/2020 | Pieniazek et al. |
| 2020/0074541 A1 | 3/2020 | Finneran et al. |
| 2020/0074745 A1 | 3/2020 | Lyren |
| 2020/0076813 A1 | 3/2020 | Felice-Steele et al. |
| 2020/0090265 A1 | 3/2020 | Quinn et al. |
| 2020/0104834 A1 | 4/2020 | Pontious et al. |
| 2020/0106764 A1 | 4/2020 | Hockey et al. |
| 2020/0106765 A1 | 4/2020 | Hockey et al. |
| 2020/0126126 A1 | 4/2020 | Briancon et al. |
| 2020/0137080 A1 | 4/2020 | Bloomquist et al. |
| 2020/0143384 A1 | 5/2020 | Koontz et al. |
| 2020/0160372 A1 | 5/2020 | Andrick |
| 2020/0160472 A1 | 5/2020 | Kapczynski |
| 2020/0162443 A1 | 5/2020 | Poschel et al. |
| 2020/0174010 A1 | 6/2020 | Pfeiffer et al. |
| 2020/0193413 A1 | 6/2020 | Jangama et al. |
| 2020/0193423 A1 | 6/2020 | Jangama et al. |
| 2020/0201878 A1 | 6/2020 | Putnam et al. |
| 2020/0202425 A1 | 6/2020 | Taylor-Shoff et al. |
| 2020/0205002 A1 | 6/2020 | Talwar |
| 2020/0210492 A1 | 7/2020 | Chang et al. |
| 2020/0211099 A1 | 7/2020 | Smith et al. |
| 2020/0213206 A1 | 7/2020 | Bracken et al. |
| 2020/0228321 A1 | 7/2020 | Krishnamacharya et al. |
| 2020/0265155 A1 | 8/2020 | Dong et al. |
| 2020/0279053 A1 | 9/2020 | Jones et al. |
| 2020/0285679 A1 | 9/2020 | Chen et al. |
| 2020/0293684 A1 | 9/2020 | Harris et al. |
| 2020/0304501 A1 | 9/2020 | Fan |
| 2020/0311168 A1 | 10/2020 | Rokos |
| 2020/0314088 A1 | 10/2020 | Feijoo et al. |
| 2020/0320511 A1 | 10/2020 | Anderson et al. |
| 2020/0327150 A1 | 10/2020 | Kunjur et al. |
| 2020/0327560 A1 | 10/2020 | Anderson et al. |
| 2020/0334349 A1 | 10/2020 | Billman et al. |
| 2020/0342039 A1 | 10/2020 | Bakir et al. |
| 2020/0342527 A1 | 10/2020 | Kasower |
| 2020/0342557 A1 | 10/2020 | Chapa et al. |
| 2020/0364246 A1 | 11/2020 | Farrell |
| 2020/0364785 A1 | 11/2020 | Olson et al. |
| 2020/0372173 A1 | 11/2020 | Burger et al. |
| 2020/0372535 A1 | 11/2020 | Walz et al. |
| 2020/0380112 A1 | 12/2020 | Allen |
| 2020/0380509 A1 | 12/2020 | Billman et al. |
| 2020/0380599 A1 | 12/2020 | Wasser et al. |
| 2020/0387634 A1 | 12/2020 | Jones et al. |
| 2020/0389461 A1 | 12/2020 | Felice-Steele et al. |
| 2020/0394331 A1 | 12/2020 | Talwar |
| 2020/0394675 A1 | 12/2020 | Bradford |
| 2020/0402159 A1 | 12/2020 | Arnold et al. |
| 2020/0403992 A1 | 12/2020 | Huffman et al. |
| 2021/0004373 A1 | 1/2021 | Sankaran et al. |
| 2021/0004703 A1 | 1/2021 | Zoldi et al. |
| 2021/0012312 A1 | 1/2021 | Bradstreet |
| 2021/0027357 A1 | 1/2021 | Bonfigli et al. |
| 2021/0034613 A1 | 2/2021 | Ng et al. |
| 2021/0042366 A1 | 2/2021 | Hicklin et al. |
| 2021/0064725 A1 | 3/2021 | Miller et al. |
| 2021/0117969 A1 | 4/2021 | Chilaka et al. |
| 2021/0144131 A1 | 5/2021 | Krishnamacharya |
| 2021/0158299 A1 | 5/2021 | Baggett |
| 2021/0158368 A1 | 5/2021 | Baggett |
| 2021/0203667 A1 | 7/2021 | Bondugula et al. |
| 2021/0234869 A1 | 7/2021 | Bondugula et al. |
| 2021/0240808 A1 | 8/2021 | Sadhwani et al. |
| 2021/0241120 A1 | 8/2021 | Chen et al. |

(56) References Cited

U.S. PATENT DOCUMENTS

| | | |
|---|---|---|
| 2021/0273805 A1 | 9/2021 | Jain et al. |
| 2021/0288948 A1 | 9/2021 | Joffe et al. |
| 2021/0357707 A1 | 11/2021 | Bondugula et al. |
| 2021/0400120 A1 | 12/2021 | Prieditis |
| 2022/0019733 A1 | 1/2022 | Billman et al. |
| 2022/0027891 A1 | 1/2022 | Anderson et al. |
| 2022/0044343 A1 | 2/2022 | Chapa et al. |
| 2022/0070169 A1 | 3/2022 | Cano et al. |
| 2022/0070294 A1 | 3/2022 | Cody et al. |
| 2022/0109578 A1 | 4/2022 | Kirsch |
| 2022/0138238 A1 | 5/2022 | Rege et al. |
| 2022/0156394 A1 | 5/2022 | Riley et al. |
| 2022/0173887 A1 | 6/2022 | Krishnamacharya et al. |
| 2022/0182487 A1 | 6/2022 | Sharma et al. |
| 2022/0217146 A1 | 7/2022 | Felice-Steele et al. |
| 2022/0222368 A1 | 7/2022 | Min et al. |
| 2022/0239665 A1 | 7/2022 | Bondugula et al. |
| 2022/0261461 A1 | 8/2022 | Bondugula et al. |
| 2022/0279067 A1 | 9/2022 | Sena, Jr. et al. |
| 2022/0345460 A1 | 10/2022 | Alden et al. |

FOREIGN PATENT DOCUMENTS

| | | |
|---|---|---|
| AU | 2022204452 | 7/2022 |
| CA | 2 509 842 | 12/2005 |
| CA | 2 868 933 | 10/2013 |
| CA | 3 076 931 | 10/2020 |
| CA | 3 052 415 | 7/2021 |
| CA | 2 896 503 | 8/2021 |
| CA | 2 792 070 | 10/2021 |
| CN | 104877993 | 9/2015 |
| CN | 106255985 | 12/2016 |
| CN | 112036952 | 12/2020 |
| EP | 0 419 889 | 4/1991 |
| EP | 0 458 698 | 11/1991 |
| EP | 0 542 298 | 5/1993 |
| EP | 0 559 358 | 9/1993 |
| EP | 0 977 128 | 2/2000 |
| EP | 1 028 401 | 8/2000 |
| EP | 0 772 836 B1 | 12/2001 |
| EP | 1 239 378 | 9/2002 |
| EP | 1 301 887 | 4/2003 |
| EP | 1 591 931 | 11/2005 |
| EP | 1 850 278 | 10/2007 |
| EP | 2 088 743 | 8/2009 |
| EP | 2 151 793 | 2/2010 |
| EP | 2 425 583 | 3/2012 |
| EP | 2 472 423 | 7/2012 |
| EP | 2 074 513 | 2/2016 |
| EP | 3 201 804 | 4/2020 |
| EP | 2 939 364 | 6/2020 |
| EP | 3 577 850 | 7/2021 |
| EP | 3 846 104 | 7/2021 |
| EP | 3 862 897 | 8/2021 |
| EP | 4 060 941 | 9/2022 |
| ES | 2 752 058 | 4/2020 |
| ES | 2 811 070 | 3/2021 |
| GB | 1 322 809 | 7/1973 |
| GB | 2 102 606 | 2/1983 |
| GB | 2 518 099 | 3/2015 |
| IN | 349972 | 4/2016 |
| IN | 201917040928 | 11/2019 |
| JP | 10-222559 | 8/1998 |
| JP | 10-261009 | 9/1998 |
| JP | 10-293732 | 11/1998 |
| JP | 2000-331068 | 11/2000 |
| JP | 2001-297141 | 10/2001 |
| JP | 2001-344463 | 12/2001 |
| JP | 2001-357256 | 12/2001 |
| JP | 2002-149778 | 5/2002 |
| JP | 2002-163498 | 6/2002 |
| JP | 2002-259753 | 9/2002 |
| JP | 2003-271851 | 9/2003 |
| JP | 2003-316881 | 11/2003 |
| JP | 2005-135431 | 5/2005 |
| JP | 2005-208945 | 8/2005 |
| JP | 4202314 | 12/2008 |
| JP | 2012-113696 | 6/2012 |
| KR | 10-2000-0036594 | 7/2000 |
| KR | 10-2000-0063313 | 11/2000 |
| KR | 10-2000-0063995 | 11/2000 |
| KR | 10-2001-0016349 | 3/2001 |
| KR | 10-2001-0035145 | 5/2001 |
| KR | 10-2002-0007132 | 1/2002 |
| KR | 10-2002-0039203 | 5/2002 |
| KR | 10-2004-0078798 | 9/2004 |
| KR | 10-2007-0081504 | 8/2007 |
| RU | 2 181 216 | 4/2002 |
| TW | 1256569 | 6/2006 |
| WO | WO 91/16691 | 10/1991 |
| WO | WO 95/034155 | 12/1995 |
| WO | WO 96/000945 | 1/1996 |
| WO | WO 98/041931 | 9/1998 |
| WO | WO 98/041932 | 9/1998 |
| WO | WO 98/041933 | 9/1998 |
| WO | WO 98/049643 | 11/1998 |
| WO | WO 99/017225 | 4/1999 |
| WO | WO 99/017226 | 4/1999 |
| WO | WO 99/038094 | 7/1999 |
| WO | WO 99/054803 | 10/1999 |
| WO | WO 99/060481 | 11/1999 |
| WO | WO 00/004465 | 1/2000 |
| WO | WO 00/028441 | 5/2000 |
| WO | WO 00/030045 | 5/2000 |
| WO | WO 00/051052 | 8/2000 |
| WO | WO 00/055778 | 9/2000 |
| WO | WO 00/065469 | 11/2000 |
| WO | WO 01/009752 | 2/2001 |
| WO | WO 01/009792 | 2/2001 |
| WO | WO 01/010090 | 2/2001 |
| WO | WO 01/046889 | 6/2001 |
| WO | WO 01/084281 | 11/2001 |
| WO | WO 02/011025 | 2/2002 |
| WO | WO 02/029636 | 4/2002 |
| WO | WO 03/073711 | 9/2003 |
| WO | WO 2004/031986 | 4/2004 |
| WO | WO 2004/049654 | 6/2004 |
| WO | WO 2004/084098 | 9/2004 |
| WO | WO 2004/088464 | 10/2004 |
| WO | WO 2004/114160 | 12/2004 |
| WO | WO 2005/010683 | 2/2005 |
| WO | WO 2005/033979 | 4/2005 |
| WO | WO 2005/059781 | 6/2005 |
| WO | WO 2005/098630 | 10/2005 |
| WO | WO 2006/019752 | 2/2006 |
| WO | WO 2006/050278 | 5/2006 |
| WO | WO 2006/069199 | 6/2006 |
| WO | WO 2006/099081 | 9/2006 |
| WO | WO 2007/001394 | 1/2007 |
| WO | WO 2007/050156 | 5/2007 |
| WO | WO 2007/084555 | 7/2007 |
| WO | WO 2007/103203 | 9/2007 |
| WO | WO 2008/021104 | 2/2008 |
| WO | WO 2008/022289 | 2/2008 |
| WO | WO 2008/042614 | 4/2008 |
| WO | WO 2008/054403 | 5/2008 |
| WO | WO 2008/054849 | 5/2008 |
| WO | WO 2008/127288 | 10/2008 |
| WO | WO 2009/064694 | 5/2009 |
| WO | WO 2009/064840 | 5/2009 |
| WO | WO 2009/076555 | 6/2009 |
| WO | WO 2009/102391 | 8/2009 |
| WO | WO 2009/108901 | 9/2009 |
| WO | WO 2009/117468 | 9/2009 |
| WO | WO 2009/117518 | 9/2009 |
| WO | WO 2010/001406 | 1/2010 |
| WO | WO 2010/062537 | 6/2010 |
| WO | WO 2010/077989 | 7/2010 |
| WO | WO 2010/132492 | 11/2010 |
| WO | WO 2010/150251 | 12/2010 |
| WO | WO 2011/005876 | 1/2011 |
| WO | WO 2011/014878 | 2/2011 |
| WO | WO 2011/109576 | 9/2011 |
| WO | WO 2012/054646 | 4/2012 |

(56) References Cited

FOREIGN PATENT DOCUMENTS

| | | |
|---|---|---|
| WO | WO 2012/097171 | 7/2012 |
| WO | WO 2013/009920 | 1/2013 |
| WO | WO 2013/015746 | 1/2013 |
| WO | WO 2013/126281 | 8/2013 |
| WO | WO 2013/140410 | 9/2013 |
| WO | WO 2014/008079 | 1/2014 |
| WO | WO 2014/018900 | 1/2014 |
| WO | WO 2014/066816 | 5/2014 |
| WO | WO 2014/150987 | 9/2014 |
| WO | WO 2015/038520 | 3/2015 |
| WO | WO 2015/057538 | 4/2015 |
| WO | WO 2018/129373 | 7/2018 |
| WO | WO 2018/144612 | 8/2018 |
| WO | WO 2018/191638 | 10/2018 |
| WO | WO 2018/199992 | 11/2018 |
| WO | WO 2018/236732 | 12/2018 |
| WO | WO 2019/006144 | 1/2019 |
| WO | WO 2019/089439 | 5/2019 |
| WO | WO 2019/136407 | 7/2019 |
| WO | WO 2019/152592 | 8/2019 |
| WO | WO 2019/157491 | 8/2019 |
| WO | WO 2019/183483 | 9/2019 |
| WO | WO 2019/209857 | 10/2019 |
| WO | WO 2019/245998 | 12/2019 |
| WO | WO 2020/051154 | 3/2020 |
| WO | WO 2020/072239 | 4/2020 |
| WO | WO 2020/198236 | 10/2020 |
| WO | WO 2020/206305 | 10/2020 |
| WO | WO 2020/232137 | 11/2020 |
| WO | WO 2021/011308 | 1/2021 |
| WO | WO 2021/067446 | 4/2021 |
| WO | WO 2021/081516 | 4/2021 |
| WO | WO 2021/097090 | 5/2021 |
| WO | WO 2021/138263 | 7/2021 |
| WO | WO 2021/155053 | 8/2021 |
| WO | WO 2022/109613 | 5/2022 |

OTHER PUBLICATIONS

U.S. Appl. No. 12/705,511, filed Feb. 12, 2010, Bargoli et al.
U.S. Appl. No. 60/146,074, filed Jul. 28, 1999, Tomkow.
U.S. Appl. No. 60/172,479, filed Dec. 17, 1999, Tomkow.
Actuate, "Delivering Enterprise Information for Corporate Portals", White Paper, 2004, pp. 1-7.
"Aggregate and Analyze Social Media Content: Gain Faster and Broader Insight to Market Sentiment," SAP Partner, Mantis Technology Group, Apr. 2011, pp. 4.
Aharony et al., "Social Area Networks: Data Networking of the People, by the People, for the People," 2009 International Conference on Computational Science and Engineering, May 2009, pp. 1148-1155.
Akl, Selim G., "Digital Signatures: A Tutorial Survey," Computer, Feb. 1983, pp. 15-24.
Aktas et al., "Personalizing PageRank Based on Domain Profiles", WEBKDD workshop: Webmining and Web Usage Analysis, Aug. 22, 2004, pp. 83-90.
Aktas et al., "Using Hyperlink Features to Personalize Web Search", WEBKDD workshop: Webmining and Web Usage Analysis, Aug. 2004.
"Arizona Company Has Found Key in Stopping ID Theft," PR Newswire, New York, Aug. 10, 2005 http://proquest.umi.com/pqdweb?did=880104711&sid=1&Fmt=3&clientId=19649&RQT=309&Vname=PQD.
ABC News Now:Money Matters, as broadcasted Nov. 15, 2005 with guest Todd Davis (CEO of Lifelock), pp. 6.
Anonymous, "Credit-Report Disputes Await Electronic Resolution," Credit Card News, Chicago, Jan. 15, 1993, vol. 5, No. 19, p. 5.
Anonymous, "MBNA Offers Resolution of Credit Card Disputes," Hempstead, Feb. 2002, vol. 68, No. 2, p. 47.
Anonymous, "Feedback", Credit Management, ABI/INFORM Global, Sep. 2006, pp. 6.
Awoonor-Williams, Princess Josephine, Ph.D. "Gender and Credit: An Analysis of Women's Experience in the Credit Market", ProQuest Dissertations and Theses, May 2004, pp. 148.
Babcock, Gwen, "Aggregation Without Aggravation: Determining Spatial Contiguity and Joining Geographic Areas Using Hashing", SAS Global Forum 2010, Reporting and Information Visualization, Paper 223-2010, pp. 17.
Bacon, Chris, "OAuth id_token missing information on refresh #1141", https://github.com/googleapis/google-api-dotnet-client/issues/1141, Jan. 1, 2018, pp. 9.
"Beware of 'Who Viewed My Profile' Apps on Facebook" Tech for Luddites, Mar. 15, 2010 printed Sep. 27, 2013 http://www.techforluddites.com/2010/03/beware-of-who-viewed-my-profile-apps-on-facebook.html.
Bielski, Lauren, "Will you Spend to Thwart ID Theft?" ABA Banking Journal, Apr. 2005, pp. 54, 56-57, 60.
Bitran et al., "Mailing Decisions in Catalog Sales Industry", Management Science (JSTOR), vol. 42, No. 9, pp. 1364-1381, Sep. 1996.
BlueCava, "What We Do", http://www.bluecava.com/what-we-do/, printed Nov. 5, 2012 in 3 pages.
Brick, et al. "Unit and Item Response, Weighting, and Imputation Procedures in the 1993 National Household Education Survey (NHES:93)" U.S. Department of Education. National Center for Education Statistics, Working Paper No. 97-05, Washington, D.C., pp. 30, Feb. 1997.
Burr Ph.D., et al., "Utility Payments as Alternative Credit Data: A Reality Check", Asset Builders of America, Inc., Oct. 5, 2006, pp. 1-18, Washington, D.C.
Buxfer, http://www.buxfer.com/ printed Feb. 5, 2014 in 1 page.
Cáceres, et al., "Measurement and Analysis of IP Network Usage and Behavior", IEEE Communications Magazine, pp. 144-151, May 2000.
Census Geography, Excerpted from the Geographic Reference Manual, Nov. 1994, pp. 5.
Check, http://check.me/ printed Feb. 5, 2014 in 3 pages.
Cheng, Fred, "Security Attack Safe Mobile and Cloud-based One-time Password Tokens Using Rubbing Encryption Algorithm", MONET, 2011, vol. 16, pp. 304-336.
Chiba et al., "Mobility Management Schemes for Heterogeneity Support in Next Generation Wireless Networks", 3rd EuroNGI Conference on, 2007, pp. 143-150.
Chores & Allowances, "Do Kids Have Credit Reports?" Oct. 15, 2007, http://choresandallowances.blogspot.com/2007/10/do-kids-have-credit-reports.html, pp. 5.
Comlounge.net, "plonesocial.auth.rpx" http://web.archive.org/web/20101026041841/http://comlounge.net/rpxas captured Oct. 26, 2010 in 9 pages.
"Consumer Reports Finds American-Made Vehicles Close Reliability Gap with European-Made Vehicle—As Japanese Continue to Set New Benchmarks for the Industry", Consumer Reports: Consumers Union, Yonkers, NY, Apr. 2003, pp. 2.
Corepoint Health, "The Continuity of Care Document—Changing the Landscape of Healthcare Information Exchange," Jan. 2009, pp. 9.
CreditKarma, http://www.creditkarma.com printed Feb. 8, 2013 in 2 pages.
CreditSesame, http://www.creditsesame.com/how-it-works/our-technology/ printed Feb. 5, 2013 in 2 pages.
Cohen et al., "Optimizer: IBM's Multi Echelon Inventory System for Managing Service Logistics", Interfaces, vol. 20, No. 1, Jan.-Feb. 1990, pp. 65-82.
Collins, Michael J., "Exploring the Design of Financial Counseling for Mortgage Borrowers in Default," Journal of Family and Economic Issues, Springer Science+Business Media, Mar. 13, 2007, pp. 207-226.
Consumer Financial Protection Bureau (CFPB): Analysis of Difference between Consumer- and Creditor-Purchased Credit Scores, Sep. 2012, pp. 1-42.

(56) References Cited

OTHER PUBLICATIONS

"Consumers Gain Immediate and Full Access to Credit Score Used by Majority of U.S. Lenders", PR Newswire, ProQuest Copy, Mar. 19, 2001, p. 1.
"CreditCheck Monitoring Services," Dec. 11, 2000, pp. 1, lines 21-23.
"Credit Improvement", CreditRepair.com, Mar. 10, 2010, http://web.archive.org/web/20100310134914/http://www.creditrepair.com/credit/, as archived Mar. 10, 2010 in 2 pages.
Credit Plus, Inc., "Score Wizard", http://web.archive.org/web/20030806080310/www.creditplus.com/scorewizard.asp, as archived Aug. 6, 2003 in 1 page.
Cullen, Terri; "The Wall Street Journal Complete Identity Theft Guidebook:How to Protect Yourself from the Most Pervasive Crime in America"; Chapter 3, pp. 59-79; Jul. 10, 2007.
"D&B Corporate Family Linkage", D&B Internet Access for U.S. Contract Customers, https://www.dnb.com/ecomp/help/linkage.htm as printed Dec. 17, 2009, pp. 1.
Dankar et al., "Efficient Private Information Retrieval for Geographical Aggregation", Procedia Computer Science, 2014, vol. 37, pp. 497-502.
"Data Loss Prevention (DLP) Software", http://www.symantec.com/data-loss-prevention/ printed Apr. 8, 2013 in 8 pages.
"Data Protection", http://compliantprocessing.com/data-protection/ printed Apr. 8, 2013 in 4 pages.
Davies, Donald W., "Applying the RSA Digital Signature to Electronic Mail," Computer, Feb. 1983, pp. 55-62.
Day, Jo and Kevin; "ID-ology: A Planner's Guide to Identity Theft"; Journal of Financial Planning:Tech Talk; pp. 36-38; Sep. 2004.
"Debt Settlement: Watch Video on how to Pay Your Debt Faster", http://www.debtconsolidationcare.com/debt-settlement.html printed Jan. 9, 2013 in 6 pages.
Demby, Elayne, "Special Report: Letting Consumers Know the Score—and More", Collections and Credit Risk, New York, Feb. 2003, vol. 8, Issue 2, p. 53, pp. 3.
"Disputes in Cyberspace 2001: Update of online dispute resolution for consumers in cross-border disputes", Consumers International, Nov. 2001, pp. 45, http://web.archive.org/web/20160414183303/http://www.consumersinternational.org/media/304196/disputes%20in%20cyberspace%202001.%20update%20of%20online%20dispute%20resolution%20for%20consumers%20in%20cross-border%20disputes..pdf.
Elangovan, A.R., "Managerial Third-Party Dispute Intervention: A Prescriptive Model of Strategy Selection", Academy of Management, Oct. 1, 1995, vol. 20, No. 4, pp. 800-830.
Elliehausen et al., The Impact of Credit Counseling on Subsequent Borrower Behavior, The Journal of Consumer Affairs, Summer 2007, vol. 41, No. 1, pp. 1-28.
Elmasri et al., "Fundamentals of Database Systems, Third Edition (Excerpts)", Jun. 2000, pp. 253, 261, 268-70, 278-80, 585, 595.
Equifax, "Business Status Alerts: User Guide", Jul. 2009, pp. 1-21.
Equifax Consumer Credit Report http://www.equifax.com/home/, as retrieved on Sep. 17, 2008.
Equifax, "InstaTouch ID: Separate Fact from Friction." http://equifax.uberflip.com/i/791148-mobile-consumer-identity-service-product-sheet/1, 2016, pp. 2.
Equifax; "Equifax Credit Watch"; https://www.econsumer.equifax.co.uk/consumer/uk/sitepage.ehtml, dated Jun. 27, 2007 on www.archive.org.
"Equifax: Debt Wise™ Credit Monitoring Service," Product Review, http://www.mdmproofing.com/iym/reviews/equifax/debt-wise/, Jan. 2010, pp. 11.
Equifax; "Places", http://web.archive.org/web/20111111113930/http://www.equifax.com/places as archived Nov. 11, 2011 in 1 page.
Equifax; "Places", http://www.equifax.com/places/as printed Nov. 16, 2015 in 1 page.
Equifax; "Welcome to Equifax Mobile", http://www.equifax.com/mobile/ as printed Mar. 18, 2011 in 2 pages.
Ettorre, "Paul Kahn on Exceptional Marketing," Management Review, vol. 83, No. 11, Nov. 1994, pp. 48-51.

Experian Consumer Credit Report http://www.experian.com/, as retrieved on Sep. 17, 2008.
"Experian Helps Verify the Identity of Patients and Provide Secure Enrollment to Healthcare Portals by Integrating with Major Electronic Medical Records Platform," http://press.experian.com/United-States/Press-Release/experian-helps-verify-the-identity-of-patients-and-provide-secure-enrollment-to-healthcare.aspx?&p=1, Dec. 19, 2013, pp. 2.
Experian: Improve Outcomes Through Applied Customer Insight, Brochure, Nov. 2009, pp. 20.
Experian: Mosaic Geodemographic Lifestyle Segmentation on ConsumerView [Data Card], as printed from http://datacards.experian.com/market?page=research/datacard_print&prin, Apr. 6, 2012, pp. 4.
Experian: Mosaic Public Sector 2009 Launch, Jul. 2009, pp. 164.
Experian: Mosaic United Kingdom, Brochure, Jun. 2009, pp. 24.
Experian: Mosaic UK—Optimise the Value of Your Customers and Locations, Now and in the Future, Brochure, Sep. 2010, pp. 24.
Experian: Mosaic UK—Unique Consumer Classification Based on In-Depth Demographic Data, as printed from http://www.experian.co.uk/business-strategies/mosaic-uk.html, Jul. 30, 2012, pp. 2.
Experian: Mosaic USA, Brochure, May 2009, pp. 14.
Experian: Mosaic USA—Consumer Lifestyle Segmentation [Data Card], Dec. 2009, pp. 2.
Experian: Public Sector, as printed form http://publicsector.experian.co.uk/Products/Mosaicpublicsector.aspx, Jul. 2009, pp. 2.
Experian, "Experian Rental Payment Data," http://www.experian.com/rentbureau/rental-data.html printed Nov. 22, 2013 in 2 pages.
Facebook, "Facebook helps you connect and share with the people in your life," www.facebook.com printed Nov. 16, 2010 in 1 page.
FamilySecure.com, "Frequently Asked Questions", http://www.familysecure.com/FAQ.aspx as archived Jul. 15, 2007 in 3 pages.
FamilySecure.com; "Identity Theft Protection for the Whole Family | FamilySecure.com" http://www.familysecure.com/, as retrieved on Nov. 5, 2009.
Fenner, Peter, "Mobile Address Management and Billing for Personal Communications", 1st International Conference on Universal Personal Communications, 1992, ICUPC '92 Proceedings, pp. 253-257.
"Fictitious Business Name Records", Westlaw Database Directory, http://directory.westlaw.com/scope/default.asp?db=FBN-ALL&RS-W...&VR=2.0 as printed Dec. 17, 2009, pp. 5.
Fisher, Joseph, "Access to Fair Credit Reports: Current Practices and Proposed Legislation," American Business Law Journal, Fall 1981, vol. 19, No. 3, p. 319.
Fisher, Greg, "Credit Score Distribution and Practical Range Statistics", Feb. 23, 2010, The Credit Scoring Site, pp. 2.
Fitzpatrick, Alex, "Facebook Monitors Your Chats for Criminal Activity [Report]," Mashable, Jul. 12, 2012 printed Sep. 27, 2013 http://mashable.com/2012/07/12/facebook-scanning-chats/.
Franks et al., "HTTP Authentication: Basic and Digest Access Authentication", Network Working Group, Standards Track, Jun. 1999, pp. 34.
"Fraud Alert | Learn How". Fight Identity Theft. http://www.fightidentitytheft.com/flag.html, accessed on Nov. 5, 2009.
"Fund Manager," Portfolio Management Software website, indexed into Google on Jan. 7, 2005, Retrieved Oct. 24, 2014 http://www.fundmanagersoftware.com/, http://www.fundmanagersoftware.com/help/gph_tp_pieasset.html, http://www.fundmanagersoftware.com/demo2.html.
Garcia-Molina et al., "Database Systems: The Complete Book", Prentice Hall, Inc., Ch. 15, Oct. 1, 2001, pp. 713-715.
"Geographic Aggregation Tool SAS Beta Version 4.1", Environmental Health Surveillance Section, New York State Dept, in Health, Troy, NY, Mar. 24, 2015, pp. 10.
Gibbs, Adrienne; "Protecting Your Children from Identity Theft," Nov. 25, 2008, http://www.creditcards.com/credit-card-news/identity-ID-theft-and-kids-children-1282.php, pp. 4.
Gionis et al., "Similarity Search in High Dimensions via Hashing", Sep. 7, 1999, pp. 518-529.
"GLBA Compliance and FFIEC Compliance" http://www.trustwave.com/financial-services.php printed Apr. 8, 2013 in 1 page.

(56) References Cited

OTHER PUBLICATIONS

Glenn, Brandon, "Multi-provider patient portals get big boost with ONC ruling", Feb. 25, 2013, http://medicaleconomics.modernmedicine.com/medical-economics/news/user-defined-tags/meaningful-use/multi-provider-patient-portals-get-big-boost in 2 pages.
Gordon et al., "Identity Fraud: A Critical National and Global Threat," LexisNexis, Oct. 28, 2003, pp. 1-48.
Gordon et al., "Using Identity Authentication and Eligibility Assessment to Mitigate the Risk of Improper Payments", LexisNexis, Jan. 28, 2008, pp. 18. https://risk.lexisnexis.com/-/media/files/government/white-paper/identity_authentication-pdf.pdf.
"Guide to Benefits, MasterCard® Cardholder Smart Shopper Benefits", May 2005, pp. 10.
Haffar, Imad, "'SPAM': A Computer Model for Management of Spare-Parts Inventories in Agricultural Machinery Dealerships", Computers and Electronics in Agriculture, vol. 12, Issue 4, Jun. 1995, pp. 323-332.
Hampton et al., "Mapping Health Data: Improved Privacy Protection With Donut Method Geomasking", American Journal of Epidemiology, Septembers, 2010, vol. 172, No. 9, pp. 8.
Handfield et al., "Managing Component Life Cycles in Dynamic Technological Environments", International Journal of Purchasing and Materials Management, Tempe, Spring 1994, vol. 30, No. 2, pp. 20-28.
Harrington et al., "iOS 4 in Action", Chapter 17, Local and Push Notification Services, Manning Publications Co., Jun. 2011, pp. 347-353.
Healow.com, Various screenshots from page titled "Health and Online Wellness," https://healow.com/apps/jsp/webview/index.jsp printed Aug. 19, 2013 in 4 pages.
Healthspek.com, "How Good Are We?" http://healthspek.com/how-good-are-we/ printed Jan. 21, 2014 in 2 pages.
"Healthspek Users Can Now Import Their Doctors' Records into Their Personal Health Record," PRWeb, Nashville, TN, Jan. 14, 2014, pp. 1 http://www.prweb.com/releases/2014/01/prweb11485346.htm.
Herron, Janna, "Social Media-Based Credit Score?", http://www.bankrate.com/financing/credit-cards/social-media-based-credit-score/, posted Friday, Jan. 13, 2012, printed Nov. 22, 2013 in 2 pages.
Herzberg, Amir, "Payments and Banking with Mobile Personal Devices," Communications of the ACM, May 2003, vol. 46, No. 5, pp. 53-58.
Hoofnagle, Chris Jay, "Identity Theft: Making the Known Unknowns Known," Harvard Journal of Law & Technology, Fall 2007, vol. 21, No. 1, pp. 98-122.
Hunt, Robert M.; Whither Consumer Credit Counseling? Business Review, Dec. 31, 2005, pp. 9-20.
ID Analytics, "ID Analytics® Consumer Notification Service" printed Apr. 16, 2013 in 2 pages.
ID Theft Assist, "Do You Know Where Your Child's Credit Is?", Nov. 26, 2007, http://www.idtheftassist.com/pages/story14, pp. 3.
"ID Thieves These Days Want Your Number Not Your Name", The Columbus Dispatch, Columbus, Ohio, http://www.dispatch.com/content/stories/business/2014/08/03/id-thieves-these-days-want-your-number-not-your-name.html, Aug. 3, 2014 in 2 pages.
Identity Theft Resource Center; Fact Sheet 120 A—To Order a Credit Report for a Child; Fact Sheets, Victim Resources; Apr. 30, 2007.
"Identity Thieves Beware: Lifelock Introduces Nation's First Guaranteed Proactive Solution to Identity Theft Protection," PR Newswire, New York, Jun. 13, 2005 http://proquest.umi.com/pqdweb?did=852869731&sid=1&Fmt=3&clientId=19649&RQT=309&Vname=PQD.
Ideon, Credit-Card Registry that Bellyflopped this Year, Is Drawing some Bottom-Fishers, The Wall Street Journal, Aug. 21, 1995, pp. C2.
igihealth.com, "Orbit® PHR: Personal Health Record (PHR)," http://www.igihealth.com/consumers/orbit_phr.html, printed Jan. 21, 2014 in 2 pages.

Inderfurth et al., "Decision Support for Spare Parts Acquisition in Post Product Life Cycle", Central European Journal of Operations Research, 2008, vol. 16, pp. 17-42.
Information Brokers of America, "Information Brokers of America Child Identity Theft Protection" http://web.archive.org/web/20080706135451/http://iboainfo.com/child-order.html as archived Jul. 6, 2008 in 1 page.
Information Brokers of America, "Safeguard Your Child's Credit", http://web.archive.org/web/20071215210406/http://www.iboainfo.com/child-id-protect.html as archived Dec. 15, 2007 in 1 page.
InsightsOne.com, "Healthcare," http://insightsone.com/healthcare-predictive-analytics/ printed Mar. 6, 2014 in 5 pages.
Intelius, "People Search—Updated Daily, Accurate and Fast!" http://www.intelius.com/people-search.html?=&gclid=CJqZIZP7paUCFYK5KgodbCUJJQ printed Nov. 16, 2010 in 1 page.
"Intelligent Miner Applications Guide", IBM Corp., Apr. 2, 1999, Chapters 4-7, pp. 33-132.
Iovation, Device Identification & Device Fingerprinting, http://www.iovation.com/risk-management/device-identification printed Nov. 5, 2012 in 6 pages.
Irby, LaToya, "How Will a Late Payment Hurt My Credit Score?" http://web.archive.org/web/20101024113603/http://credit.about.com/od/creditscorefaq/f/how-late-payment-affects-credit-score.htm, Oct. 24, 2010, pp. 1.
"Japan's JAAI System Appraises Used Cars Over Internet", Asia Pulse, Mar. 3, 2000, p. 1.
Jaro, Matthew A., "Probabilistic Linkage of Large Public Health Data Files", Statistics in Medicine, 1995, vol. 14, pp. 491-498.
Jones et al., "JSON Web Signature (JWS)", Internet Engineering Task Force (IETF), ISSN: 2070-1721, Standards Track, May 2015, pp. 59.
"Judging Credit: Consumers Need Better Finance Tools", News Journal, Daytona Beach, FL, Dec. 28, 2002.
Käki, Anssi, "Forecasting in End-Of-Life Spare Parts Procurement", Master's Thesis, Helsinki University of Technology, System Analysis Laboratory, Jul. 27, 2007, pp. 84.
Kaushik, Nishant, "The Epic Hacking of Mat Honan and Our Identity Challenge," Aug. 7, 2012, http://blog.talkingidentity.com/2012/08/the-epic-hacking-of-mat-honan-and-our-identity-challenge.html.
Khan, Mickey Alam, "Equifax Recognizes Changing Customer Behavior with Four-Pronged Mobile Strategy", Mobile Marketer, http://web.archive.org/web/20151117005818/http://www.mobilemarketer.com/cms/news/strategy/9733.html, Apr. 19, 2011 in 10 pages.
Khan, Muhammad Khurram, PhD., "An Efficient and Secure Remote Mutual Authentication Scheme with Smart Cards" IEEE International Symposium on Biometrics & Security Technologies (ISBAST), Apr. 23-24, 2008, pp. 1-6.
Khare et al., "Nutch: A Flexible and Scalable Open-Source Web Search Engine", CommerceNet Labs Technical Reprt 04-04, Nov. 2004, pp. 15.
Kim et al., "Optimal Pricing, EOL (End of Life) Warranty, and Spare Parts Manufacturing Strategy Amid Product Transition", European Journal of Operation Research, 2008, vol. 188, pp. 723-745.
Klein, et al., "A Constant-Utility Index of the Cost of Living", The Review of Economic Studies, Sep. 1, 1947, vol. 15, No. 2, pp. 84-87.
Klein, et al., "An Econometric Model of the United States: 1929-1952", North-Holland Publishing Company, Amsterdam, Jun. 1, 1955, pp. 4-41.
Klein, Lawrence R., "The Keynesian Revolution", New York, The MacMillan Company, Jan. 1, 1947, pp. 56-189.
Krupp, James A.G., "Forecasting for the Automotive Aftermarket", The Journal of Business Forecasting Methods & Systems, Winter 1993-1994, vol. 12, No. 4, ABI/Inform Global, pp. 8-12.
Kwan et al., "Protection of Geoprivacy and Accuracy of Spatial Information: How Effective Are Geographical Masks?" Carographica, Summer 2004, vol. 39, No. 2, pp. 15-27.

(56) References Cited

OTHER PUBLICATIONS

Lan, Joe, "The Top Portfolio Management Software," http://www.aaii.com/computerizedinvesting/article/the-top-portfolio-management-software, Includes Discussion thread, Fourth Quarter 2011, pp. 17.
Lang et al., "A Collaborative Web-Based Help-System", Proceedings of the 2nd international conference on web intelligence, mining and semantics, Jun. 13-15, 2012, pp. 5.
Lang et al., "An Avatar-Based Help System for Web-Portals", International Conference on Human-Computer Interaction, Springer, Berlin, Heidelberg, 2011, pp. 10.
Lanubile, et al., "Evaluating Empirical Models for the Detection of High-Risk Components: Some Lessons Learned", 20th Annual Software Engineering Workshop, Nov. 29-30, 1995, Greenbelt, Maryland, pp. 1-6.
Lapide, Larry, "New Developments in Business Forecasting", The Journal of Business Forecasting, Spring 2002, pp. 12-14.
Lauwers et al., "Five Hundred Years of Bookkeeping: A Portrait of Luca Pacioli", Tijdschrift voor Economie en Management, 1994, vol. 39. No. 3, pp. 289-304.
Lee, W.A.; "Experian, on Deal Hunt, Nets Identity Theft Insurer", American Banker: The Financial Services Daily, Jun. 4, 2003, New York, NY, 1 page.
Lefebvre et al., "A Robust Soft Hash Algorithm for Digital Image Signature", International Conference on Image Processing 2:11 (ICIP), vol. 3, Oct. 2003, pp. 495-498.
LendingTree.com, "Lender Ratings & Reviews," http://web.archive.org/web/20091015043716/http://www.lendingtree.com/lender-reviews/, Oct. 15, 2009, in 21 pages.
Leskovec, Jure, "Social Media Analytics: Tracking, Modeling and Predicting the Flow of Information through Networks", WWW2011-Tutorial, Mar. 28-Apr. 1, 2011, Hyderabad, India, pp. 277-278.
Letter to Donald A. Robert from Carolyn B. Maloney, dated Oct. 31, 2007, pp. 2.
Letter to Donald A. Robert from Senator Charles E. Schumer, dated Oct. 11, 2007, pp. 2.
Letter to Harry C. Gambill from Carolyn B. Maloney, dated Oct. 31, 2007, pp. 2.
Letter to Harry C. Gambill from Senator Charles E. Schumer, dated Oct. 11, 2007, pp. 2.
Letter to Richard F. Smith from Carolyn B. Maloney, dated Oct. 31, 2007, pp. 2.
Letter to Richard F. Smith from Senator Charles E. Schumer, dated Oct. 11, 2007, pp. 2.
Li et al., "Automatic Verbal Information Verification for User Authentication", IEEE Transactions on Speech and Audio Processing, vol. 8, No. 5, Sep. 2000, pp. 585-596.
LifeLock, http://web.archive.org/web/20110724011010/http://www.lifelock.com/? as archived Jul. 24, 2011 in 1 page.
LifeLock, "How LifeLock Works," http://www.lifelock.com/lifelock-for-people printed Mar. 14, 2008 in 1 page.
LifeLock, "LifeLock Launches First ID Theft Prevention Program for the Protection of Children," Press Release, Oct. 14, 2005, http://www.lifelock.com/about-us/press-room/2005-press-releases/lifelock-protection-for-children.
LifeLock; "How Can LifeLock Protect My Kids and Family?" http://www.lifelock.com/lifelock-for-people/how-we-do-it/how-can-lifelock-protect-my-kids-and-family printed Mar. 14, 2008 in 1 page.
LifeLock, "Personal Identity Theft Protection & Identity Theft Products," http://www.lifelock.com/lifelock-for-people, accessed Nov. 5, 2007.
LifeLock, Various Pages, www.lifelock.com/, Jan. 9, 2007, pp. 49.
Littwin, Angela, "Beyond Usury: A Study of Credit-Card Use and Preference Among Low-Income Consumers", Texas Law Review, vol. 86, No. 3, pp. 451-506; Feb. 2008.
Lobo, Jude, "MySAP.com Enterprise Portal Cookbook," SAP Technical Delivery, Feb. 2002, vol. 1, pp. 1-13.
Lodderstedt et al., "OAuth 2.0 token Revocation", Internet Engineering Task Force (IETF), Standards Track, Aug. 2013, pp. 11.
Loshin, Intelligent Enterprise: Better Insight for Business Decisions, "Value-Added Data: Merge Ahead", Feb. 9, 2000, vol. 3, No. 3, 5 pages.
Lovelace, Robin, "IPFinR: An Implementation of Spatial Microsimulation in R", RL's Powerstar, Jun. 12, 2013, pp. 9, https://robinlovelace.wordpress.com/2013/06/12/ipfinr-an-implementation-of-spatial-microsimulation-in-r/.
Lund, Graham, "Credit Bureau Data: Maximizing the Benefits," Credit Management, May 2004, ProQuest Central, pp. 44-45.
Maciejewski et al., "Understanding Syndromic Hotspots—A Visual Analytics Approach", Conference Paper, IEEE Symposium on Visual Analytics Science and Technology, Oct. 21-23, 2017, pp. 35-42.
Magid, Lawrence, J., Business Tools: When Selecting an ASP Ensure Data Mobility, Los Angeles Times, Los Angeles, CA, Feb. 26, 2001, vol. C, Issue 4, pp. 3.
"Managing Debt?" Federal Trade Commission: Consumer Information, http://www.consumer.ftc.gov/articles/0158-managing-debt, printed Mar. 22, 2013 in 4 pages.
Manilla, http://www.manilla.com/how-it-works/ printed Feb. 5, 2014 in 1 page.
Mannan et al., "Mercury: Recovering Forgotten Passwords Using Personal Devices*", Dec. 17, 2011, Pre-Proceedings of Financial Cryptography and Data Security 2011, pp. 1-16.
McNamara, Paul, "Start-up's pitch: The Envelope, please," Network World, Apr. 28, 1997, vol. 14, No. 17, p. 33.
Medick et al., "German Agency to Mine Facebook to Assess Creditworthiness", Jun. 7, 2012, http://www.spiegel.de/international/germany/german-credit-agency-plans-to-analyze-individual-facebook-pages-a-837539.html printed Nov. 22, 2013 in 2 pages.
MERit Credit Engine™, Diagram, https://web.archive.org/web/20020204202530/http://creditengine.net/diagram.htm, copyright 1997, archived Feb. 4, 2002, pp. 1.
Meyers et al., "Using Your Social Networking Accounts to Log Into NPR.org," NPR.org, Jun. 24, 2010, http://web.archive.org/web/20100627034054/http://www.npr.org/blogs/inside/2010/06/24/128079309/using-your-social-networking-accounts-to-log-into-npr-org in 3 pages.
Micarelli et al., "Personalized Search on the World Wide Web," The Adaptive Web, LNCS 4321,2007, pp. 195-230.
MicroBilt, "PRBC Credit Reporting Agency—Payment Reporting Builds Credit," retrieved from http://www.microbilt.com/nontraditional-credit-report.aspx and corresponding "Sample Report," retrieved from http://www.microbilt.com/pdfs/PRBC%20Sample%20Report%20(complete).pdf printed Nov. 21, 2013 in 8 pages.
Microfinance Africa, "Philippines: Microfinance Players to get Their Own Credit Info Bureau," Apr. 5, 2011, http://microfinanceafrica.net/microfinance-around-the-world/philippines-microfinance-players-to-get-their-own-credit-info-bureau/ printed Nov. 22, 2013 in 2 pages.
Microsoft, "Expand the Reach of Your Business," Microsoft Business Solutions, 2004, in 16 pages.
Miller, Joe, "NADA Used-Car Prices Go Online", Automotive News, Jun. 14, 1999, p. 36.
Mint.com, http://www.mint.com/ printed Sep. 18, 2008 in 2 pages.
Mint.com, http://www.mint.com/how-it-works/ printed Feb. 5, 2013 in 2 pages.
Moore, John R., Jr. "Forecasting and Scheduling for Past-Model Replacement Parts", Management Science, Application Series, vol. 18, No. 4, Part 1, Dec. 1971, pp. B-200-B-213.
"Mosaic" (geodemography), available from http://en.wikipedia.org/wiki/Mosaic_(geodemography), as last modified Jul. 13, 2012. pp. 4.
MS Money Software by Microsoft http://www.microsoft.com/Money/default.mspx as retrieved on Sep. 17, 2008.
Mvelopes, http://www.mvelopes.com/ printed Feb. 5, 2014 in 2 pages.
My Call Credit http://www.mycallcredit.com/products.asp?product=ALR dated Dec. 10, 2005 on www.archive.org.
My Call Credit http://www.mycallcredit.com/rewrite.asp?display=faq dated Dec. 10, 2005 on www.archive.org.
My ID Alerts, "Why ID Alerts" http://www.myidalerts.com/why-id-alerts.jsps printed Apr. 3, 2012 in 2 pages.

(56) References Cited

OTHER PUBLICATIONS

My ID Alerts, "How it Works" http://www.myidalerts.com/how-it-works.jsps printed Apr. 3, 2012 in 3 pages.
MyRatePlan.com, "Cell Phone Buying Guide", http://web.archive.org/web/20061116103256/http://myrateplan.com/cell_phone_buying_guide/family_plans/, as archived Nov. 16, 2006 in 2 pages.
MyReceipts, http://www.myreceipts.com/, printed Oct. 16, 2012 in 1 page.
MyReceipts—How it Works, http://www.myreceipts.com/howItWorks.do, printed Oct. 16, 2012 in 1 page.
"Name Availability Records", Westlaw Database Directory, http://directory.westlaw.com/scope/default.asp?db=NA-ALL&RS=W...&VR=2.0 as printed Dec. 17, 2009, pp. 5.
National Alert Registry Launches RegisteredOffendersList.org to Provide Information on Registered Sex Offenders, May 16, 2005, pp. 2, http://www.prweb.com/printer/240437.htm accessed on Oct. 18, 2011.
National Alert Registry Offers Free Child Safety "Safe From Harm DVD and Child Identification Kit", Oct. 24, 2006. pp. 2, http://www.prleap.com/pr/53170 accessed on Oct. 18, 2011.
National Alert Registry website titled, "Does a sexual offender live in your neighborhood", Oct. 22, 2006, pp. 2, http://web.archive.org/wb/20061022204835/http://www.nationallertregistry.com/ accessed on Oct. 13, 2011.
Nelson et al., "Efficient, Automatic Web Resource Harvesting", Conference: Eighth ACM International Workshop on Web Information and Data Management (WIDM 2006), Arlington, Virginia, USA, Nov. 10, 2006, pp. 8.
"New FICO score extends lenders' reach to credit-underserved millions", Viewpoints: News, Ideas and Solutions from Fair Isaac, Sep./Oct. 2004 as downloaded from http://www.fairisaac.com/NR/exeres/F178D009-B47A-444F-BD11-8B4D7D8B3532,frame . . . in 6 pages.
"New for Investors: Asset Allocation, Seasoned Returns and More," Prosper, http://blog.prosper.com/2011/10/27/new-for-investors-asset-allocation-seasoned-returns-and-more/, Oct. 27, 2011, pp. 4.
Next Card: About Us, http://web.cba.neu.edu/~awatson/NextCardCase/NextCardAboutUs.htm printed Oct. 23, 2009 in 10 pages.
Ogg, Erica, "Apple Cracks Down on UDID Use", http://gigaom.com/apple/apple-cracks-down-on-udid-use/ printed Nov. 5, 2012 in 5 Pages.
Oracle: Recommendations for Leveraging the Critical Patch Update and Maintaining a Proper Security Posture, Nov. 2010, An Oracle White Paper, pp. 1-30.
Organizing Maniac's Blog—Online Receipts Provided by MyQuickReceipts.com, http://organizingmaniacs.wordpress.eom/2011/01/12/online-receipts-pro vided-by-myquickreceipts.com/ dated Jan. 12, 2011 printed Oct. 16, 2012 in 3 pages.
Packer, A. H., "Simulation and Adaptive Forecasting an Applied to Inventory Control", Operations Research, Jul. 1965, vol. 15, No. 4, pp. 660-679.
Pagano, et al., "Information Sharing in Credit Markets," Dec. 1993, The Journal of Finance, vol. 48, No. 5, pp. 1693-1718.
"Parse", Definition from PC Magazine Encyclopedia, http://www/pcmag.com/encyclopedia_term_0,2542,t=parse&i=48862,00.asp as downloaded Mar. 5, 2012.
Partnoy, Frank, Rethinking Regulation of Credit Rating Agencies: An Institutional Investor Perspective, Council of Institutional Investors, Apr. 2009, pp. 21.
Paustian, Chuck, "Every Cardholder a King Customers get the Full Treatment at Issuers' Web Sites," Card Marketing, New York, Mar. 2001, vol. 5, No. 3, pp. 4.
Peltier, Jon, "Conditional Formatting of Excel Charts", Peltier Tech Blog, as posted Feb. 13, 2012, http://peltiertech.com/conditional-formatting-of-excel-charts/, pp. 1-5.
People Finders, http://www.peoplefinders.com/?CMP=Google&utm_source=google&utm_medium=cpc printed Nov. 16, 2010 in 1 page.
People Lookup, "Your Source for Locating Anyone!" www.peoplelookup.com/people-search.html printed Nov. 16, 2010 in 1 page.
People Search, "The Leading Premium People Search Site on the Web," http://www.peoplesearch.com printed Nov. 16, 2010 in 2 pages.
PersonalCapital.com, http://www.personalcapital.com/how-it-works printed Feb. 5, 2014 in 5 pages.
Peters, Peter-Paul, "A Spare Parts Configurator for the European Service Business" (Graduation Report), Honeywell, Industrial Service Logistic Center, Amsterdam, The Netherlands, Mar. 2000, pp. 80.
Pinola, Melanie, "How Can I Protect Against Social Engineering Hacks?" Aug. 9, 2012, http://lifehacker.com/5933296/how-can-i-protect-against-hackers-who-use-sneaky-social-engineering-techniques-to-get-into-my-accounts, pp. 6.
Planet Receipt—Home, http://www.planetreceipt.com/home printed Oct. 16, 2012 in 1 page.
Planet Receipt—Solutions & Features, http://www.planetreceipt.com/solutions-features printed Oct. 16, 2012 in 2 pages.
Planwise, http://planwise.com printed Feb. 8, 2013 in 5 pages.
Ponniah, Paulraj, "Data Warehousing Fundamentals: A Comprehensive Guide for IT Professionals", Wiley-Interscience Publication, pp. 257-289, 377-397, Aug. 3, 2001.
Porter, G. Zell, "An Economic Method for Evaluating Electronic Component Obsolescence Solutions", www.gidep.org/data/dmsms/library/zell.pdf, May 1998, pp. 1-9.
"PostX to Present at Internet Showcase", PR Newswire, Apr. 28, 1997, pp. 2.
PostX, "PostX® Envelope and ActiveView", http://web.archive.org/web/19970714203719/http://www.postx.com/priducts_fm.html, Jul. 14, 1997 (retrieved Nov. 7, 2013) in 2 pages.
"PremierGuide Announces Release 3.0 of Local Search Platform", Business Wire, Mar. 4, 2004, Palo Alto, CA, p. 5574.
Press Release—"Helping Families Protect Against Identity Theft—Experian Announces FamilySecure.com; Parents and guardians are alerted for signs of potential identity theft for them and their children; product features an industry-leading $2 million guarantee"; PR Newswire; Irvine, CA; Oct. 1, 2007.
PrivacyGuard, http://web.archive.org/web/20110728114049/http://www.privacyguard.com/ as archived Jul. 28, 2011 in 1 page.
Privacy Rights Clearinghouse, "Identity Theft: What to do if it Happens to You," http://web.archive.org/web/19990218180542/http://privacyrights.org/fs/fs17a.htm printed Feb. 18, 1999.
"Qualifying for Debt Settlement", http://www.certifieddebt.com/debt/settlement-qualifications.shtml printed Jan. 9, 2013 in 2 pages.
Quantix Software, "Investment Account Manager," available at https://www.youtube.com/watch?v=1UwNTEER1Kk, as published Mar. 21, 2012.
Quicken Online by Intuit http://www.quicken.intuit.com/, as retrieved on Sep. 17, 2008.
"Quicken Support", http://web.archive.org/web/20071231040130/http://web.intuit.com/support/quicken/docs/d_qif.html as archived Dec. 31, 2007 in 6 pages.
Rahm, et al. "Data Cleaning: Problems and Current Approaches", Bulletin of the IEEE Computer Society Technical Committee on Data Engineering, Dec. 2000, vol. 23, No. 4, pp. 11.
Raman, et al., "Potter's Wheel: An Interactive Data Cleaning System", Proceedings of the 27th VLDB Conference, Roma, Italy, 2001, pp. 10.
Ramaswamy, Vinita M., Identity-Theft Toolkit, The CPA Journal, Oct. 1, 2006, vol. 76, Issue 10, pp. 66-70.
Rawe, Julie; "Identity Thieves", Time Bonus Section, Inside Business, Feb. 2002, pp. 2.
Repici et al., "The Comma Separated Value (CSV) File Format", http://creativyst.com/Doc/Articles/CSV/CSV01.htm, Creativyst, Inc., 2002, pp. 10.
Reppler.com, "Learn More: Basic Information about howTrustedID Reppier Works for You," www.reppler.com/learn/ printed Oct. 24, 2012 in 2 pages.
"Resolve Debt for Less: With Help from Freedom Financial" http://www.debtsettlementusa.com/ printed Jan. 9, 2013 in 6 pages.
Romig, Shane, "The Truth About Credit Repair", Credit.com, May 5, 2010, http://web.archive.org/web/20100505055526/http://www.credit.com/credit_information/credit_help/The-Truth-About-Credit-Repair.jsp printed Mar. 22, 2013 in 4 pages.

(56) References Cited

OTHER PUBLICATIONS

Roos, Gina, "Web-Based Service Helps OEMs Cure Parts Obsolescence Blues", Electronic Engineering Times, Oct. 8, 2001, p. 86.
Roth, Andrew, "CheckFree to Introduce E-Mail Billing Serving," American Banker, New York, Mar. 13, 2001, vol. 166, No. 49, pp. 3.
Sakimura et al., "OpenID Connect Core 1.0 Incorporating Errata Set 1", https://openid.net/specs/openid-connect-core-1_0.html, Nov. 8, 2014, pp. 78.
Santarini, Michael, "Forecasts the Probable Obsolescence of Components—Module Predicts Parts Life", Electronic Engineering Times, Jan. 11, 1999, vol. 1, p. 48.
SAS, "SAS® Information Delivery Portal", Fact Sheet, 2008, in 4 pages.
Sawyers, Arlena, "NADA to Offer Residual Guide", Automotive News, May 22, 2000, p. 1.
Sax, Michael M., Data Collection and Privacy Protection: An International Perspective, Presentation: Managing Online Risk and Liability Conference, Aug. 31, 1999, pp. 58.
Schneier, B. "Applied Cryptography", John Wiley & Sons, Second Edition, pp. 435-447, 1996.
Schmidt et al., "A Set of Multi-Touch Graph Interaction Techniques", ITS '10, Nov. 7-10, 2010, Saarbrucken, Germany, pp. 1-4.
Scholastic Inc.:Parent's Request for Information http://web.archive.org/web/20070210091055/http://www.scholastic.com/inforequest/index.htm as archived Feb. 10, 2007 in 1 page.
Scholastic Inc.:Privacy Policy http://web.archive.org/web/20070127214753/http://www.scholastic.com/privacy.htm as archived Jan. 27, 2007 in 3 pages.
"ScoreNet® Network", FairIsaac, web.archive.org/web/20071009014242/http://www.fairisaac.com/NR/rdonlyres/AC4C2F79-4160-4E44-B0CB-5C899004879A/0/ScoreNetnetworkBR.pdf, May 2006, pp. 6.
Screenshot for Investment Account Manager v.2.8.3, published at http://www.aaii.com/objects/get/1642.gif by at least Aug. 30, 2011 in 1 page.
Sealey, Geraldine, "Child ID Theft Can Go Unnoticed for Years", http://abcnews.go.com/US/story?id=90257, Sep. 12, 2003 in 9 pages.
Securities and Futures Commission, "Guideline on Anti-Money Laundering and Counter-Terrorist Financing", Jul. 2012, pp. 135.
"Settling Your Debts—Part 1 in Our Debt Settlement Series", http://www.creditinfocenter.com/debt/settle_debts.shtml printed Jan. 9, 2013 in 6 pages.
Shin, Laura, "See An Error on Your Credit Report? Credit Karma Now Makes It Easy to Dispute", Nov. 12, 2015, http://www.forbes.com/sites/laurashin/2015/11/12/see-an-error-on-your-credit-report-credit-karma-now-makes-it-easy-to-dispute/, pp. 4.
ShoeBoxed, https://www.shoeboxed.com/sbx-home/ printed Oct. 16, 2012 in 4 pages.
Simpson, Glyn, "Microsoft (MS) Money MSMoney FAQ, Help and Information Pages", pp. 2, Copyright © Glyn Simpson 1998-2007, http://web.archive.org/web/20071018075531/http://money.mvps.org/faq/article/196.aspx.
Singletary, Michelle, "The Littlest Victims of ID Theft", The Washington Post, The Color of Money, Oct. 4, 2007.
Smith, Richard M., "The Web Bug FAQ", Nov. 11, 1999, Version 1.0, pp. 4.
Smith, Wendell R., "Product Differentiation and Market Segmentation as Alternative Marketing Strategies", The Journal of Marketing, The American Marketing Association, Brattleboro, Vermont, Jul. 1956, vol. XXI, pp. 3-8.
So et al., "Modelling and Model Validation of the Impact of the Economy on the Credit Risk of Credit Card Portfolios", The Journal of Risk Model Validation (93-126), vol. 4, No. 4, Winter (Year: 2010).
Srinivasa et al., "Augmented Reality Adaptive Web Content", 2016 13th IEEE Annual w Consumer Communications & Networking Conference (CCNC), pp. 4.
"STAGG Variables Sum Up Credit Attributes for Automated Decisions", PRWeb, May 11, 2011, pp. 2. http://www.prweb.eom/releases/2011/5/prweb8404324.htm.
Stallings, W. "Cryptography and Network Security Principles and Practice", Prentice Hall, Second Edition, pp. 295, 297, Jul. 15, 1998.
Stauffer et al., "Using HTML 3.2," Second Edition, 1996, Que Publishing, pp. 192-193.
Stone, "Linear Expenditure Systems and Demand Analysis: An Application to the Pattern of British Demand", The Economic Journal: The Journal of the Royal Economic Society, Sep. 1954, pp. 511-527, vol. LXIV, Macmillan & Co., London.
Sullivan, Laurie, "Obsolete-Parts Program Thriving", EBN, Manhasset, NY, Jan. 21, 2002, Issue 1296, p. 26.
Sun, Hung-Min, "An Efficient Remote Use Authentication Scheme Using Smart Cards", IEEE Transactions on Consumer Electronics, Nov. 2000, vol. 46, No. 4, pp. 958-961.
Tajik, S., "Conditional Plotting, Changing Color of Line Based on Value", MathWorks®, MATLAB Answers™, Question Posted Feb. 10, 2011 to https://www.mathworks.com/matlabcentral/answers/1156-conditional-plotting-changing-color-of-line-based-on-value?requestedDomain=www.mathworks.com, pp. 8.
Tan et al., "Modeling of Web Robot Navigational Patterns", 2000, Department of Computer Science; University of Minnesota, pp. 7.
Tao, Lixin, "Shifting Paradigms with the Application Service Provider Model"; Concordia University, IEEE, Oct. 2001, Canada.
Target, "Free Credit Monitoring and Identity Theft Protection with Experian's ProtectMyID Now Available", Jan. 13, 2014, pp. 2. http://corporate.target.com.
Tennant, Don, "How a Health Insurance Provider Uses Big Data to Predict Patient Needs," http://www.itbusinessedge.com/blogs/from-under-the-rug/how-a-health-insurance-provider-uses-big-data-to-predict-patient-needs.html, printed Mar. 6, 2014 in 2 pages.
TheMorningCall.Com, "Cheap Ways to Foil Identity Theft," www.mcall.com/business/columnists/all-karp.5920748jul01,0 . . . , published Jul. 1, 2007.
Thompson, Herbert H., "How I Stole Someone's Identity", https://www.scientificamerican.com/article/anatomy-of-a-social-hack/#, Aug. 18, 2008, pp. 5.
Todorova, Aleksandra, "Protecting Your Child's Identity", Smart Money, Published Aug. 2, 2007, pp. 1-5.
"TransUnion—Child Identity Theft Inquiry", TransUnion, http://www.transunion.com/corporate/personal/fraudIdentityTheft/fraudPrevention/childIDInquiry.page as printed Nov. 5, 2009 in 4 pages.
TransUnion Consumer Credit Report http://www.transunion.com/, as retrieved on Sep. 17, 2008.
Truston, "Checking if your Child is an ID Theft Victim can be Stressful," as posted by Michelle Pastor on Jan. 22, 2007 at http://www.mytruston.com/blog/credit/checking_if_your_child_is_an_id_theft_vi.html.
US Legal, Description, http://www.uslegalforms.com/us/US-00708-LTR.htm printed Sep. 4, 2007 in 2 pages.
"Use of Alternative Data to Enhance Credit Reporting to Enable Access to Digital Financial Services by Individuals and SMEs Operating in the Informal Economy", Guidance Note, International Committee on Credit Reporting (ICCR), Jun. 28, 2018, pp. 35.
Vamosi, Robert, "How to Handle ID Fraud's Youngest Victims," Nov. 21, 2008, http://news.cnet.com/8301-10789_3-10105303-57.html.
Various Posts from the http://www.2p.wrox.com Forums: http://web.archive.org/web/2005045221950/http://p2p.wrox.com/topic.asp?TOPIC_ID=6513 , dated Nov. 15, 2003-Oct. 7, 2004.
Waggoner, Darren J., "Having a Global Identity Crisis," Collections & Credit Risk, Aug. 2001, vol. vol. 6, No. 8, pp. 6.
Wang et al., "User Identification Based on Finger-vein Patterns for Consumer Electronics Devices", IEEE Transactions on Consumer Electronics, May 2010, vol. 56, No. 2, pp. 799-804.
"WashingtonPost.com and Cars.com Launch Comprehensive Automotive Web Site for the Washington Area", PR Newswire, Oct. 22, 1998. pp. 2.

(56) References Cited

OTHER PUBLICATIONS

Weaver et al., "Federated, Secure Trust Networks for Distributed Healthcare IT Services", IEEE International Conference on Industrial Informatics, 2003. INDIN 2003. Proceedings, 2003, pp. 162-169.
Web Page posted at: http://web.archive.org/web20040805124909/http://www.oracle.com/technology/sample_codete/tech/pl_sql/htdocs/x/Case/start.htm, pp. 1 and 4 of the webpages posted on Jan. 7, 2003.
Web Pages printed Nov. 2, 2004 of Internet Draft entitled "Tunneling SSL Through a WWW Proxy", Luotonen, Ari, Netscape Communications Corporation (Dec. 14, 1995); 4 pages. http://muffin.doit.org/docs/rfc/tunneling.sub.--ssl.html.
Webpage printed out from http://www.jpmorgan.com/cm/ContentServer?c=TS Content&pagename=jpmorgan%2Fts%2FTS_Content%2FGeneral&cid=1139403950394 on Mar. 20, 2008, Feb. 13, 2006, New York, NY.
Webster, Lee R., "Failure Rates & Life-Cycle Costs", Consulting-Specifying Engineer, Apr. 1998, vol. 23, No. 4, ABI/INFORM Global, p. 42.
Wesabe.com http://www.wesabe.com/, as retrieved on Sep. 17, 2008.
WhatIs.com, "Risk-Based Authentication (RBA)", https://web.archive.org/web/20121025033106/http://whatis.techtarget.com/definition/risk-based-authentication-RBA, Oct. 23, 2012, pp. 1.
Williams, Mark, "Results of the 1998 NASFAA Salary Survey", News from NASFAA, 1998.
Working, Holbrook, "Statistical Laws of Family Expenditure", Journal of the American Statistical Association, pp. 43-56, vol. 38, American Statistical Association, Washington, D.C., Mar. 1943.
Yahoo! Search, "People Search," http://people.yahoo/com printed Nov. 16, 2010 in 1 page.
YODLEE | Money Center, https://yodleemoneycenter.com/ printed Feb. 5, 2014 in 2 pages.
You Need a Budget, http://www.youneedabudget.com/features printed Feb. 5, 2014 in 3 pages.
Zandbergen, Paul A., "Ensuring Confidentiality of Geocoded Health Data: Assessing Geographic Masking Strategies for Individual-Level Data", Review Article, Hindawi Publishing Corporation, Advances in Medicine, VI. 2014, pp. 14.
Declaration of Paul Clark, DSc. for Inter Partes Review of U.S. Pat. No. 8,504,628 (Symantec Corporation, Petitioner), dated Jan. 15, 2014 in 76 pages.
Exhibit D to Joint Claim Construction Statement, filed in Epsilon Data Management, LLC, No. 2:12-cv-00511-JRG (E.D. Tex.) (combined for pretrial purposes with *RPost Holdings. Inc., et al.* v. *Experian Marketing Solutions. Inc.*, No. 2:12-cv-00513-JRG (E.D. Tex.)) Filed Jan. 14, 2014 in 9 pages.
First Amended Complaint in Civil Action No. 2:12-cv-511-JRG (*Rpost Holdings, Inc. and Rpost Communications Limited* V. *Constant Contact, Inc.; et al.*) filed Feb. 11, 2013 in 14 pages.
First Amended Complaint in Civil Action No. 2:12-cv-511-JRG (*Rpost Holdings, Inc. and Rpost Communications Limited* V. *Epsilon Data Management, LLC.*) filed Sep. 13, 2013 in 9 pages.
First Amended Complaint in Civil Action No. 2:12-cv-513-JRG (*Rpost Holdings, Inc. and Rpost Communications Limited* V. *Experian Marketing Solutions, Inc.*) filed Aug. 30, 2013 in 9 pages.
Petition for Covered Business Method Patent Review in U.S. Pat. No. 8,161,104 (*Experian Marketing Solutions, Inc., Epsilon Data Management, LLC, and Constant Contact, Inc.*, v. *Rpost Communications Limited*) dated Jan. 29, 2014 in 90 pages.
Source Code Appendix attached to U.S. Appl. No. 08/845,722 by Venkatraman et al., Exhibit A, Part 1 & 2, pp. 32.
International Search Report and Written Opinion in PCT Application No. PCT/US07/76152, dated Mar. 20, 2009.
Official Communication in Australian Patent Application No. 2012281182, dated Jul. 8, 2014.
Official Communication in Australian Patent Application No. 2012281182, dated May 19, 2015.
Official Communication in Chinese Patent Application No. 201280041782.2, dated Mar. 4, 2016.
Official Communication in European Patent Application No. 12811546.6, dated Nov. 25, 2014.
Official Communication in European Patent Application No. 12811546.6, dated Sep. 18, 2015.
Official Communication in Indian Patent Application No. 490/DELNP/2014, dated Jun. 20, 2019.
Official Communication in Russian Patent Application No. 2014101674/08, dated Dec. 15, 2014.
International Search Report and Written Opinion for Application No. PCT/US2012/046316, dated Sep. 28, 2012.
International Preliminary Report on Patentability and Written Opinion for Application No. PCT/US2012/046316, dated Jan. 14, 2014.
International Search Report and Written Opinion for Application No. PCT/US09/60393, dated Dec. 23, 2009.
International Search Report and Written Opinion for Application No. PCT/US09/37565, dated May 12, 2009.
International Search Report and Written Opinion for Application No. PCT/US2010/034434, dated Jun. 23, 2010.
International Preliminary Report on Patentability for Application No. PCT/US2010/034434, dated Feb. 4, 2014.
International Search Report and Written Opinion for Application No. PCT/US2013/052342, dated Nov. 21, 2013.
International Preliminary Report on Patentability for Application No. PCT/US2013/052342, dated Feb. 5, 2015.
Partial Supplementary European Search Report for Application No. EP12747205, dated May 14, 2020.
Extended European Search Report for Application No. EP12747205, dated Aug. 14, 2020.
International Search Report and Written Opinion for Application No. PCT/US2018/016258, dated May 16, 2018.
International Preliminary Report on Patentability in Application No. PCT/US2018/016258, dated Aug. 15, 2019.
Official Communication in Australian Patent Application No. 2014318966, dated Apr. 6, 2019.
Official Communication in Australian Patent Application No. 2019261724, dated Sep. 1, 2020.
Official Communication in Canadian Patent Application No. 2,923,697, dated Oct. 9, 2019.
Extended European Search Report for Application No. EP14843372.5, dated May 2, 2017.
Official Communication in European Application No. EP14843372.5 dated Nov. 29, 2018.
Extended European Search Report for Application No. EP19203040.1, dated Jan. 29, 2020.
International Search Report and Written Opinion for Application No. PCT/US2014/054713, dated Dec. 15, 2014.
International Preliminary Report on Patentability in Application No. PCT/US2014/054713, dated Mar. 24, 2016.
Official Communication in Australian Patent Application No. 2006306790, dated Apr. 29, 2010.
Official Communication in Australian Patent Application No. 2006306790, dated May 19, 2011.
International Search Report and Written Opinion for Application No. PCT/US2006/028006, dated Jul. 27, 2007.
International Preliminary Report on Patentability in Application No. PCT/US2006/028006, dated Apr. 23, 2008.
International Search Report and Written Opinion for Application No. PCT/US2019/037547, dated Oct. 4, 2019.
International Preliminary Report on Patentability in Application No. PCT/US2019/037547, dated Dec. 30, 2020.
International Search Report and Written Opinion for Application No. PCT/US2019/049377, dated Dec. 20, 2019.
International Search Report and Written Opinion for Application No. PCT/US2021/015566, dated May 11, 2021.
Application as filed in U.S. Appl. No. 09/411,683, dated Oct. 4, 1999.
"12 Mag: How Debt Settlement is Helpful in Improving the Credit Score", Weblog post. Newstex Trade & Industry Blogs, Newstex, Oct. 8, 2017, pp. 2.
Aad et al., "NRC Data Collection and the Privacy by Design Principles", IEEE, Nov. 2010, pp. 5.

(56) References Cited

OTHER PUBLICATIONS

Caldeiira et al., "Characterizing and Preventing Chargebacks in Next Generation Web Payments Services", 2012 Fourth International Conference on Computational Aspects of Social Networks (CASoN), 2012 IEEE, pp. 333-338.
Gramazio, Connor C., "Colorgorical: Creating Discriminable and Preferable Color Palettes for Information Visualization", IEEE Transactions on Visualization and Computer Graphics, Jan. 2017, vol. 23, No. 1, pp. 521-530.
Haglund, Christoffer, "Two-Factor Authentication with a Mobile Phone", Fox Technologies, Uppsala, Department of Information Technology, Nov. 2, 2007, pp. 62.
Koka et al., "Online Review Analysis by Visual Feature Selection", 2017 IEEE 15th Intl Conf on Dependable, Autonomic and Secure Computing, 15th Intl Conf on Pervasive Intelligence and Computing, 3rd Intl Conf on Big Data Intelligence and Computing and Cyber Science and Technology Congress (DASC/PiCom/DataCom/CyberSciTech), 2017, pp. 1084-1091.
Peng et al., "Factors Affecting Online Purchase Behavior: Implications to Improve the Existing Credit Rating System", 2009 International Conference on Management and Service Science, 2009 IEEE, pp. 1-4.
Phinisee, Tamarind, "Banks, FTC Step Up Efforts to Address Identity Theft", San Antonio Business Journal; San Antonio, Jul. 5, 2002, vol. 16, No. 24, pp. 5.
Shibata et al., "3D Retrieval System Based on Cognitive Level—Human Interface for 3D Building Database", Proceedings of the 2004 International Conference on Cyberworlds (CW'04), 2004, pp. 6.
Solapurkar, Prajakta, "Building Secure Healthcare Services Using OAuth 2.0 and JSON Web Token in IOT Cloud Scenario", IEEE, 2nd International Conference on Contemporary Computing and Informatics (ic3i), 2016, pp. 99-104.
Willems et al., "On the Security and Privacy of Interac e-Transfers", School of Electrical Engineering and Computer Science, Faculty of Engineering, University of Ottawa, Extended Version, Dec. 10, 2019, pp. 47.
Official Communication in Australian Patent Application No. 2018215082, dated Jan. 21, 2022.
Extended European Search Report for Application No. EP12747205, dated Feb. 11, 2022.
Official Communication in Indian Patent Application No. 201917029540, dated Jan. 7, 2022.
Extended European Search Report for Application No. EP21183630.9, dated Oct. 15, 2021.
International Preliminary Report on Patentability in Application No. PCT/US2021/015566, dated Aug. 11, 2022.

* cited by examiner

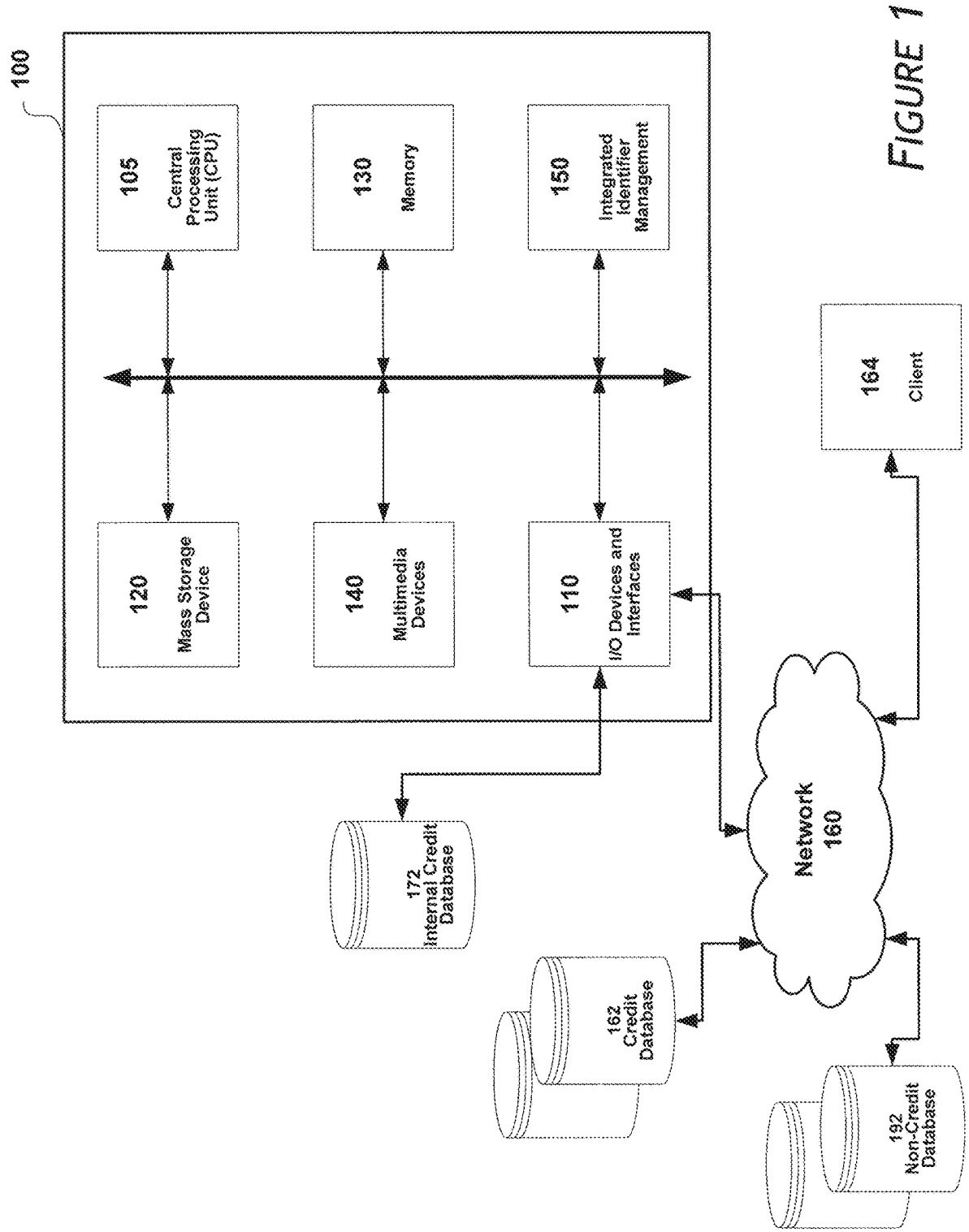

SYSTEMS AND METHODS FOR PROVIDING AN INTEGRATED IDENTIFIER

CROSS-REFERENCE TO RELATED APPLICATIONS

This application is a continuation application of U.S. application Ser. No. 16/053,698, filed on Aug. 2, 2018, entitled "SYSTEMS AND METHODS FOR PROVIDING AN INTEGRATED IDENTIFIER," which is a continuation application of U.S. patent application Ser. No. 14/617,062, filed on Feb. 9, 2015, entitled "SYSTEMS AND METHODS FOR PROVIDING AN INTEGRATED IDENTIFIER," which is a continuation application of U.S. patent application Ser. No. 13/673,918, filed on Nov. 9, 2012, entitled "SYSTEMS AND METHODS FOR PROVIDING AN INTEGRATED IDENTIFIER," which is a continuation application of U.S. patent application Ser. No. 12/493,115, filed on Jun. 26, 2009, entitled "SYSTEMS AND METHODS FOR PROVIDING AN INTEGRATED IDENTIFIER," which claims the benefit of priority from U.S. Provisional Patent Application No. 61/076,139 filed on Jun. 26, 2008, entitled "Systems and Methods for Providing an Integrated Identifier." The entire contents of the above reference applications are hereby expressly incorporated herein by reference in their entirety. All publications and patent applications mentioned in this specification are herein incorporated by reference in their entirety to the same extent as if each individual publication or patent application was specifically and individually indicated to be incorporated by reference.

BACKGROUND

Field of the Invention

This disclosure generally relates to data processing, and more particularly to methods and systems for providing an integrated identifier for accessing differently regulated data.

Description of the Related Art

In the United States, the use of personal, credit, and financial data of consumers is regulated by at least the Fair Credit Reporting Act (FCRA) and the Gramm-Leach-Bliley Act (GLB). For example, under the FCRA, credit data may be used under certain permissible purposes, such as for account review purposes when a consumer already has an established account with a financial institution. In the healthcare field, the Health Insurance Portability and Accountability Act (HIPAA) governs the use of patient data. Organizations often need to manage customer or patient data including different types of data governed by different legal requirements, and thus face the challenge of complying with those requirements in the management of differently regulated data. The different legal requirements often lead to the use of parallel and sometimes duplicative data management systems and methods that increase the transfer of private or sensitive data across systems and networks. Besides increasing costs, the increased transfer also leads to increased security risks and exposes those organizations to liability for data privacy breaches.

SUMMARY OF THE DISCLOSURE

Embodiments described herein provide data management systems and methods for accessing, providing, and/or managing differently regulated data. The data management systems and methods may streamline the mechanism by which data users access both regulated and non-regulated data through the use of one or more integrated identifiers. An identifier may be an alphanumeric string and/or a database record key. It may be encrypted or in clear text. In one or more embodiments an identifier does not contain any personally identifiable information. Other embodiments include systems and methods that allow for the integration of a Customer Data Integration (CDI) solution with an account review service through the use of one or more integrated identifiers.

In one embodiment, the integrated identifiers are managed by a reconciliation system that (1) reconciles various identifiers in use in regulated and non-regulated data sources into the single integrated identifiers and (2) resolve the integrated identifiers and translate them back to the various identifiers for accessing regulated and non-regulated data sources. The reconciliation and resolution logic takes into account the potential mismatches in the data records concerning the same individual consumers or businesses, including the various possibilities when there is not a one-to-one correspondence. The reconciliation system accomplishes its tasks while maintaining compliance with various legal requirements concerning regulated data. Therefore, the systems and methods may lessen or eliminate the need to separately maintain one set of identifiers for regulated data and another set for non-regulated data. The methods and systems may be applicable in various credit and healthcare contexts where regulations over data use are prevalent.

In one embodiment, a data user receives a unique integrated data identifier for each of the data user's current or prospective customers, which may be individual consumers or businesses. The integrated data identifiers can be used by the data user to persistently identify and track the customers over time and across software applications. The integrated data identifier can also be accurately and consistently translated within a data provider (such as a credit bureau) to link and deliver corresponding consumer and business data within the varying asset databases and services maintained by the data provider. In the healthcare context, a healthcare provider or an insurer may utilize a patient ID as the integrated identifier. In one or more embodiments, to protect privacy, the integrated identifier does not include personal information such as social security numbers or birthdates.

BRIEF DESCRIPTION OF THE DRAWINGS

Specific embodiments will now be described with reference to the following drawings:

FIG. 1 is a block diagram of an integrated identifier reconciliation system according to one embodiment.

DESCRIPTION OF CERTAIN EMBODIMENTS

Figure 2A:
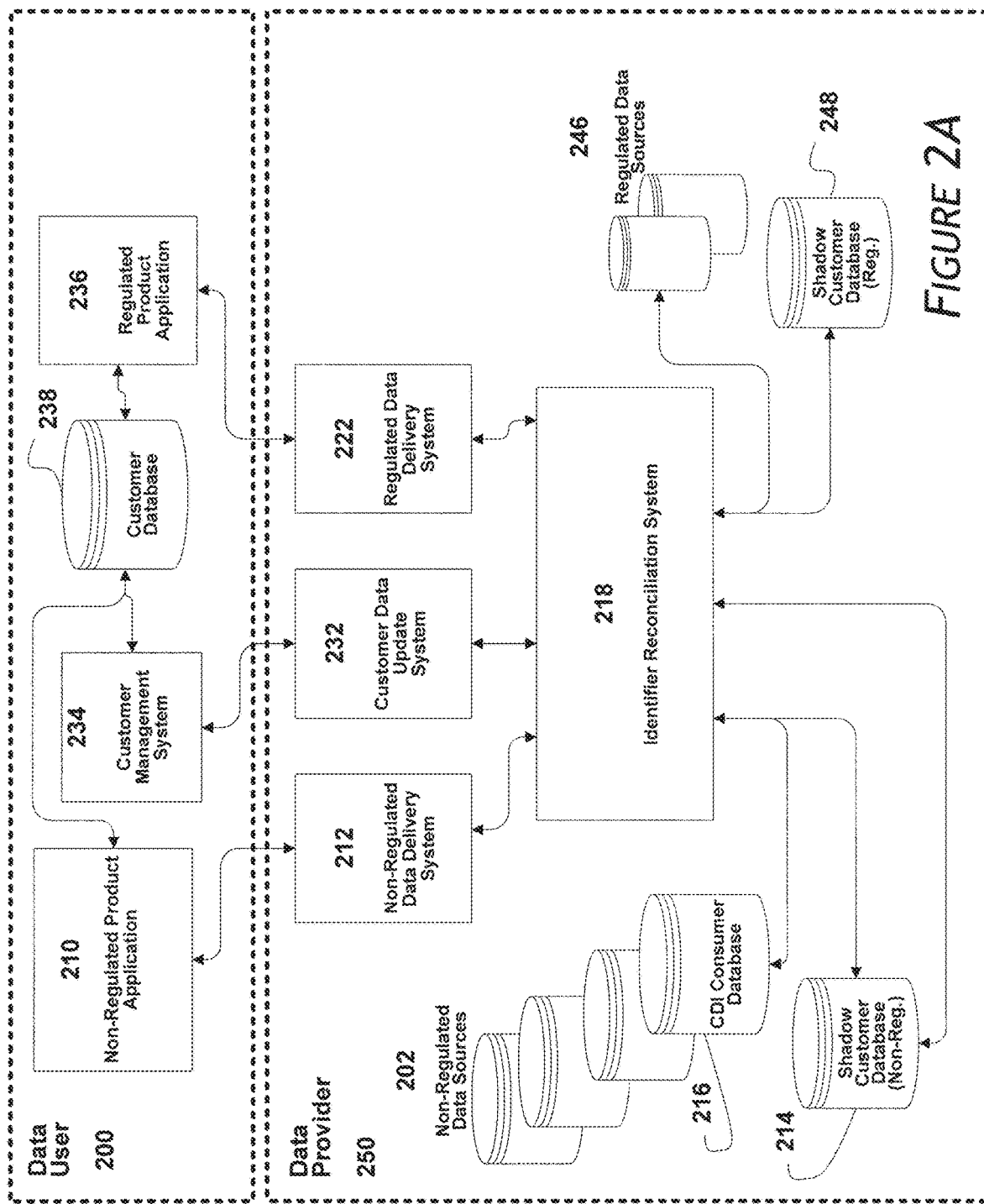
FIG. 2A is a block diagram showing a system for providing and utilizing integrated identifiers according to one embodiment.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions described herein.

Various companies store information about their customers in a collection of systems and databases. Customer data integration ("CDI") solutions, such as Experian's Truvue solution, synchronize records across multiple business units and databases to deliver a more complete, consistent and accurate view of customers over time. One advantage of a CDI solution may be that it can integrate thousands of reliable and verifiable data sources (collectively referred to as "customer data") into one or more large intelligent reference databases. With links to thousands of contributors of reliable and verifiable data, information may be updated continually. When combined with vast name and address history stored by a credit bureau, these links may give a data user entity that uses the CDI the ability to accurately identify and link comprehensive data to their customers.

Many data users, such as credit card issuers, banks, utility companies, and other commercial entities, for example, need to manage customer data. In addition, these data users often access regulated data such as credit data, sometimes in conjunction with one or more access operations involving non-regulated customer data. For example, a card issuer may wish to use non-regulated customer data for marketing purposes and regulated credit data for processing new credit applications. One difficulty these data users encounter is the divergent methods of access that are needed due to the different regulations restricting the use of certain data. Other data users in fields such as healthcare may also face the same challenge in their data management practices. For example, a healthcare provider or an insurer may face one set of legal requirements with regard to patient data (e.g., HIPPA) and another set of requirements with regard to the use of credit data related to those patients (e.g., FCRA). For example, a pharmacy may need to manage three types of regulated data: medical data, insurance data, and credit data.

Typically the legal requirements limit use of data to certain permissible purposes, and as a result the different legal requirements often lead to the use of parallel and sometimes duplicative data management systems and methods that cannot be cross-referenced. For example, if a credit card company purchased a marketing list (usually non-regulated) containing prospective customers and wished to check the list against its current account holders in a regulated credit database, legal requirements may require the company to assign identifiers to the prospective customers on the marketing list, assign the same identifiers to its list of current account holders, and then compare the two lists. However, according to certain embodiments discussed herein, the credit card company may provide the list of prospective customers to a system that will automatically resolve, in a compliance manner, to the proper integrated identifiers that also correspond to the identifiers used in the regulated credit database.

Embodiments described herein provide data management systems and methods for accessing, providing, and/or managing differently regulated data. The data management systems and methods streamline the mechanism by which data users access both regulated and non-regulated data through the use of one or more integrated identifiers. An identifier may be an alphanumeric string and/or a database record key. It may be encrypted or in clear text. In one or more embodiments an identifier does not contain any personally identifiable information. Other embodiments include systems and methods that allow for the integration of a Customer Data Integration (CDI) solution with an account review service through the use of one or more integrated identifiers. Embodiments may also ensure that the use of these regulated data in the integrated environment is still consistent with the legal requirements concerning use. In one embodiment, the systems and methods are configured to comply with various federal and state legislations.

In addition, the systems and methods may minimize or reduce the need to transfer consumer private data to the data provider, for example, for the purpose of conducting the account review services or other services. The systems and methods may also help identify other service opportunities for improving efficiency and/or quality, as well as other services that can utilize the integrated identifier.

Integrated Identifier

Embodiments employ one or more integrated identifiers for the interface and delivery of multiple products and services derived from various data sources, including but not limited to those from a data provider such as a credit bureau.

In one embodiment, a data user (e.g., a client of the credit bureau or a client of a data provider) can receive a unique integrated identifier for each of the data user's current or prospective customers, which may be a consumer or a business. Other data providers may include insurance companies, healthcare providers, etc. The unique integrated identifiers can be used by the data user to persistently identify and track both regulated and/or non-regulated data associated with its customers over time and across applications. In one embodiment, a credit processing software application may interface with a data provider, such as a credit bureau, that delivers consumer and business data from within the regulated and/or non-regulated databases and services maintained by the data provider. In the healthcare context, a healthcare provider or an insurer may utilize a patient ID as the integrated identifier. In one or more embodiments, to protect privacy, the integrated identifier does not include personal information such as social security numbers or birthdates. In one embodiment, the integrated identifier is from a data provider, and in one embodiment the integrated identifier is from a data user. The integrated identifier may be an existing identifier in either the data user or the data provider's database, or a new identifier.

In one embodiment, existing marketing data services solution infrastructure and/or customer database solutions may be used as a platform for building and maintaining a cross reference between corresponding consumers on a truth database (e.g., Experian Marketing Services' Truth Database) and a credit database maintained by a credit bureau (e.g., Experian's File One Database).

One or more embodiments are configured so that the use of designed integrated identifiers does not change the regulatory status of any of the credit bureau's core asset database(s). In one embodiment, the integrated identifier includes safeguards that will prohibit it from being incorrectly used or referenced within the data provider's and within the data user's systems and applications. In one embodiment used in the credit context, the system prevents the integrated identifier from being used as an alternative identifier for defining a consumer associated with a credit account when reporting account updates to a credit bureau's primary credit database. Instead, updates need to comply with consumer credit reporting standards, such as the "Metro2" standard defined by the Associated Credit Bureaus, Inc (ACB).

Computing System

In some embodiments, the systems, computer clients and/or servers described herein take the form of a computing system as shown in FIG. 1. FIG. 1 is a block diagram showing an embodiment in which computing system 100 is in communication with a network 160 and various systems are also in communication with the network 160. The computing system 100 may be used to implement systems and methods described herein. For example, the computing system 100 may be configured to receive financial and demographic information regarding individuals and generate reports and/or alerts for one or more clients. Although the description provided herein refers to individuals, consumers, or customers, the terms "individual," "consumer," and "customer" should be interpreted to include applicants, or groups of individuals or customers or applicants, such as, for example, married couples or domestic partners, organizations, groups, and business entities.

The computing system 100 includes, for example, a server or personal computer that is IBM, Macintosh, or Linux/Unix compatible. In one embodiment, the computing system 100 comprises a server, a laptop computer, a cell phone, a personal digital assistant, a kiosk, or an audio player, for example. In one embodiment, the exemplary computing system 100 includes one or more central processing unit ("CPU") 105, which may include a conventional microprocessor. The computing system 100 further includes one or more memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standard based bus system. In different embodiments, the standard based bus system could be Peripheral Component Interconnect ("PCI"), Microchannel, Small Computer System Interface ("SCSI"), Industrial Standard Architecture ("ISA") and Extended ISA ("EISA") architectures, for example. In addition, the functionality provided for in the components and modules of computing system 100 may be combined into fewer components and modules or further separated into additional components and modules.

The computing system 100 is generally controlled and coordinated by operating system software, such as Windows 95, Windows 98, Windows NT, Windows 2000, Windows XP, Windows Vista, Windows 7, Unix, Linux, SunOS, Solaris, or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, I/O services, and provide a user interface, such as a graphical user interface ("GUI"), among other things.

The exemplary computing system 100 includes one or more commonly available input/output (I/O) devices and interfaces 110, such as a keyboard, mouse, touchpad, and printer. In one embodiment, the I/O devices and interfaces 110 include one or more display device, such as a monitor, that allows the visual presentation of data to a user. More particularly, a display device provides for the presentation of GUIs, application software data, and multimedia presentations, for example. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is electronically coupled to a network 160, which comprises one or more of a LAN, WAN, or the Internet, for example, via a wired, wireless, or combination of wired and wireless, communication link 115. The network 160 communicates with various computing devices and/or other electronic devices via wired or wireless communication links.

According to FIG. 1, information is provided to computing system 100 over the network 160 from one or more data sources including, for example, credit databases 162. The information supplied by the various data sources may include credit data, demographic data, application information, product terms, accounts receivable data, and financial statements, for example. In addition to the devices that are illustrated in FIG. 1, the network 160 may communicate with other data sources or other computing devices. In addition, the data sources may include one or more internal and/or external data sources. In some embodiments, one or more of the databases or data sources may be implemented using a relational database, such as Sybase, Oracle, CodeBase and Microsoft® SQL Server as well as other types of data structures such as, for example, a flat file database, an entity-relationship database, and object-oriented database, and/or a record-based database.

In addition to supplying data, client 164 may further request information from the computing system 100. For example, the client 164 may request data related to a consumer or a group of consumers. Such a request may include consumer information identifying the consumer(s) for which information is desired. The client may also provide updates to the one or more databases shown in the figure. For example, the client 164 may send, to the computing system 100, new account information when a customer opens a new credit card account so that one or more credit or non-credit databases reflects the customer's new account.

The I/O devices and interfaces 110 further provide a communication interface to an internal credit database 172. In the embodiment of FIG. 1, the computing system 100 is coupled to a secured network 161, such as a secured LAN, for example. The system 100 may communicate with the internal credit database 172 through a secured network (not shown), for example. In some embodiments, the internal credit database 172 is configured to communicate with additional computing devices over the network 160 or some other network, such as a LAN, WAN, and/or the Internet via a wired, wireless, or combination of wired and wireless, communication link. In certain embodiments, the client 164 may have access to the internal credit database 172 through the network 160.

In the embodiment of FIG. 1, the computing system 100 also includes an integrated identifier management module 150 that may be executed by the CPU 105. This module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In the embodiment shown in FIG. 1, the computing system 100 is configured to execute integrated identifier management module 150, among others, in order to reconcile identifiers and personal identification numbers associated with respective customers among the internal credit database 172, credit databases 162, and/or non-credit databases 192. The reconciliation process associate disparate identifiers to one or more integrated identifiers for the same customers, so that different data sources can be accessed with the integrated identifiers. The various reconciliation methods will be further described below. In some embodiments, the integrated identifier management module 150 may be configured to access and/or obtain data from internal credit database 172, credit databases 162, non-credit databases 192, or a combination of internal credit database 172, credit databases 162 and non-credit databases 192.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Providing Access to Non-Regulated and Regulated Data Sources

FIG. 2A is a block diagram showing a system for providing and utilizing integrated identifiers according to one embodiment. In the embodiment of FIG. 2A, a data user 200 can access various data sources provided by one or more data provider 250 (e.g., a credit bureau), including non-regulated data 202 and regulated data 246. As depicted in the figure, the data user 200 may operate a Non-Regulated Product Application 210, a Regulated Product Application 236, and/or a Customer Management System 234. The data user 200 may use the integrated identifiers throughout its applications and systems to refer to individuals or businesses, and use the same integrated identifiers to access regulated and non-regulated data provided by the data provider 250. In one or more embodiments, the reconciliation mechanisms employed by the data provider 250 eliminate the need for the data user 200 to maintain separate identifiers for regulated and non-regulated data for the same individuals or businesses.

Non-Regulated Data Sources

In one embodiment, the Non-Regulated Product Application 210 is tasked with accessing non-regulated data. For example, if the data user 200 is a credit card company, the Non-Regulated Product Application 210 may handle the tasks of gathering data to find prospective customers, verifying information relating those prospective customers, and pre-qualifying selected prospective customers for credit card offers. In one or more of these tasks, the Non-Regulated Product Application 210 accesses a Non-Regulated Data Delivery System 212, which serves as an interface to a number of databases containing non-regulated data sources 202 from which data may be accessed, acquired and/or verified. In one or more embodiments, the Non-Regulated Data Delivery System 212 is operated by the data provider 250.

Among non-regulated data sources 202 may be a CDI Consumer Database 216, which may serve as the primary data source for the Non-Regulated Data Delivery System 212 in one embodiment. The CDI Consumer Database 216 may also serve as the primary database in which the data user 200 correlates its customer data with other sources of non-regulated data. In one embodiment, CDI Consumer Database 216 stores a history of data points for the individual consumers identified. The data points may be retrieved from qualified data sources so that the CDI Consumer Database 216 provides consistent and accurate information about consumers. For example, the Non-Regulated Product Application 210 may send information of a prospective customer to the Non-Regulated Data Delivery System 212 to request a lookup of the prospective customer in one or more of the non-regulated data sources 202. The Non-Regulated Data Delivery System 212 may attempt to locate the prospective customer in the CDI Consumer Database 216 using the received information. The Non-Regulated Data Delivery System 212 may then return to the Non-Regulated Product Application 210 the non-regulated data identifier(s) of the matched record(s) within the CDI Consumer Database 216, along with other data from data sources 202 that are associated with the particular prospective customer. In one embodiment, the returned data include the matched record for the customer in the CDI Consumer Database 216, the ID (the identifier) for the matched record in the CDI Consumer Database 216, and/or other associated data records for that customer from other data sources 202. If no matches are found, a new non-regulated data identifier may be assigned and returned to the Non-Regulated Product Application 210. If multiple matches are found, the Identifier Reconciliation System 218 follows a reconciliation process that will be further described in detail below. In one embodiment, Identifier Reconciliation System 218 may be implemented as the computing system 100.

In one embodiment, the returned non-regulated data identifier serves as the integrated identifier through which other applications and systems of the data user 200 may access both regulated and non-regulated data. In some embodiments, the integrated identifiers can also access multiple sources of non-regulated data. In one embodiment, the returned integrated identifiers are saved in a Customer Database 238. In one embodiment, one integrated identifier is returned for each individual customer. With reference to flow chart in FIG. 2B, which is discussed in further detail below, the same returned identifiers are saved in a Non-Regulated Shadow Customer Database 214 in block 260 to facilitate the process of identifier reconciliation. In one embodiment, the Non-Regulated Shadow Customer Database 214 mirrors at least a portion of the records stored in the Customer Database 238 and links the records to the assigned integrated identifiers. An entry in the Non-Regulated Customer Shadow Database 214 may include a pairing of the customer's record in the customer database 238 with the non-regulated identifier that has been returned the customer.

Regulated Data Sources

Embodiments also provide methods and systems that enable data users to access regulated data sources with the identifiers that have been assigned as the integrated identifiers, which may also be used for accessing non-regulated data. In one embodiment, a Regulated Data Delivery System 222 provides an interface for accessing regulated data sources 246. For example, the Regulated Data Delivery System 222 may receive queries from the Regulated Product Application 236 to obtain credit reports for credit applicants. In one or more embodiments, the Regulated Data Delivery System 222 implements one or more rules to ensure that access to the regulated data sources complies with applicable legal requirements.

In one embodiment, the Regulated Product Application 236 may forward to the Regulated Data Delivery System 222 an identifier that has been assigned as the integrated identified and previously returned by the Non-Regulated Data Delivery System 212, along with other query data (e.g., name, Social Security Number) for the retrieval of regulated data. The Regulated Data Delivery System 222, may then access the regulated data sources, locate the records and the associated regulated data identifiers that match the query data, and return them to the Regulated Product Application 236.

Figure 2B:
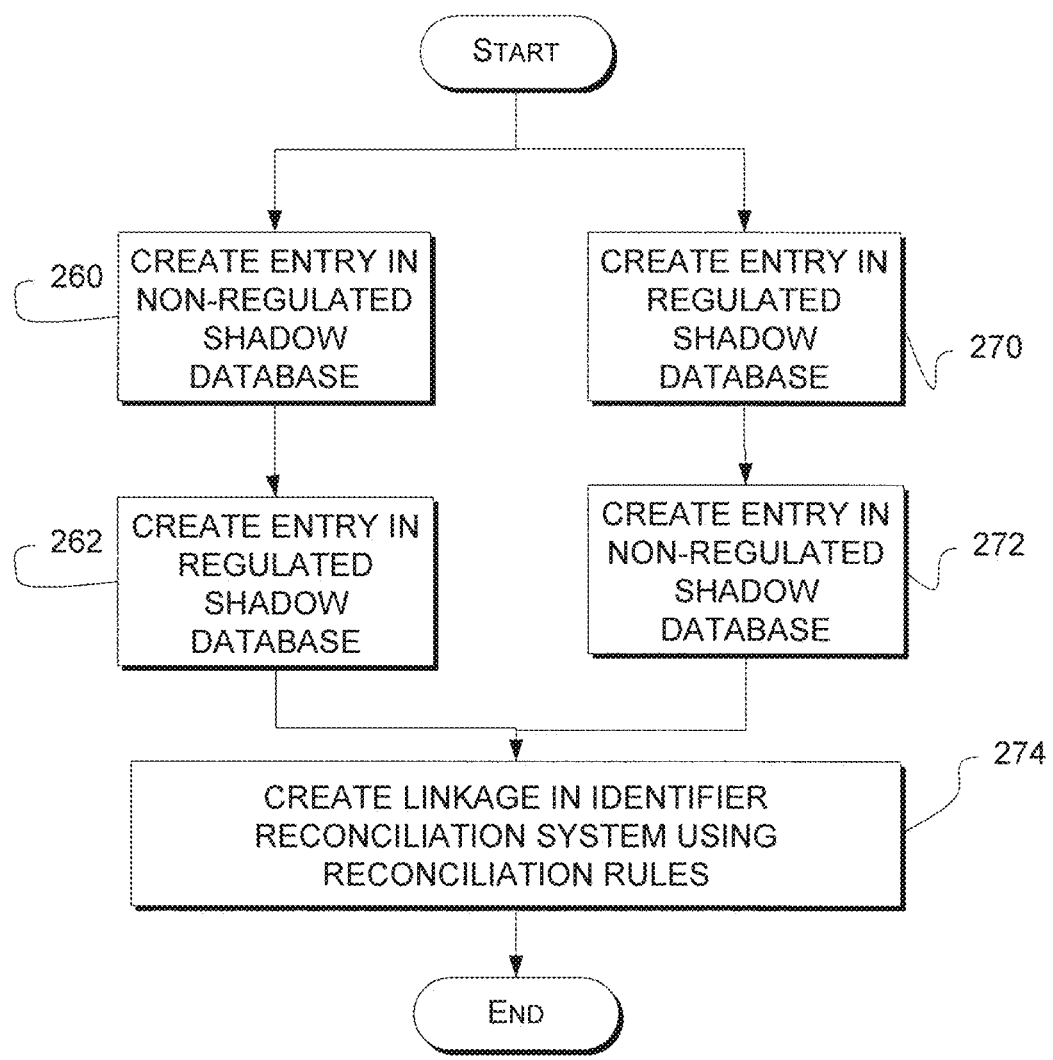
FIG. 2B is a flow diagram showing a method for reconciling integrated identifiers according to one embodiment.

FIG. 2B is a flow diagram showing a method for reconciling integrated identifiers according to one embodiment. In the embodiment of FIG. 2B, the lookup process may trigger (1) as shown in block 262, the creation of an entry in the Regulated Customer Shadow Database 248, and (2) as shown in block 274, the creation, within the Identifier Reconciliation System 218, of a linkage between the previously created entry in the Regulated Customer Shadow Database 218 and the corresponding entry in the Regulated Customer Shadow Database 248. In one embodiment, the Regulated Shadow Customer Database 248 mirrors at least a portion of the records stored in the Customer Database 238 and links the records to the located regulated data identifiers. In one embodiment, the linkage is created using a set of reconciliation rules as further described below. An entry in the Regulated Customer Shadow Database 248 may include a pairing of the customer's record in the customer database 238 with the regulated identifier for the customer. In one embodiment, the Regulated Customer Shadow Database 248 and the Non-Regulated Customer Shadow Database 214 may be implemented as distinct tables or data structures within one database.

As shown also by blocks 270 and 272 in FIG. 2B, the process of creating the linkage may occur in a different order if the data user accesses regulated data first and subsequently accesses non-regulated data. In one embodiment, this order is an alternative method of execution to that which is depicted in blocks 260 and 262. In this situation, a lookup of the non-regulated data source may be needed in block 270 to retrieve a non-regulated data identifier and provide it to the data user 200. In another embodiment, blocks 270 and 272 may take place concurrently with blocks 260 and 262, or before or after blocks 260 and 262.

Identifier Reconciliation

In one embodiment, the Identifier Reconciliation System 218 includes the integrated identifier management module 150 (from FIG. 1) that reconciles identifiers for regulated and non-regulated data. As described above, the Non-Regulated Shadow Database 214 and the Regulated Shadow Database 248 each keeps a shadow copy of the records in the Customer Database 238 with different identifiers. Hence, data accesses by the data user to various data sources with the integrated identifiers need to be reconciled or resolved properly. In one embodiment, the non-regulated data identifiers are used as the integrated identifiers, which are used in the Customer Database 238 and the Non-Regulated Shadow Database 214. In one embodiment, the regulated data identifiers are used in the Regulated Shadow Database 248.

In one embodiment, the reconciliation module reconciles identifiers for regulated and non-regulated data. In one embodiment, the integrated identifier management module 150 may follow one or more business rules in its reconciliation process. The rules account for the possibility that there may be one-to-one, many-to-one, or many-to-many correspondences between records in non-regulated data sources and those in regulated data sources. The rules may include one or more of the following:

(A) For the condition where a regulated data identifier (e.g., a unique PIN assigned by a credit bureau) is matched to a non-regulated data identifier (which may be used as the integrated identifier as described above), the link between the regulated data identifier and the non-regulated data identifier may be created and maintained in a data linkage table without additional processing.

(B) For the condition where multiple regulated data identifiers are matched to one non-regulated data identifier, the following rules may be used. (1) If the regulated identifiers are deemed indicative of duplicate data records in a regulated database, the Identifier Reconciliation System 218 may initiate an inquiry to the data user to trigger a merge of the multiple duplicative regulated data identifiers in the regulated database. (2) However, if data management mechanism associated with the regulated database does not allow such a merge, then new non-regulated identifiers may be created for each unique regulated data identifier.

(C) For the condition where multiple non-regulated data identifiers are matched to one regulated data identifier, the multiple non-regulated data identifiers may be merged into one inquiry at the CDI Consumer Database 216 in one embodiment and a resolution process is then executed to identify a resulting non-regulated data identifier that will be assigned to the credit data identifier.

(D) For the condition where a non-regulated data identifier does not match any regulated data identifier, an error message may be output for manual research & resolution. In some embodiments, a regulated data identifier may be created for the non-regulated data identifier.

(E) For the condition where a regulated data identifier does not match any non-regulated data identifiers, a new non-regulated data identifier may be created for the individual identified by the regulated data identifier. The non-regulated data identifier may be marked as private data, so that it is visible only to the data user that is requesting the reconciliation.

(F) For the condition where multiple regulated data identifiers match multiple non-regulated data identifiers, in one embodiment, the system is configured to follow the above rules regarding many-to-one correspondences.

It is to be understood that the above rules are implemented in one or more embodiments, for example, in embodiments where FCRA and/or GLB regulated data are used. Other embodiments, such as those in the healthcare context, may use different rules. In addition, the reconciliation rules used in various embodiments of the invention may be updated to ensure continued compliance with changing laws and regulations. In one or more embodiments, the Identifier Reconciliation System 218 is configured to periodically check a data source that provides a set of updated rules. Finally, although the examples above describe regulated and non-regulated data, the integrated identifiers are not so limited may be used to provide access to differently-regulated data, e.g. two or more sources of differently regulated data.

Identifier Resolution

With the linkage in place, the Identifier Reconciliation System 218 provides identifier resolution so that the data user 200 can access both regulated and non-regulated data with the integrated identifier. For example, the data user 200 may operate a Customer Management System 234 that handles tasks such as account creation and account maintenance. The Customer Management System 234 interacts with a Customer Data Update System 232, which manages transactions by also utilizing the Identifier Reconciliation System 218.

Figure 2C:
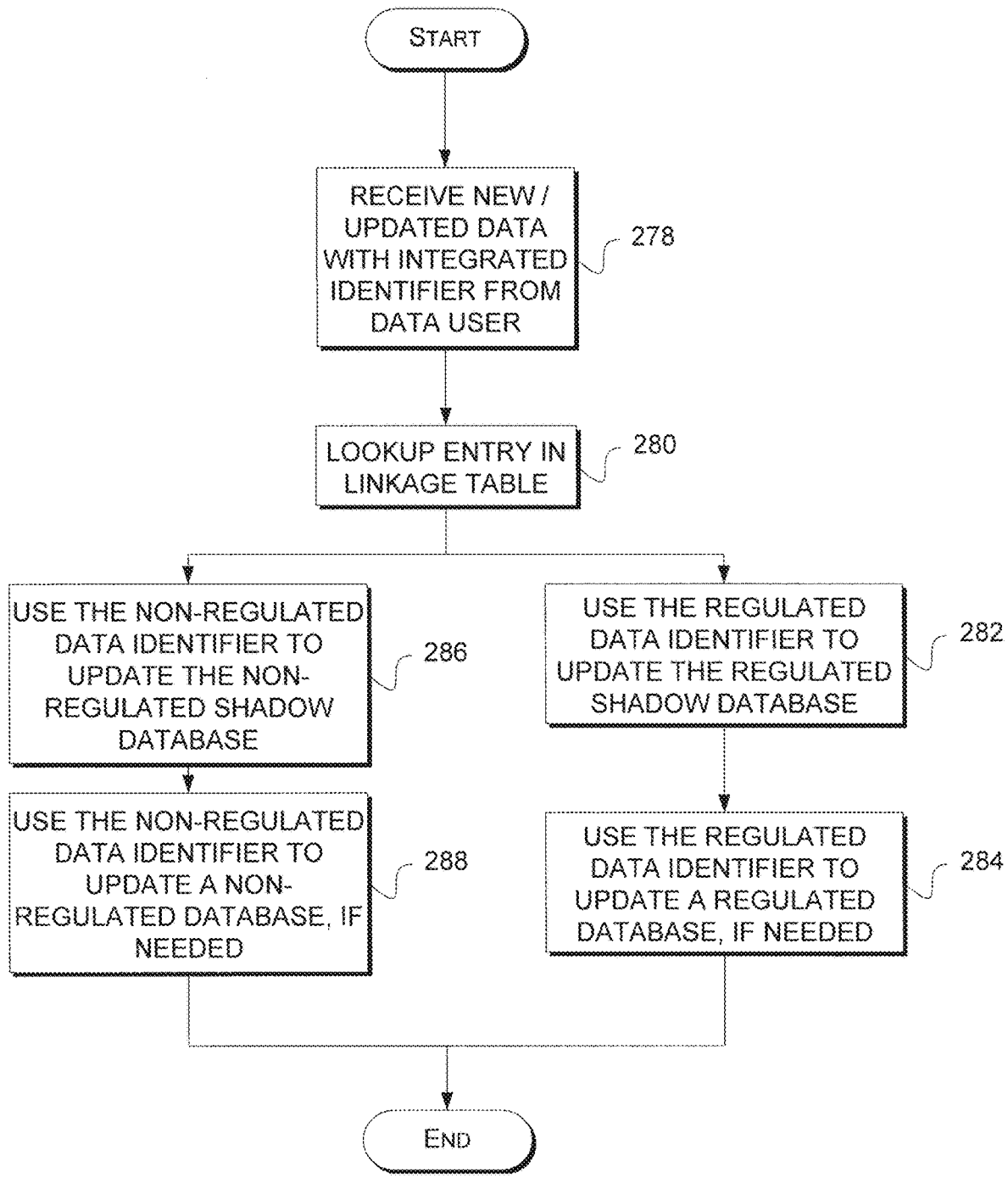
FIG. 2C is a flow diagram showing a method for resolving integrated identifiers according to one embodiment.

FIG. 2C is a flow diagram showing a method for resolving integrated identifiers according to one embodiment. An example of an identifier resolution process is described below with reference to FIG. 2C. Such an example may entail the creation of a new customer account. The Customer Management System 234 may create the new account in the Customer Database 238 with the integrated identifier. Then, in block 278, the Customer Data Update System 232 may receive, from the Customer Management System 234, the new account information along with the integrated identifier associated with the new customer, both of which may be passed to the Identifier Reconciliation System 218. The Identifier Reconciliation System 218 may then look up the appropriate entries in the linkage table in block 280. The lookup may resolve to identifiers usable for either an update to the Non-Regulated Shadow Customer Database 214 and/or the Regulated Shadow Customer Database 248, along with actual updates to the appropriate regulated or non-regulated data sources (blocks 282, 284, 286, and 288).

In one or more embodiments, systems 212, 222, and 232 may be part of the Identifier Reconciliation System 218, which serves as a central access point of any data applications of the data user. In addition, although the examples described above describe accessing data in individual transactions, systems 212, 222, and 232 in one or more embodiments may be configured to support batch processing where data records are processed in accordance with the mechanisms described above in batches.

Description of Other Embodiments Applied to Specific Contexts

Figure 3:
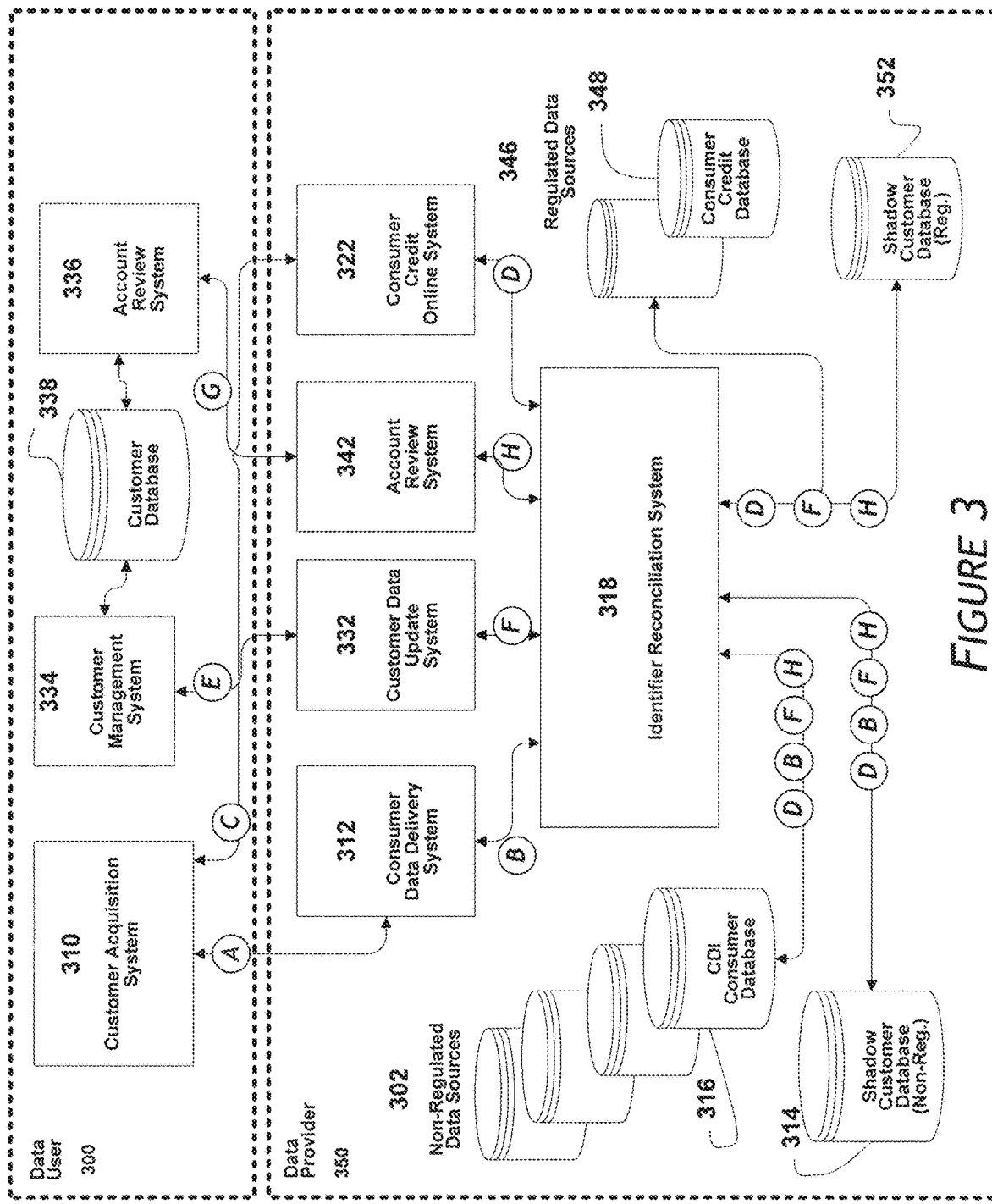
FIG. 3 is a block diagram showing a system for providing and utilizing integrated identifiers in accordance with another embodiment.

FIG. 3 shows an embodiment as applied in the credit context. A data user 300 can access various databases provided by a data provider 350, for example, a credit bureau, including non-regulated data 302 and regulated data 346 through the use of integrated identifiers. Non-regulated data 302 may include CDI data and other related data, while regulated data 346 may include credit data, including credit data used for account review purposes. As depicted in the figure, the data user may operate a Customer Acquisition System 310, which handles the task of acquiring new customers. For example, if the data user is a credit card company, Customer Acquisition System 310 may handle the tasks of gathering data to locate prospective customers, verifying information relating those prospective customers, and qualifying selected prospective customers for credit card offers. In another example, if the data user is a utility company, the Customer Acquisition System 310 may be used to determine a customer's eligibility to receive services. In the healthcare setting, the Customer Acquisition System 310 may be used by a healthcare provider to admit new patients.

In one or more of these tasks, the Customer Acquisition System 310 may access a Consumer Data Delivery System 312, which serves as an interface to a number of databases containing non-regulated data sources 302 from which data may be acquired and/or verified. In one or more embodiments, the Consumer Data Delivery System 312 is operated by the data provider 350.

Non-Regulated Data Sources

Among database sources 302 may be a CDI Consumer Database 316, which may serve as the primary data source for the Consumer Data Delivery System 312. The CDI Consumer Database 316 may also serve as the primary database in which the data user 300 correlates its customer data with other sources of data. For example, as shown in process "A," the Customer Acquisition System 310 may, upon the receipt of information of for a prospective customer "Customer A" (e.g., name and address), send the received prospective customer information to the Consumer Data Delivery System 312 to request a lookup of "Customer A" in the non-regulated data sources 302. In one embodiment, as shown in process "B," the Consumer Data Delivery System 312 attempts to locate "Customer A" in the CDI Consumer Database 316 using the received information, and return, to the Customer Acquisition System 310, the customer data ID(s) of the matched record(s) for "Customer A" within the CDI Consumer Database 316, along with other data from data sources 302 that are associated with "Customer A."

Non-regulated data sources 302 may include a government database such as one managed by the Office of Foreign Assets Control (OFAC) and a fraud database such as the National Fraud Database. For example, if the data user 300 is a credit card company, the returned information from the CDI Consumer Database and/or other related non-regulated data sources may contain information related to the prospective customer that can help the credit card company assess the type of products in which the prospective customer may be interested, and/or whether the prospective customer may be a high fraud risk. In one embodiment, the customer data ID from the CDI Consumer Database 316 is returned to the data user 300 and saved in the customer database 338. The customer data ID for "Customer A" is then used as the integrated identifier to access both regulated and non-regulated information. In the example of "Customer A," the result may be that he or she becomes pre-approved based on the information received. Both the Non-Regulated Shadow Customer Database 314 and the Customer Database 338 may be updated to reflect that "Customer A" has been pre-approved and that an integrated identifier has been assigned to him or her.

In one or more embodiments, a list of prospective customers may be provided by the Customer Acquisition System 310 to the Consumer Data Delivery System 312, which in turn may locate data records for the list of prospective customers from among the non-regulated data sources 302. In addition, the Consumer Data Delivery System 312 may also query the Non-Regulated Shadow Customer Database 314 to check if any of the prospective customers are already existing customers of the data user 300.

Although a number of modules depicted include the term "consumer," embodiments provide the same data management capability for data users that manage business customers. Thus, in one or more embodiments, the Consumer Data Delivery System 312 may access a CDI Business Database instead of or in addition to the CDI Consumer Database 316.

Regulated Data Sources

Embodiments also provide methods and systems for data users to access regulated data sources. As shown in process "C," the Consumer Credit Online System 322 may receive credit queries from the Customer Acquisition System 310. In one embodiment, the Consumer Credit Online System 322 interfaces with regulated data sources 346 such as a Consumer Credit Database 348. Using the "Customer A" example, after receiving a pre-approval notice, "Customer A" may submit a credit application to the data user 300. The Consumer Credit Online System 322 may then receive queries from the Customer Acquisition System 310 to obtain credit reports for "Customer A," under the permissible purpose of determining credit-worthiness, for example. In the process "D," "Customer A's" credit reports are obtained from a Consumer Credit Database 348. The retrieved reports are then returned to the data user 300.

The data user 300 may also operate a Customer Management System 334 that handles tasks such as account creation and account maintenance. Tracking along with the example, if the returned credit reports are satisfactory, "Customer A" may be approved for a new account and the Customer Management System 334 may handle the creation of the account. As shown in process "E," the Customer Management System 334 may send "Customer A's" new account information along with the assigned integrated identifier to a Customer Update System 332, which manages additions and updates in one embodiment via an Identifier Reconciliation System 318. The Customer Management System 334 may forward the integrated identifier in the process "F" to the Identifier Reconciliation System 318, and the identifier reconciliation process as shown in FIG. 2B may be triggered so that the Non-Regulated Shadow Customer Database 314, the Regulated Shadow Customer Database 352, and/or other databases are updated. The Customer Data Update System may also receive updates from the Customer Management System 334 reflecting changes in the Customer Database 338. In one embodiment, the updates are sent with the integrated identifiers, which are resolved in accordance to the resolution process shown in FIGS. 2A and 2C, so that the appropriate shadow databases and/or regulated or non-regulated data sources are updated. In one embodiment, the updates can be processed in by transaction or in a batch mode.

The data user 300 may also operate an Account Review System 336 that forwards customer information along with the integrated identifiers to the counterpart Account Review System 342 of the data provider 350, as shown in process "G." For example, if the data user 300 is a credit card company, the information may include account numbers. In one embodiment, the account numbers and identifiers are then sent to the Identifier Reconciliation System 318, as shown in process "H." The Identifier Reconciliation System 318 may then resolve to the proper regulated identifiers based on its linkage table and then access the Consumer Credit Database 348 to obtain data records needed for the account review. The results are then returned to the Account Review System 336.

CONCLUSION

All of the methods described herein may be performed and fully automated by a computer system. The computer system may, in some cases, be composed by multiple distinct computers or computing devices (e.g., physical servers, workstations, storage arrays, etc.) that communicate and interoperate over a network to perform the described functions. Each such computing device typically includes a processor (or multiple processors) that executes program instructions stored in a memory. The results of the disclosed methods may be persistently stored by transforming physical storage devices, such as solid state memory chips and/or magnetic disks, into a different state.

In addition, all of the methods/processes described above may be embodied in, and fully automated via, software code modules executed by one or more general purpose computers. The code module may be stored in any type of computer-readable medium or other computer storage device. Some or all of the methods may alternatively be embodied in specialized computer hardware. As will be apparent, the features, and attributes of the specific embodiments disclosed above may be combined in different ways to form additional embodiments, all of which are fall within the scope of the present disclosure. Although this disclosure has been described in terms of certain preferred embodiments and applications, other embodiments and applications that are apparent to those of ordinary skill in the art, including embodiments which do not provide all of the features and advantages set forth herein, are also within the scope of this disclosure. Accordingly, the scope of the disclosure is intended to be defined only by reference to the appended claims.

What is claimed is:

1. A computer-executable method comprising:
   receiving, by a computing system including one or more computer processors, an integrated data identifier associated with an entity from a data user, wherein the integrated data identifier is linked to a first data identifier and a second data identifier associated with the entity;
   applying one or more reconciliation rules to reconcile the integrated data identifier with the first data identifier and the integrated data identifier with the second data identifier, wherein the one or more reconciliation rules account for correspondence between data items with different permission levels;
   accessing, by the computing system, one or more first data items corresponding to the entity in a first data store;
   accessing, by the computing system, one or more second data items corresponding to the entity in a second data store; and
   transmitting the one or more first data items and the one or more second data items to the data user;
   wherein the integrated data identifier provides the data user with access to:
      the one or more first data items of the entity from the first data store according to a first access rights and without the first data identifier; and
      the one or more second data items of the entity from the second data store according to a second access rights and without the second data identifier.

2. The computer-executable method of claim 1, wherein the first data store and the second data store are different.

3. The computer-executable method of claim 1 further comprising:
   identifying, by the computing system, the first data identifier and the second data identifier based on the received integrated data identifier.

4. The computer-executable method of claim 3, wherein the first data identifier and the second data identifier are identified based on the applied one or more reconciliation rules.

5. The computer-executable method of claim 1, wherein the first data store is associated with a first permission level, and wherein the second data store is associated with a second permission level, and wherein the first permission level is different from the second permission level.

6. The computer-executable method of claim 1, wherein the one or more first data items comprise regulated data items that are subject to regulations on access.

7. The computer-executable method of claim 6, wherein the one or more second data items comprise unregulated data items that are not subject to regulations on access.

8. The computer-executable method of claim 1, wherein the first access rights are associated with the one or more first data items, wherein the second access rights are associated with the one or more second data items, and wherein the first access rights are different from the second access rights.

9. The computer-executable method of claim 1, wherein at least one of the first access rights and the second access rights include legal restrictions restricting linkage of the one or more first data items with the one or more second data items.

10. The computer-executable method of claim 1, wherein the entity comprises a person.

11. The computer-executable method of claim 1, wherein the entity comprises a business.

12. The computer-executable method of claim 1, wherein the integrated data identifier does not include personally identifiable information of the entity.

13. A system comprising:
a processing unit;
a memory in electronic communication with the processing unit;
computer-executable instructions stored in the memory, wherein the computer-executable instructions, when executed by the processing unit, cause the processing unit to:
receive an integrated data identifier associated with an entity from a data user, wherein the integrated data identifier is linked to a first data identifier and a second data identifier associated with the entity;
apply one or more reconciliation rules to reconcile the integrated data identifier with the first data identifier and the integrated data identifier with the second data identifier, wherein the one or more reconciliation rules account for correspondence between data items with different permission levels;
access one or more first data items corresponding to the entity in a first data store;
access one or more second data items corresponding to the entity in a second data store; and
transmit the one or more first data items and the one or more second data items to the data user;
wherein the integrated data identifier provides the data user with access to:
the one or more first data items of the entity from the first data store according to a first access rights and without the first data identifier; and
the one or more second data items of the entity from the second data store according to a second access rights and without the second data identifier.

14. A computer-executable method for updating user data in databases, the computer-executable method comprising:
receiving, by a computing system including one or more computer processors, a request from a data user for data items associated with a second database associated with an entity, the request comprising one or more first data items associated with a first database associated with the entity;
determining an integrated data identifier for the entity;
linking the integrated data identifier with a first data identifier and a second data identifier, wherein the first data identifier is associated with the first database, and wherein the second data identifier is associated with a second database;
based at least in part on the one or more first data items and the integrated data identifier, accessing, from the second database, one or more second data items associated with the entity;
transmitting the one or more second data items to the data user;
receiving, from the data user, updated information generated based at least in part on the one or more second data items, the updated information comprising a new first data item and a new second data item;
associating the integrated data identifier with the new first data item and the new second data item by linking the new first data item and the new second data item with the integrated data identifier.

15. The computer-executable method of claim 14, wherein the integrated data identifier provides the data user access to the new first data item without using the first data identifier and the new second data item without using the second data identifier.

16. The computer-executable method of claim 13, wherein the first data store is associated with a first permission level, and wherein the second data store is associated with a second permission level, and wherein the first permission level is different from the second permission level.

17. The computer-executable method of claim 14, wherein the one or more first data items comprise unregulated data items that are not subject to regulations on access.

18. The computer-executable method of claim 17, wherein the one or more second data items comprise regulated data items that are subject to regulations on access.

19. The computer-executable method of claim 14, wherein the entity comprises a person.

20. The computer-executable method of claim 14, wherein the entity comprises a business.

* * * * *